(12) United States Patent
Boyerinas

(10) Patent No.: US 12,365,711 B2
(45) Date of Patent: *Jul. 22, 2025

(54) TGFβ SIGNAL CONVERTOR

(71) Applicant: Regeneron Pharmaceuticals, Inc., Tarrytown, NY (US)

(72) Inventor: Benjamin Boyerinas, Brookline, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 130 days.

This patent is subject to a terminal disclaimer.

(21) Appl. No.: 18/297,491

(22) Filed: Apr. 7, 2023

(65) Prior Publication Data

US 2023/0364141 A1 Nov. 16, 2023

Related U.S. Application Data

(63) Continuation of application No. 16/348,450, filed as application No. PCT/US2017/062358 on Nov. 17, 2017, now Pat. No. 11,654,158.

(60) Provisional application No. 62/423,565, filed on Nov. 17, 2016, provisional application No. 62/467,496, filed on Mar. 6, 2017.

(51) Int. Cl.
| | | |
|---|---|---|
| *C07K 14/495* | (2006.01) | |
| *A61K 38/00* | (2006.01) | |
| *A61K 40/11* | (2025.01) | |
| *A61K 40/22* | (2025.01) | |
| *A61K 40/31* | (2025.01) | |
| *A61K 40/32* | (2025.01) | |
| *A61K 40/42* | (2025.01) | |
| *A61P 35/00* | (2006.01) | |
| *C07K 14/54* | (2006.01) | |
| *C07K 14/725* | (2006.01) | |
| *A61K 38/17* | (2006.01) | |
| *C07K 14/705* | (2006.01) | |

(52) U.S. Cl.
CPC ............ *C07K 14/495* (2013.01); *A61K 40/11* (2025.01); *A61K 40/22* (2025.01); *A61K 40/31* (2025.01); *A61K 40/32* (2025.01); *A61K 40/4204* (2025.01); *A61K 40/421* (2025.01); *A61K 40/4217* (2025.01); *A61K 40/4229* (2025.01); *A61K 40/4269* (2025.01); *A61P 35/00* (2018.01); *C07K 14/5434* (2013.01); *C07K 14/7051* (2013.01); *A61K 38/00* (2013.01); *A61K 38/1793* (2013.01); *C07K 14/70575* (2013.01); *C07K 2319/02* (2013.01); *C07K 2319/03* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 4,751,180 | A | 6/1988 | Cousens et al. |
| 4,935,233 | A | 6/1990 | Bell et al. |
| 5,994,136 | A | 11/1999 | Naldini et al. |
| 6,013,516 | A | 1/2000 | Verma et al. |
| 6,682,907 | B1 | 1/2004 | Charneau et al. |
| 6,692,736 | B2 | 2/2004 | Yu et al. |
| 11,654,158 | B2 | 5/2023 | Boyerinas |
| 2009/0222936 | A1 | 9/2009 | Richmond et al. |
| 2015/0266973 | A1 | 9/2015 | Jarjour et al. |
| 2016/0075755 | A1 | 3/2016 | Valdes et al. |
| 2017/0036091 | A1 | 2/2017 | Hooper et al. |
| 2017/0360913 | A1 | 12/2017 | Zhao et al. |
| 2018/0024479 | A1 | 1/2018 | Yamada et al. |
| 2018/0244797 | A1 | 8/2018 | Pulé et al. |
| 2019/0350974 | A1 | 11/2019 | Boyerinas |
| 2023/0044580 | A1 | 2/2023 | Mann et al. |
| 2023/0159612 | A1 | 5/2023 | Ellinger et al. |

FOREIGN PATENT DOCUMENTS

| | | |
|---|---|---|
| JP | 2009-514541 A | 4/2009 |
| JP | 2016-520302 A | 7/2016 |
| WO | WO-2007/054250 A1 | 5/2007 |
| WO | WO-2012/006635 A1 | 1/2012 |
| WO | WO-2012/138858 A1 | 10/2012 |
| WO | WO-2014/172584 A1 | 10/2014 |
| WO | WO-2015/017214 A1 | 2/2015 |
| WO | WO-2016/122738 A1 | 8/2016 |
| WO | WO-2016/164089 A2 | 10/2016 |
| WO | WO-2017/029512 A1 | 2/2017 |
| WO | WO-2018/094244 A1 | 5/2018 |
| WO | WO-2020/193767 A1 | 10/2020 |
| WO | WO-2020/227483 A1 | 11/2020 |

OTHER PUBLICATIONS

Extended European Search Report for EP Application No. 23216595.1 dated May 29, 2024.
International Preliminary Report on Patentability for International Application No. PCT/EP20/58779 dated Sep. 28, 2021.
International Preliminary Report on Patentability for International Application No. PCT/US2017/062358 dated May 21, 2019.
International Preliminary Report on Patentability for International Application No. PCT/US2020/031796 dated Nov. 2, 2021.
Kim et al., "High Cleavage Efficiency of a 2A Peptide Derived from Porcine Teschovirus-1 in Human Cell Lines, Zebrafish and Mice", PLoS ONE, vol. 6 (4) e18556, (2011).
Wang et al., "Detection of RNA Interference (RNAi) Mediated mRNA Cleavage in Fresh Injected Tumor Tissue from Patients in a Phase I Trial of pbi-shRNA (TM) Lipoplex Targeting Stathmin-1", Molecular Therapy. vol. 22. Nature Publishing Group, (2014).

(Continued)

*Primary Examiner* — Daniel C Gamett
(74) *Attorney, Agent, or Firm* — Foley Hoag LLP; Amy E. Mandragouras; Ariana D. Harris

(57) ABSTRACT

The present disclosure provides improved compositions for adoptive T cell therapies for treating, preventing, or ameliorating at least one symptom of a cancer, infectious disease, autoimmune disease, inflammatory disease, and immunodeficiency, or condition associated therewith.

24 Claims, 24 Drawing Sheets

Specification includes a Sequence Listing.

(56) References Cited

OTHER PUBLICATIONS

Watanabe et al., "Conferring CAR T Cells With Resistance to TGFbeta1 Using a Signal Converter," Molecular Therapy, May 2014, vol. 22, Supplement 1, pp. S298-S299.

Zhu et al., "A Pivotal Role for the Transmembrane Domain in Transforming Growth Factor-b Receptor Activation", The Journal of Biological Chemistry, vol. 274, No. 17, Issue of Apr. 23, p. 11773-11781, (1999).

Asao et al., "Cutting Edge: The Common y-Chain Is an Indispensable Subunit of the IL-21 Receptor Complex," The Journal of Immunology, 2001, 167, 1-5.

Bird et al. "Single-chain antigen-binding proteins." Science (1988); 242.4877: 423-427.

Challita et al., "Multiple modifications in cis elements of the long terminal repeat of retroviral vectors lead to increased expression and decreased DNA methylation in embryonic carcinoma cells." J Virol. (1995); 69(2): 748-755.

Chaudhary et al. "A rapid method of cloning functional variable-region antibody genes in *Escherichia coli* as single-chain immunotoxins." Proceedings of the National Academy of Sciences (1990); 87.3: 1066-1070 (and correction).

Cheung et al., "Accessory Protein-Like Is Essential for IL-18-Mediated Signaling," The Journal of Immunology, 2005, 174, 5351-5357.

Clever, J. et al., "RNA Secondary Structure and Binding Sites for gag Gene Products in the 5' Packaging Signal of Human Immunodeficiency Virus Type 1." J. of Virology (1995); 69(4): 21012109.

Cooper et al. "T-cell clones can be rendered specific for CD19: Toward the selective augmentation of the graft-versus-B-lineage leukemia effect." Blood (2003); 101.4: 1637-1644.

Cullen et al., "Regulatory Pathways Governing HIV-1 Replication", Cell (1989); 58: 423-426.

Cullen, "Human Immunodeficiency Virus as a Prototypic Complex Retrovirus", Journal of Virology (1991); 65(3): 1053-1056.

De Felipe et al., "Targeting of proteins derived from self-processing polyproteins containing multiple signal sequences." Traffic (2004); 5.8: 616-626.

Desjarlais et al., "Length-encoded multiplex binding site determination: application to zinc finger proteins," Proceedings of the National Academy of Sciences (1994); 91.23: 11099-11103.

Desjarlais et al., "Use of a zinc-finger consensus sequence framework and specificity rules to design specific DNA binding proteins." Proceedings of the National Academy of Sciences (1993); 90.6: 2256-2260.

Duke et al., Sequence and structural elements that contribute to efficient encephalomyocarditis virus RNA translation, J Virol. Mar. 1992;66(3):1602-9.

Dull et al., "A third-generation lentivirus vector with a conditional packaging system", Journal of Virology (1998); 72(11): 8463-8671.

Extended European Search Report for EP Application No. 17872043.9 mailed on Mar. 30, 2020, 12 pages.

Fukuo, "Interleukin 2, IL-2," The Journal of Japan Atherosclerosis Society, 1996, 24, 4-5, 155-161.

Huang et al., "Role of the hepatitis B virus posttranscriptional regulatory element in export of intronless transcripts," Molecular and Cellular Biology (1995); 15(7): 3864-3869.

Huez et al., "Two independent internal ribosome entry sites are involved in translation initiation of vascular endothelial growth factor mRNA," Mol Cell Biol. Nov. 1998;18(11):6178-90.

International Search Report and Written Opinion for International Application No. PCT/US2017/062358, dated Apr. 3, 2018, 16 pages.

International Search Report and Written Opinion mailed on Oct. 14, 2020, for International Application No. PCT/US2020/031796, 16 pages.

Irion et al., "Identification and targeting of the ROSA26 locus in human embryonic stem cells", Nat Biotechnol. (2007); 25(12):1477-1482.

Jackson, et al., "Internal initiation of translation in eukaryotes: the picornavirus paradigm and beyond", RNA. (1995); 1(10): 985-1000.

Jackson, et al., "The novel mechanism of initiation of picornavirus RNA translation", Trends Biochem Sci. (1990); 15(12): 477-483.

Jena et al., "Driving CAR-Based T-Cell Therapy to Success," Curr Hematol Malig Rep. Mar. 2014; 9(1):50-56.

Kim et al. "Hybrid restriction enzymes: zinc finger fusions to Fok I cleavage domain." Proceedings of the National Academy of Sciences (1996); 93.3: 1156-1160.

Kutner et al., "Production, concentration and titration of pseudotyped HIV-1-based lentiviral vectors", Nature Protocols (2009); 4: 495-505.

Kutner et al., "Simplified production and concentration of HIV-1-based lentiviral vectors using HYPERFlask vessels and anion exchange membrane chromatography", BMC Biotechnol. (2009); 9:10. p. 1-7.

Liu et al. "Design of polydactyl zinc-finger proteins for unique addressing within complex genomes." Proceedings of the National Academy of Sciences (1997); 94.11: 5525-5530.

Liu et al. (2016). "A chimeric switch-receptor targeting PD1 augments the efficacy of second-generation CAR T cells in advanced solid tumors," Cancer Res. 76:1578-1590.

Liu et al., "HnRNP L binds a cis-acting RNA sequence element that enables intron-dependent gene expression," Genes & Dev. (1995); 9: 1766-1780.

Maratea et al., "Deletion and fusion analysis of the phage phi X174 lysis gene E," Gene. 1985;40(1):39-46.

Murphy et al., "Genetic construction, expression, and melanoma-selective cytotoxicity of a diphtheria toxin-related alpha-melanocyte-stimulating hormone fusion protein," Proc Natl Acad Sci U S A. Nov. 1986;83(21):8258-62.

Naldini et al., "Efficient transfer, integration, and sustained long-term expression of the transgene in adult rat brains injected with a lentiviral vector", Proc Natl Acad Sci USA (1996); 93(21): 11382-11388.

Naldini et al., "In vivo gene delivery and stable transduction of nondividing cells by a lentiviral vector", Science (1996); 272(5259): 263-267.

Naldini, "Lentiviruses as gene transfer agents for delivery to non-dividing cells", Curr Opin Biotechnol. (1998); 5: 457-463.

Office Action for JP Application No. 2019-526305 dated Jul. 4, 2022, 10 pages.

Office Action for JP Application No. 2019-526305, dated Oct. 4, 2021, 9 pages.

Ozaki et al., "Cytokine and Cytokine Receptor Pleiotropy and Redundancy," The Journal of Biological Chemistry, Aug. 16, 2002, 277,33, 29355-29358.

Patel et al., "Impact of chimeric immune receptor extracellular protein domains on T cell function." Gene Ther (1999); 6(3): 412-419.

Pomerantz et al., "Analysis of homeodomain function by structure-based design of a transcription factor," Proc Natl Acad Sci USA Oct. 10, 1995;92(21):9752-6.

Pomerantz et al., "Structure-based design of transcription factors." Science (1995); 267.5194: 93-96.

Ryan et al., "Virus-encoded proteinases of the picornavirus supergroup." J Gen Virol. (1997); 78 (Pt 4): 699-723.

Shi et al., "Chimeric antigen receptor for adoptive immunotherapy of cancer: latest research and future prospects," Molecular Cancer 2014, 13:219, 8 pages.

Supplementary European Search Report for EP Application No. 20802730.0 dated Jul. 11, 2023, 6 pages.

Szymczak et al. "Correction of multi-gene deficiency in vivo using a single'self-cleaving'2A peptide-based retroviral vector." Nature Biotechnology (2004); 22.5: 589-594.

Takara Bio Inc., Idenshidonyujikken handobukku (handbook of gene transfer experimentation), Nov. 2015, p. 1-10.

Third Party Submission Under 37 CFR 1.290 submitted on Sep. 1, 2020, for U.S. Appl. No. 16/348,450, 9 pages.

Wang et al., "Detection of RNA Interference (RNAi) Mediated mRNA Cleavage in Fresh Injected Tumor Tissue from Patients in a

(56) References Cited

OTHER PUBLICATIONS

Phase I Trial of pbi-shRNATM Lipoplex Targeting Stathmin-1," Molecular Therapy, May 2014, vol. 22, Supplement 1, pp. S298-S299.

Yang et al., "Development of optimal bicistronic lentiviral vectors facilitates high-level TCR gene expression and robust tumor cell recognition", Gene Therapy, Nov. 2008, vol. 15, No. 21, pp. 1411-1423.

Zennou et al., "HIV-1 genome nuclear import is mediated by a central DNA flap," Cell. Apr. 14, 2000;101(2):173-85.

Zhang et al., "Engineering CAR-T cells," Biomarker Research (2017) 5:22, 6 pages.

Zufferey et al., "Multiply attenuated lentiviral vector achieves efficient gene delivery in vivo", Nat Biotechnol. (1997), 15(9): 871-875.

Zufferey et al., "Woodchuck hepatitis virus posttranscriptional regulatory element enhances expression of transgenes delivered by retroviral vectors." J Virol. (1999); 73(4): 2886-2892.

Boyerinas et al., "A novel TGF-[beta]-/IL-12R signal conversion platform that protects CAR T cells from TGF-[beta]-mediated immune suppression and concurrently amplifies effector function." Cancer Research 77.13_Supplement (2017): 602-602.

Dotto et al., "Squamous cell cancers: a unified perspective on biology and genetics." Cancer Cell 29(5) (2016): 622-637.

Presky et al., "A functional interleukin 12 receptor complex is composed of two beta-type cytokine receptor subunits." Proc Natl Acad Sci US A Nov. 26, 1996;93(24):14002-7.

Yang et al., "T-cell lineage determination." Immunol Rev. Nov. 2010;238(1): 12-22.

*compiled data from 3 donors
**value off scale -out of linear range of assay

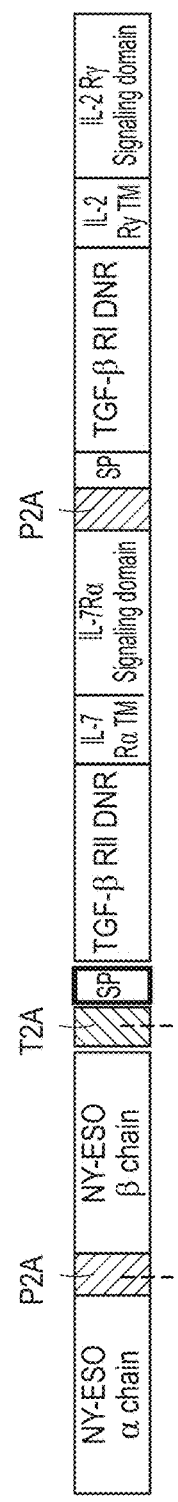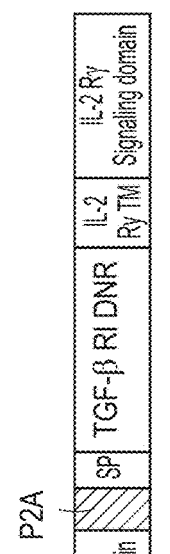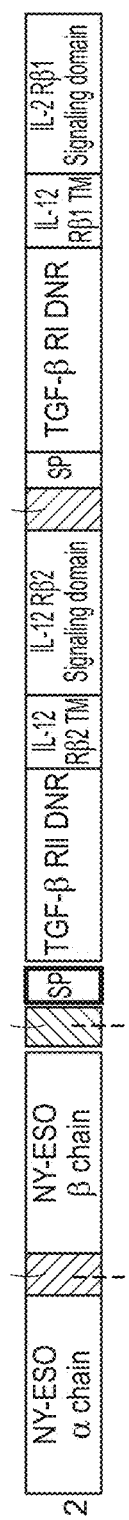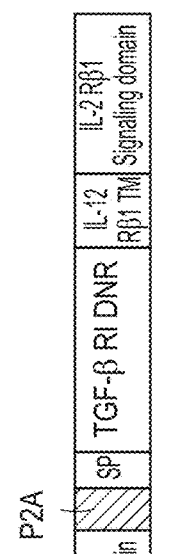
FIGURE 20

FIGURE 23
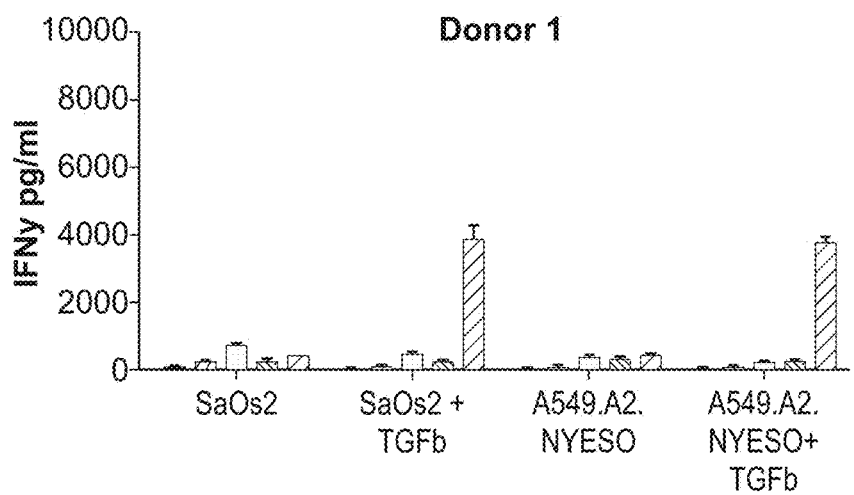
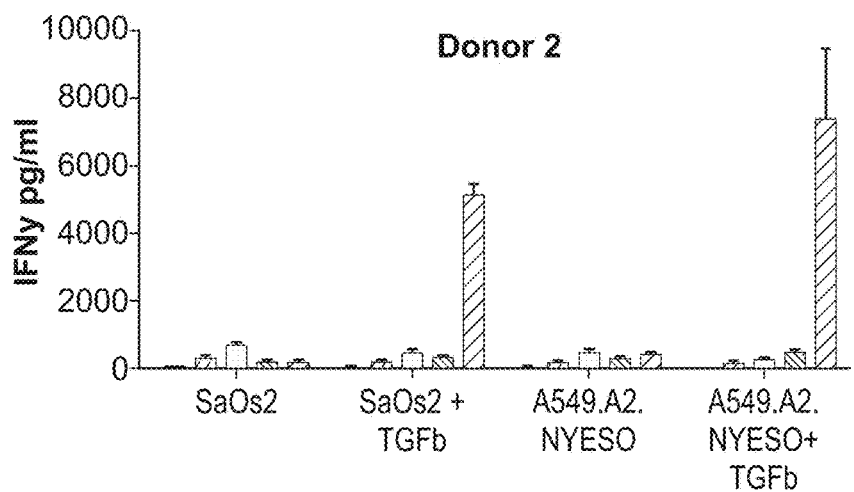
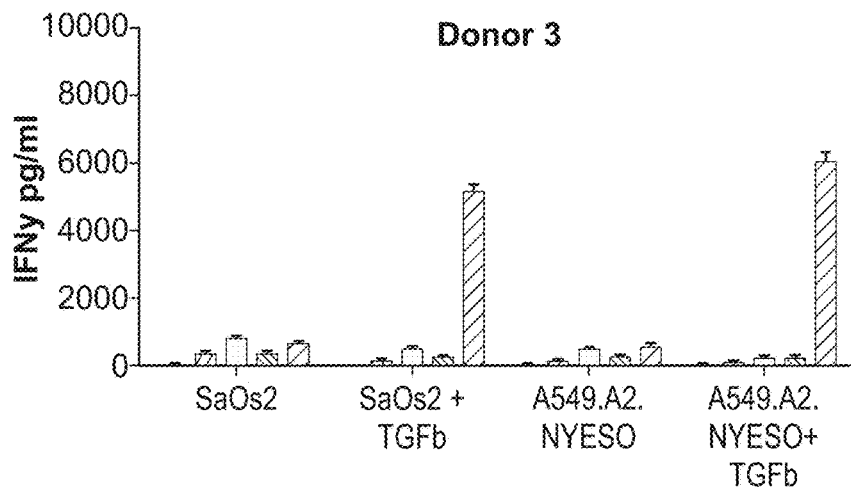

```
SEQUENCE LISTING

Sequence total quantity: 76
SEQ ID NO: 1            moltype = AA  length = 507
FEATURE                 Location/Qualifiers
source                  1..507
                        mol_type = protein
                        organism = Homo sapiens
SEQUENCE: 1
MEAVAAPRP  RLLLLVLAAA  AAAAAALLPG  ATALQCFCHL  CTKDNFTCVT  DGLCFVSVTE   60
TTDKVIHNSM CIAEIDLIPR  DRPFVCAPSS  KTGSVTTTYC  CNQDHCNKIE  LPTTGPFSVK  120
SSPGLGPVEL AAVIAGPVCF  VCISLMLMVY  ICHNRTVIHH  RVPNEEDPSL  DRPFISEGTT  180
LKDLIYDMTT SGSGSGLPLL  VQRTIARTIV  LQESIGKGRF  GEVWRGKWRG  EEVAVKIFSS  240
REERSWFREA EIYQTVMLRH  ENILGFIAAD  NKDNGTWTQL  WLVSDYHEHG  SLFDYLNRYT  300
VTVEGMIKLA LSTASGLAHL  HMEIVGTQGK  PAIAHRDLKS  KNILVKKNGT  CCIADLGLAV  360
RHDSATDTID IAPNHRVGTK  RYMAPEVLDD  SINMKHFESF  KRADIYAMGL  VFWEIARRCS  420
IGGIHEDYQL PYYDLVPSDP  SVEEMRKVVC  EQKLRPNIPN  RWQSCEALRV  MAKIMRECWY  480
ANGAARLTAL RIKKTLSQLS  QQEGIKM                                         507

SEQ ID NO: 2            moltype = AA  length = 567
FEATURE                 Location/Qualifiers
source                  1..567
                        mol_type = protein
                        organism = Homo sapiens
SEQUENCE: 2
MGRGLLRGLW PLHIVLWTRI  ASTIPPHVQK  SVNNDMIVTD  NNGAVKFPQL  CKFCDVRFST   60
CDNQKSCMSN CSITSICEKP  QEVCVAVWRK  NDENITLETV  CHDPKLPYHD  FILEDAASPK  120
CIMKEKKKPG ETFFMCSCSS  DECNDNIIFS  EEYNTSNPDL  LLVIFQVTGI  SLLPPLGVAI  180
SVIIIFYCYR VNRQQKLSST  WETGKTRKLM  EFSEHCAIIL  EDDRSDISST  CANNINHNTE  240
LLPIELDTLV GKGRFAEVYK  AKLKQNTSEQ  FETVAVKIFP  YEEYASWKTE  KDIFSDINLK  300
HENILQFLTA EERKTELGKQ  YWLITAPHAK  GNLQEYLTRH  VISWEDLRKL  GSSLARGIAH  360
LHSDHTPCGR PKMPIVHRDL  KSSNILVKND  LTCCLCDFGL  SLRLDPTLSV  DDLANSGQVG  420
TARYMAPEVL ESRMNLENVE  SFKQTDVYSM  ALVLWEMTSR  CNAVGEVKDY  EPPFGSKVRE  480
HPCVESMKDN VLRDRGRPEI  PSFWLNHQGI  QMVCETLTEC  WDHDPEARLT  AQCVAERFSE  540
LEHLDRLSGR SCSEEKIPED  GSLNTTK                                         567

SEQ ID NO: 3            moltype = AA  length = 662
FEATURE                 Location/Qualifiers
source                  1..662
                        mol_type = protein
                        organism = Homo sapiens
SEQUENCE: 3
MEPLVTWVVP LLFLFLLSRQ  GAACRTSECC  FQDPPYPDAD  SGSASGPRDL  RCYRISSDRY   60
ECSWQYEGPT AGVSHFLRCC  LSSGRCCYFA  AGSATRLQFS  DQAGVSVLYT  VTLWVESWAR  120
NQTEKSPEVT LQLYNSVKYE  PPLGDIKVSK  LAGQLRMEWE  TPDNQVGAEV  QFRHRTPSSP  180
WKLGDCGPQD DDTESCLCPL  EMNVAQEFQL  RRRQLGSQGS  SWSKWSSPVC  VPPENPPQPQ  240
VRFSVEQLGQ DGRRRLTLKE  QPTQLELPEG  CQGLAPGTEV  TYRLQLHMLS  CPCKAKATRT  300
LHLGKMPYLS GAAYNVAVIS  SNQFGPGLNQ  TWHIPADTHT  EPVALNISVG  TNGTTMYWPA  360
RAQSMTYCIE WQPVGQDGGL  ATCSLTAPQD  PDPAGMATYS  WSRESGAMGQ  EKCYYITIFA  420
SAHPEKLTLW STVLSTYHFG  GNASAAGTPH  HVSVKNHSLD  SVSVDWAPSL  LSTCPGVLKE  480
YVVRCRDEDS KQVSEHPVQP  TETQVTLSGL  RAGVAYTVQV  RADTAWLRGV  WSQPQRFSIE  540
VQVSDWLIFF ASLGSFLSIL  LVGVLGYLGL  NRAARHLCPP  LPTPCASSAI  EFPGGKETWQ  600
WINPVDFQEE ASLQEALVVE  MSWDKGERTE  PLEKTELPEG  APELALDTEL  SLEDGDRCKA  660
KM                                                                     662
```

```
SEQ ID NO: 4              moltype = AA   length = 776
FEATURE                   Location/Qualifiers
source                    1..776
                          mol_type = protein
                          organism = Homo sapiens
SEQUENCE: 4
MAHTFRGCSL AFMFIITWLL IKAKIDACKR GDVTVKPSHV ILLGSTVNIT CSLKPRQGCF    60
HYSRRNKLIL YKFDRRINFH HGHSLNSQVT GLPLGTTLFV CKLACINSDE IQICGAEIFV   120
GVAPEQPQNL SCIQKGEQGT VACTWERGRD THLYTEYTLQ LSGPKNLTWQ KQCKDIYCDY   180
LDFGINLTPE SPESNFTAKV TAVNSLGSSS SLPSTFTFLD IVRPLPPWDI RIKFQKASVS   240
RCTLYWRDEG LVLLNRLRYR PSNSRLWNMV NVTKAKGRHD LLDDKPFTEY EFQISSKLHL   300
YKGSWSDWSE SLRAQTPEEE PTGMLDVWYM KRHIDYSRQQ ISLFWKNLSV SEARGKILHY   360
QVTLQELTGG KAMTQNITGH TSWTTVIPRT GNWAVAVSAA NSKGSSLPTR INIMNLCEAG   420
LLAPRQVSAN SEGMDNILVT WQPPRKDPSA VQEYVVEWRE LHPGGDTQVP LNWLRSRPYN   480
VSALISEIPY RVSQNSHPIN SLQPRVTYVL WMTALTAAGE SSHGNEREFC LQGKANWMAF   540
VAPSICIAII MVGIFSTHYF QQKVFVLLAA LRPQWCSREI PDPANSTCAK KYPIAEEKTQ   600
LPLDRLLIDW PTPEDPEPLV ISEVLHQVTP VFRHPPCSNW PQREKGIQGH QASEKDMMHS   660
ASSPPPPRAL QAESRQLVDL YKVLESRGSD PKPENPACPW TVLPAGDLPT HDGYLPSNID   720
DLPSHEAPLA DSLEELEPQH ISLSVFPSSS LHPLTFSCGD KLTLDQLKMR CDSLML       776

SEQ ID NO: 5              moltype = AA   length = 459
FEATURE                   Location/Qualifiers
source                    1..459
                          mol_type = protein
                          organism = Homo sapiens
SEQUENCE: 5
MTILGTTFGM VFSLLQVVSG ESGYAQNGDL EDAELDDYSF SCYSQLEVNG SQHSLTCAFE    60
DPDVNTTNLE FEICGALVEV KCLNFRKLQE IYFIETKKFL LIGKSNICVK VGEKSLTCKK   120
IDLTTIVKPE APFDLSVIYR EGANDFVVTF NTSHLQKKYV KVLMHDVAYR QEKDENKWTH   180
VNLSSTKLTL LQRKLQPAAM YEIKVRSIPD HYFKGFWSEW SPSYYFRTPE INNSSGEMDP   240
ILLTISILSF FSVALLVILA CVLWKKRIKP IVWPSLPDHK KTLEHLCKKP RKNLNVSFNP   300
ESFLDCQIHR VDDIQARDEV EGFLQDTFPQ QLEESEKQRL GGDVQSPNCP SEDVVITPES   360
FGRDSSLTCL AGNVSACDAP ILSSSRSLDC RESGKNGPHV YQDLLLSLGT TNSTLPPPFS   420
LQSGILTLNP VAQGQPILTS LGSNQEEAYV TMSSFYQNQ                          459

SEQ ID NO: 6              moltype = AA   length = 369
FEATURE                   Location/Qualifiers
source                    1..369
                          mol_type = protein
                          organism = Homo sapiens
SEQUENCE: 6
MLKPSLPFTS LLFLQLPLLG VGLNTTILTP NGNEDTTADF FLTTMPTDSL SVSTLPLPEV    60
QCFVFNVEYM NCTWNSSSEP QPTNLTLHYW YKNSDNDKVQ KCSHYLFSEE ITSGCQLQKK   120
EIHLYQTFVV QLQDPREPRR QATQMLKLQN LVIPWAPENL TLHKLSESQL ELNWNNRFLN   180
HCLEHLVQYR TDWDHSWTEQ SVDYRHKFSL PSVDGQKRYT FRVRSRFNPL CGSAQHWSEW   240
SHPIHWGSNT SKENPFLFAL EAVVISVGSM GLIISLLCVY FWLERTMPRI PTLKNLEDLV   300
TEYHGNFSAW SGVSKGLAES LQPDYSERLC LVSEIPPKGG ALGEGPGASP CNQHSPYWAP   360
PCYTLKPET                                                          369

SEQ ID NO: 7              moltype = AA   length = 551
FEATURE                   Location/Qualifiers
source                    1..551
                          mol_type = protein
                          organism = Homo sapiens
SEQUENCE: 7
MAAPALSWRL PLLILLLPLA TSWASAAVNG TSQFTCFYNS RANISCVWSQ DGALQDTSCQ    60
VHAWPDRRRW NQTCELLPVS QASWACNLIL GAPDSQKLTT VDIVTLRVLC REGVRWRVMA   120
IQDFKPFENL RLMAPISLQV VHVETHRCNI SWEISQASHY FERHLEFEAR TLSPGHTWEE   180
APLLTLKQKQ EWICLETLTP DTQYEFQVRV KPLQGEFTTK SPWSQPLAFR TKPAALGKDT   240
IPWLGHLLVG LSGAFGFIIL VYLLINCRNT GPWLKKVLKC NTPDPSKFFS QLSSEHGGDV   300
QKWLSSPFPS SSFSPGGLAP EISPLEVLER DKVTQLLLQQ DKVPEPASLS SNHSLTCFT    360
NQGYFFFHLP DALEIEACQV YFTYDPYSEE DPDEGVAGAP TGSSPQPLQP LSGEDDAYCT   420
FPSRDDLLLF SPSLLGGPSP PSTAPGGSGA GEERMPPSLQ ERVPRDWDPQ PLGPPTGVP   480
DLVDFQPPPE LVLREAGEEV PDAGPREGVS FPWSRPPGQG EFRALNARLP LNTDAYLSLQ   540
ELQGQDPTHL V                                                       551

SEQ ID NO: 8              moltype = AA   length = 538
FEATURE                   Location/Qualifiers
source                    1..538
                          mol_type = protein
                          organism = Homo sapiens
SEQUENCE: 8
MPRGWAAPLL LLLLQGGWGC PDLVCYTDYL QTVICILEMW NLHPSTLTLT WQDQYEELKD    60
EATSCSLHRS AHNATHATYT CHMDVFHFMA DDIFSVNITD QSGNYSQECG SFLLAESIKP   120
APPFNVTVTF SGQYNISWRS DYEDPAFYML KGKLQYELQY RNRGDPWAVS PRRKLISVDS   180
RSVSLLPLEF RKDSSYELQV RAGPMPGSSY QGTWSEWSDP VIFQTQSEEL KEGWNPHLLL   240
LLLLVIVFIP AFWSLKTHPL WRLWKKIWAV PSPERFFMPL YKGCSGDFKK WVGAPFTGSS   300
LELGPWSPEV PSTLEVYSCH PPRSPAKRLQ LTELQEPAEL VESDGVPKPS FWPTAQNSGG   360
SAYSEERDRP YGLVSIDTVT VLDAEGPCTW PCSCEDDGYP ALDLDAGLEP SPGLEDPLLD   420
```

```
AGTTVLSCGC VSAGSPGLGG PLGSLLDRLK PPLADGEDWA GGLPWGGRSP GGVSESEAGS  480
PLAGLDMDTF DSGFVGSDCS SPVECDFTSP GDEGPPRSYL RQWVVIPPPL SSPGPQAS    538

SEQ ID NO: 9              moltype = AA  length = 541
FEATURE                   Location/Qualifiers
source                    1..541
                          mol_type = protein
                          organism = Homo sapiens
SEQUENCE: 9
MNCRELPLTL WVLISVSTAE SCTSRPHITV VEGEPFYLKH CSCSLAHEIE TTTKSWYKSS   60
GSQEHVELNP RSSSRIALHD CVLEFWPVEL NDTGSYFFQM KNYTQKWKLN VIRRNKHSCF  120
TERQVTSKIV EVKKFFQITC ENSYYQTLVN STSLYKNCKK LLLENNKNPT IKKNAEFEDQ  180
GYYSCVHFLH HNGKLFNITK TFNITIVEDR SNIVPVLLGP KLNHVAVELG KNVRLNCSAL  240
LNEEDVIYWM FGEENGSDPN IHEEKEMRIM TPEGKWHASK VLRIENIGES NLNVLYNCTV  300
ASTGGTDTKS FILVRKADMA DIPGHVFTRG MIIAVLILVA VVCLVTVCVI YRVDLVLFYR  360
HLTRRDETLT DGKTYDAFVS YLKECRPENG EEHTFAVEIL PRVLEKHFGY KLCIFERDVV  420
PGGAVVDEIH SLIEKSRRLI IVLSKSYMSN EVRYELESGL HEALVERKIK IILIEFTPVT  480
DFTFLPQSLK LLKSHRVLKW KADKSLSYNS RFWKNLLYLM PAKTVKPGRD EPEVLPVLSE  540
S                                                                 541

SEQ ID NO: 10             moltype = AA  length = 599
FEATURE                   Location/Qualifiers
source                    1..599
                          mol_type = protein
                          organism = Homo sapiens
SEQUENCE: 10
MLCLGWIFLW LVAGERIKGF NISGCSTKKL LWTYSTRSEE EFVLFCDLPE PQKSHFCHRN   60
RLSPKQVPEH LPFMGSNDLS DVQWYQQPSN GDPLEDIRKS YPHIIQDKCT LHFLTPGVNN  120
SGSYICRPKM IKSPYDVACC VKMILEVKPQ TNASCEYSAS HKQDLLLGST GSISCPSLSC  180
QSDAQSPAVT WYKNGKLLSV ERSNRIVVDE VYDYHQGTYV CDYTQSDTVS SWTVRAVVQV  240
RTIVGDTKLK PDILDPVEDT LEVELGKPLT ISCKARFGFE RVFNPVIKWY IKDSDLEWEV  300
SVPEAKSIKS TLKDEIIERN IILEKVTQRD LRRKFVCFVQ NSIGNTTQSV QLKEKRGVVL  360
LYILLGTIGT LVAVLAASAL LYRHWIEIVL LYRTYQSKDQ TLGDKKDFDA FVSYAKWSSF  420
PSEATSSLSE EHLALSLFPD VLENKYGYSL CLLERDVAPG GVYAEDIVSI IKRSRRGIFI  480
LSPNYVNGPS IFELQAAVNL ALDDQTLKLI LIKFCYFQEP ESLPHLVKKA LRVLPTVTWR  540
GLKSVPPNSR FWAKMRYHMP VKNSQGFTWN QLRITSRIFQ WKGLSRTETT GRSSQPKEW   599

SEQ ID NO: 11             moltype = AA  length = 569
FEATURE                   Location/Qualifiers
source                    1..569
                          mol_type = protein
                          organism = Homo sapiens
SEQUENCE: 11
MKVLLRLICF IALLISSLEA DKCKEREEKI ILVSSANEID VRPCPLNPNE HKGTITWYKD   60
DSKTPVSTEQ ASRIHQHKEK LWFVPAKVED SGHYYCVVRN SSYCLRIKIS AKFVENEPNL  120
CYNAQAIFKQ KLPVAGDGGL VCPYMEFFKN ENNELPKLQW YKDCKPLLLD NIHFSGVKDR  180
LIVMNVAEKH RGNYTCHASY TYLGKQYPIT RVIEFITLEE NKPTRPVIVS PANETMEVDL  240
GSQIQLICNV TGQLSDIAYW KWNGSVIDED DPVLGEDYYS VENPANKRRS TLITVLNISE  300
IESRFYKHPF TCFAKNTHGI DAAYIQLIYP VTNFQKHMIG ICVTLTVIIV CSVFIYKIFK  360
IDIVLWYRDS CYDFLPIKAS DGKTYDAYIL YPKTVGEGST SDCDIFVFKV LPEVLEKQCG  420
YKLFIYGRDD YVGEDIVEVI NENVKKSRRL IIILVRETSG FSWLGGSSEE QIAMYNALVQ  480
DGIKVVLLEL EKIQDYEKMP ESIKFIKQKH GAIRVWSGDFT QGPQSAKTRF WKNVRYHMPV  540
QRRSPSSKHQ LLSPATKEKL QREAHVPLG                                   569

SEQ ID NO: 12             moltype = AA  length = 570
FEATURE                   Location/Qualifiers
source                    1..570
                          mol_type = protein
                          organism = Homo sapiens
SEQUENCE: 12
MTLLWCVVSL YFYGILQSDA SERCDDWGLD TMRQIQVFED EPARIKCPLF EHFLKFNYST   60
AHSAGLTLIW YWTRQDRDLE EPINFRLPEN RISKEKDVLW FRPTLLNDTG NYTCMLRNTT  120
YCSKVAFPLE VVQKDSCFNS PMKLPVHKLY IEYGIQRITC PNVDGYFPSS VKPTITWYMG  180
CYKIQNFNNV IPEGMNLSFL IALISNNGNY TCVVTYPENG RTFHLTRTLT VKVVGSPKNA  240
VPPVIHSPND HVVYEKEPGE ELLIPCTVYF SFLMDSRNEV WWTIDGKKPD DITIDVTINE  300
SISHSRTEDE TRTQILSIKK VTSEDLKRSY VCHARSAKGE VAKAAKVKQK VPAPRYTVEL  360
ACGFGATVLL VVILIVYHV YWLEMVLFYR AHFGTDETIL DGKEYDIYVS YARNAEEEEF  420
VLLTLRGVLE NEFGYKLCIF DRDSLPGGIV TDETLSFIQK SRRLLVVLSP NYVLQGTQAL  480
LELKAGLENM ASRGNINVIL VQYKAVKETK VKELKRAKTV LTVIKWKGEK SKYPQGRFWK  540
QLQVAMPVKK SPRRSSSDEQ GLSYSSLKNV                                  570

SEQ ID NO: 13             moltype = AA  length = 557
FEATURE                   Location/Qualifiers
source                    1..557
                          mol_type = protein
                          organism = Homo sapiens
SEQUENCE: 13
MMVVLLGATT LVLVAVAPWV LSAAAGGKNL KSPQKVEVDI IDDNFILRWN RSDESVGNVT   60
FSFDYQKTGM DNWIKLSGCQ NITSTKCNFS SLKLNVYEEI KLRIRAEKEN TSSWYEVDSF  120
```

```
TPFRKAQIGP PEVHLEAEDK AIVIHISPGT KDSVMWALDG LSFTYSLVIW KNSSGVEERI    180
ENIYSRHKIY KLSPETTYCL KVKAALLTSW KIGVYSPVHC IKTTVENELP PPENIEVSVQ    240
NQNYVLKWDY TYANMTFQVQ WLHAFLKRNP GNHLYKWKQI PDCENVKTTQ CVFPQNVFQK    300
GIYLLRVQAS DGNNTSFWSE EIKFDTEIQA FLLPPVFNIR SLSDSFHIYI GAPKQSGNTP    360
VIQDYPLIYE IIFWENTSNA ERKIIEKKTD VTVPNLKPLT VYCVKARAHT MDEKLNKSSV    420
FSDAVCEKTK PGNTSKIWLI VGICIALFAL PFVIYAAKVF LRCINYVFFP SLKPSSSIDE    480
YFSEQPLKNL LLSTSEEQIE KCFIIENIST IATVEETNQT DEDHKKYSSQ TSQDSGNYSN    540
EDESESKTSE ELQQDFV                                                   557

SEQ ID NO: 14          moltype = AA  length = 515
FEATURE                Location/Qualifiers
source                 1..515
                       mol_type = protein
                       organism = Homo sapiens
SEQUENCE: 14
MLLSQNAFIF RSLNLVLMVY ISLVFGISYD SPDYTDESCT FKISLRNFRS ILSWELKNHS     60
IVPTHYTLLY TIMSKPEDLK VVKNCANTTR SFCDLTDEWR STHEAYVTVL EGFSGNTTLF    120
SCSHNFWLAI DMSFEPPEFE IVGFTNHINV MVKFPSIVEE ELQFDLSLVI EEQSEGIVKK    180
HKPEIKGNMS GNFTYIIDKL IPNTNYCVSV YLEHSDEQAV IKSPLKCTLL PPGQESESAE    240
SAKIGGIITV FLIALVLTST IVTLKWIGYI CLRNSLPKVL NFHNFLAWPF PNLPPLEAMD    300
MVEVIYINRK KKVWDYNYDD ESDSDTEAAP RTSGGGYTMH GLTVRPLGQA SATSTESQLI    360
DPESEEEPDL PEVDVELPTM PKDSPQQLEL LSGPCERRKS PLQDPFPEED YSSTEGSGGR    420
ITFNVDLNSV FLRVLDDEDS DDLEAPLMLS SHLEEMVDPE DPDNVQSNHL LASGEGTQPT    480
FPSPSSEGLW SEDAPSDQSD TSESDVDLGD GYIMR                               515

SEQ ID NO: 15          moltype = AA  length = 575
FEATURE                Location/Qualifiers
source                 1..575
                       mol_type = protein
                       organism = Homo sapiens
SEQUENCE: 15
MWSLLLCGLS IALPLSVTAD GCKDIFMKNE ILSASQPFAF NCTFPPITSG EVSVTWYKNS     60
SKIPVSKIIQ SRIHQDETWI LFLPMEWGDS GVYQCVIKGR DSCHRIHVNL TVFEKHWCDT    120
SIGGLPNLSD EYKQILHLGK DDSLTCHLHF PKSCVLGPIK WYKDCNEIKG ERFTVLETRL    180
LVSNVSAEDR GNYACQAILT HSGKQYEVLN GITVSITERA GYGGSVPKII YPKNHSIEVQ    240
LGTTLIVDCN VTDTKDNTNL RCWRVNNTLV DDYYDESKRI REGVETHVSF REHNLYTVNI    300
TFLEVKMEDY GLPFMCHAGV STAYIILQLP APDFRAYLIG GLIALVAVAV SVVYIYNIFK    360
IDIVLWYRSA FHSTETIVDG KLYDAYVLYP KPHKESQRHA VDALVLNILP EVLERQCGYK    420
LFIFGRDEFP GQAVANVIDE NVKLCRRLIV IVVPESLGFG LLKNLSEEQI AVYSALIQDG    480
MKVILIELEK IEDYTVMPES IQYIKQKHGA IRWHGDFTEQ SQCMKTKFWK TVRYHMPPRR    540
CRPFPPVQLL QHTPCYRTAG PELGSRRKKC TLTTG                               575

SEQ ID NO: 16          moltype = AA  length = 786
FEATURE                Location/Qualifiers
source                 1..786
                       mol_type = protein
                       organism = Homo sapiens
SEQUENCE: 16
MTSIFHFAII FMLILQIRIQ LSEESEFLVD RSKNGLIHVP KDLSQKTTIL NISQNYISEL     60
WTSDILSLSK LRILIISHNR IQYLDISVFK FNQELEYLDL SHNKLVKISC HPTVNLKHLD    120
LSFNAFDALP ICKEFGNMSQ LKFLGLSTTH LEKSSVLPIA HLNISKVLLV LGETYGEKED    180
PEGLQDFNTE SLHIVFPTNK EFHFILDVSV KTVANLELSN IKCVLEDNKC SYFLSILAKL    240
QTNPKLSNLT LNNIETTWNS FIRILQLVWH TTVWYFSISN VKLQGQLDFR DFDYSGTSLK    300
ALSIHQVVSD VFGFPQSYIY EIFSNMNIKN FTVSGTRMVH MLCPSKISPF LHLDFSNNLL    360
TDTVFENCGH LTELETLILQ MNQLKELSKI AEMTTQMKSL QQLDISQNSV SYDEKKGDCS    420
WTKSLLSLNM SSNILTDTIF RCLPPRIKVL DLHSNKIKSI PKQVVKLEAL QELNVAFNSL    480
TDLPGCGSFS SLSVLIIDHN SVSHPSADFF QSCQKMRSIK AGDNPFQCTC ELGEFVKNID    540
QVSSEVLEGW PDSYKCDYPE SYRGTLLKDF HMSELSCNIT LLIVTIVATM LVLAVTVTSL    600
CSYLLDLPWYL RMVCQWTQTR RRARNIPLEE LQRNLQFHAF ISYGHDSFW VKNELLPNLE    660
KEGMQICLHE RNFVPGKSIV ENIITCIEKS YKSIFVLSPN FVQSEWCHYE LYFAHHNLFH    720
EGSNSLILIL LEPIPQYSIP SSYHKLKSLM ARRTYLEWPK EKSKRGLFWA NLRAAINIKL    780
TEQAKK                                                               786

SEQ ID NO: 17          moltype = AA  length = 784
FEATURE                Location/Qualifiers
source                 1..784
                       mol_type = protein
                       organism = Homo sapiens
SEQUENCE: 17
MPHTLWMVWV LGVIISLSKE ESSNQASLSC DRNGICKGSS GSLNSIPSGL TEAVKSLDLS     60
NNRITYISNS DLQRCVNLQA LVLTSNGINT IEEDSFSSLG SLEHLDLSYN YLSNLSSSWF    120
KPLSSLTFLN LLGNPYKTLG ETSLFSHLTK LQILRVGNMD TFTKIQRKDF AGLTFLEELE    180
IDASDLQSYE PKSLKSIQNV SHLILHMKQH ILLLEIFVDV TSSVECLELR DTDLDTFHFS    240
ELSTGETNSL IKKFTFRNVK ITDESLFQVM KLLNQISGLL ELEFDDCTLN GVGNFRASDN    300
DRVIDPGKVE TLTIRRLHIP RFYLFYDLST LYSLTERVKR ITVENSKVFL VPCLLSQHLK    360
SLEYLDLSEN LMVEEYLKNS ACEDAWPSLQ TLILRQNHLA SLEKTGETLL TLKNLTNIDI    420
SKNSFHSMPE TCQWPEKMKY LNLSSTRIHS VTGCIPKTLE ILDVSNNNLN LFSLNLPQLK    480
ELYISRNKLM TLPDASLLPM LLVLKISRNA ITTFSKEQLD SFHTLKTLEA GGNNFICSCE    540
FLSFTQEQQA LAKVLIDWPA NYLCDSPSHV RGQQVQDVRL SVSECHRTAL VSGMCCALFL    600
```

```
LILLLTGVLCH  RFHGLWYMKM  MWAWLQAKRK  PRKAPSRNIC  YDAFVSYSER  DAYWVENLMV    660
QELENFNPPF  KLCLHKRDFI  PGKWIIDNII  DSIEKSHKTV  FVLSENFVKS  EWCKYELDFS    720
HFRLFDENND  AAILILLEPI  EKKAIPQRFC  KLRKIMNTKT  YLEWPMDEAQ  REGFWVNLRA    780
AIKS                                                                     784

SEQ ID NO: 18            moltype = AA  length = 904
FEATURE                  Location/Qualifiers
source                   1..904
                         mol_type = protein
                         organism = Homo sapiens
SEQUENCE: 18
MRQTLPCIYF  WGGLLPFGML  CASSTTKCTV  SHEVADCSHL  KLTQVPDDLP  TNITVLNLTH     60
NQLRRLPAAN  FTRYSQLTSL  DVGFNTISKL  EPELCQKLPM  LKVLNLQHNE  LSQLSDKTFA    120
FCTNLTELHL  MSNSIQKIKN  NPFVKQKNLI  TLDLSHNGLS  STKLGTQVQL  ENLQELLLSN    180
NKIQALKSEE  LDIFANSSLK  KLELSSNQIK  EFSPGCFHAI  GRLFGLFLNN  VQLGPSLTEK    240
LCLELANTSI  RNLSLSNSQL  STTSNTTFLG  LKWTNLTMLD  LSYNNLNVVG  NDSFAWLPQL    300
EYFFLEYNNI  QHLFSHSLHG  LFNVRYLNLK  RSFTKQSISL  ASLPKIDDFS  FQWLKCLEHL    360
NMEDNDIPGI  KSNMFTGLIN  LKYLSLSNSF  TSLRTLTNET  FVSLAHSPLH  ILNLTKNKIS    420
KIESDAFSWL  GHLEVLDLGL  NEIGQELTGQ  EWRGLENIFE  IYLSYNKYLQ  LTRNSFALVP    480
SLQRLMLRRV  ALKNVDSSPS  PFQPLRNLTI  LDLSNNNIAN  INDDMLEGLE  KLEILDLQHN    540
NLARLWKHAN  PGGPIYFLKG  LSHLHILNLE  SNGFDEIPVE  VFKDLFELKI  IDLGLNNNLNT    600
LPASVFMNQV  SLKSLNLQKN  LITSVEKKVF  GPAFRNLTEL  DMRFNPFDCT  CESIAWFVNW    660
INETHTNIPE  LSSHYLCNTP  PHYHGFPVRL  FDTSSCKDSA  PFELFFMINT  SILLIFIFIV    720
LLIHFEGWRI  SFYWNVSVHR  VLGFKEIDRQ  TEQFEYAAYI  IHAYKDKDWV  WEHFSSMEKE    780
DQSLKFCLEE  RDFEAGVFEL  EAIVNSIKRS  RKIIFVITHH  LLKDPLCKRF  KVHHAVQQAI    840
EQNLDSIILV  FLEEIPDYKL  NHALCLRRGM  FKSHCILNWP  VQKERIGAFR  HKLQVALGSK    900
NSVH                                                                     904

SEQ ID NO: 19            moltype = AA  length = 839
FEATURE                  Location/Qualifiers
source                   1..839
                         mol_type = protein
                         organism = Homo sapiens
SEQUENCE: 19
MMSASRLAGT  LIPAMAFLSC  VRPESWEPCV  EVVPNITYQC  MELNFYKIPD  NLPFSTKNLD     60
LSFNPLRHLG  SYSFFSFPEL  QVLDLSRCEI  QTIEDGAYQS  LSHLSTLILT  GNPIQSLALG    120
AFSGLSSLQK  LVAVETNLAS  LENFPIGHLK  TLKELNVAHN  LIQSFKLPEY  FSNLTNLEHL    180
DLSSNKIQSI  YCTDLRVLHQ  MPLLNLSLDL  SLNPMNFIQP  GAFKEIRLHK  LTLRNNFDSL    240
NVMKTCIQGL  AGLEVHRLVL  GEFRNEGNLE  KFDKSALEGL  CNLTIEEFRL  AYLDYYLDDI    300
IDLFNCLTNV  SSFSLVSVTI  ERVKDFSYNF  GWQHLELVNC  KFGQFPTLKL  KSLKRLTFTS    360
NKGGNAFSEV  DLPSLEFLDL  SRNGLSFKGC  CSQSDFGTTS  LKYLDLSFNG  VITMSSNFLG    420
LEQLEHLDFQ  HSNLKQMSEF  SVFLSLRNLI  YLDISHTHTR  VAFNGIFNGL  SSLEVLKMAG    480
NSFQENFLPD  IFTELRNLTF  LDLSQCQLEQ  LSPTAFNSLS  SLQVLNMSHN  NFFSLDTFPY    540
KCLNSLQVLD  YSLNHIMTSK  KQELQHFPSS  LAFLNLTQND  FACTCEHQSF  LQWIKDQRQL    600
LVEVERMECA  TPSDKQGMPV  LSLNITCQMN  KTIIGVSVLS  VLVVSVVAVL  VYKFYPHLML    660
LAGCIKYGRG  ENIYDAFVIY  SSQDEDWVRN  ELVKNLEEGV  PPFQLCLHYR  DFIPGVAIAA    720
NIIHEGPHKS  RKVIVVVSQH  FIQSRWCIFE  YEIAQTWQFL  SSRAGIIFIV  LQKVEKTLLR    780
QQVELYRLLS  RNTYLEWEDS  VLGRHIFWRR  LRKALLDGKS  WNPEGTVGTG  CNWQEATSI     839

SEQ ID NO: 20            moltype = AA  length = 858
FEATURE                  Location/Qualifiers
source                   1..858
                         mol_type = protein
                         organism = Homo sapiens
SEQUENCE: 20
MGDHLDLLLG  VVLMAGPVFG  IPSCSFDGRI  AFYRFCNLTQ  VPQVLNTTER  LLLSFNYIRT     60
VTASSPPFLE  QLQLLELGSQ  YTPLTIDKEA  FRNLPNLRIL  DLGSSKIYFL  HPDAFQGLFH    120
LFELRLYFCG  LSDAVLKDGY  FRNLKALTRL  DLSKNQIRSL  YLHPSFGKLN  SLKSIDFSSN    180
QIFLVCEHEL  EPLQGKTLSF  FSLAANSLYS  RVSVDWGKCM  NPFRNMVLEI  LDVSGNGWTV    240
DITGNFSNAI  SKSQAFSLIL  AHHIMGAGFG  FHNIKDPDQN  TFAGLARSSV  RHLDLSHGFV    300
FSLNSRVFET  LKDKLVLNLA  YNKINKIADE  AFYGLDNLQV  LNLSYNLLGE  LYSSNFYGLP    360
KVAYIDLQKN  HIAIIQDQTF  KFLEKLQTLD  LRDNALTTIH  FIPSIPDIFL  SGNKLVTLPK    420
INLTANLIHL  SENRLENLDI  LYFLLRVPHL  QILILNQNRF  SSCSGDQTPS  ENPSLEQLFL    480
GENMLQLAWE  TELCWDVFEG  LSHLQVLYLN  HNYLNSLPPG  VFSHLTALRG  LSLNSNRLTV    540
LSHNDLPANL  EILDISRNQL  LAPNPDVFVS  LSVLDITHNK  FICECELSTF  INWLNHTNVT    600
IAGPPADIYC  VYPDSFSGVS  LFSLSTEGCD  EEEVLKSLKF  SLFIVCTVTL  TLFLMTILTV    660
TKFRGFCFIC  YKTAQRLVFK  DHPQGTEPDM  YKYDAYLCFS  SKDFTWVQNA  LLKHLDTQYS    720
DQNRFNLCFE  ERDFVPGENR  IANIQDAIWN  SRKIVCLVSR  HPLRDGWCLE  APSYAQGRCL    780
SDLNSALIMV  VVGSLSQYQL  MKHQSIRGFV  QKQQYLRWPE  DFQDVGWFLH  KLSQQILKKE    840
KEKKKDNNIP  LQTVATIS                                                     858

SEQ ID NO: 21            moltype = AA  length = 796
FEATURE                  Location/Qualifiers
source                   1..796
                         mol_type = protein
                         organism = Homo sapiens
SEQUENCE: 21
MTKDKEPIVK  SFHFVCLMII  IVGTRIQFSD  GNEFAVDKSK  RGLIHVPKDL  PLKTKVLDMS     60
QNYIAELQVS  DMSFSLSELTV  LRLSHNRIQL  LDLSVFKFNQ  DLEYLDLSHN  QLQKISCHPI    120
```

```
VSFRHLDLSF NDFKALPICK EFGNLSQLNF LGLSAMKLQK LDLLPIAHLH LSYILLDLRN    180
YYIKENETES LQILNAKTLH LVFHPTSLFA IQVNISVNTL GCLQLTNIKL NDDNCQVFIK    240
FLSELTRGST LLNFTLNHIE TTWKCLVRVF QFLWPKPVEY LNIYNLTIIE SIREEDFTYS    300
KTTLKALTIE HITNQVFLFS QTALYTVFSE MNIMMLTISD TPFIHMLCPH APSTFKFLNF    360
TQNVFTDSIF EKCSTLVKLE TLILQKNGLK DLFKVGLMTK DMPSLEILDV SWNSLESGRH    420
KENCTWVESI VVLNLSSNML TDSVFRCLPP RIKVLDLHSN KIKSVPKQVV KLEALQELNV    480
AFNSLTDLPG CGSFSSLSVL IIDHNSVSHP SADFFQSCQK MRSIKAGDNP FQCTCELREF    540
VKNIDQVSSE VLEGWPDSYK CDYPESYRGS PLKDFHMSEL SCNITLLIVT IGATMLVLAV    600
TVTSLCIYLD LPWYLRMVCQ WTQTRRRARN IPLEELQRNL QPHAFISYSE HDSAWVKSEL    660
VPYLEKEDIQ ICLHERNFVP GKSIVENIIK CIEKSYKSIF VLSPNFVQSE WCHYELYFAH    720
HNLFHEGSNN LILILLEPIP QNSIPNKYHK LKALMTQRTY LQWPKEKSKR GLFWANIRAA    780
FNMKLTLVTE NNDVKS                                                   796

SEQ ID NO: 22           moltype = AA  length = 1049
FEATURE                 Location/Qualifiers
source                  1..1049
                        mol_type = protein
                        organism = Homo sapiens
SEQUENCE: 22
MVFPMWTLKR QILILFNIIL ISKLLGARWF PKTLPCDVTL DVPKNHVIVD CTDKHLTEIP     60
GGIPTNTTNL TLTINHIPDI SPASFHRLDH LVEIDFRCNC VPIPLGSKNN MCIKRLQIKP    120
RSFSGLTYLK SLYLDGNQLL EIPQGLPPSL QLLSLEANNI FSIRKENLTE LANIEILYLG    180
QNCYYRNPCY VSYSIEKDAF LNLTKLKVLS LKDNNVTAVP TVLPSTLTEL YLYNNMIAKI    240
QEDDFNNLNQ LQILDLSGNC PRCYNAPFPC APCKNNSPLQ IPVNAFDALT ELKVLRLHSN    300
SLQHVPPRWF KNINKLQELD LSQNFLAKEI GDAKFLHFLP SLIQLDLSFN FELQVYRASM    360
NLSQAFSSLK SLKILRIRGY VFKELKSFNL SPLHNLQNLE VLDLGTNFIK IANLSMFKQF    420
KRLKVIDLSV NKISPSGDSS EVGFCSNART SVESYEPQVL EQLHYFRYDK YARSCRFKNK    480
EASFMSVNES CYKYGQTLDL SKNSIFFVKS SDFQHLSFLK CLNLSGNLIS QTLNGSEFQP    540
LAELRYLDFS NNRLDLLHST AFEELHKLEV LDISSNSHYF QSEGITHMLN FTKNLKVLQK    600
LMMNDNDISS STSRTMESES LRTLEFRGNH LDVLWREGDN RYLQLFKNLL KLEELDISKN    660
SLSFLPSGVF DGMPPNLKNL SLAKNGLKSF SWKKLQCLKN LETLDLSHNQ LTTVPERLSN    720
CSRSLKNLIL KNNQIRSLTK YFLQDAFQLR YLDLSSNKIQ MIQKTSFPEN VLNNLKMLLL    780
HHNRFLCTCD AVWFVWWVNH TEVTIPYLAT DVTCVGPGAH KGQSVISLDL YTCELDLTNL    840
ILFSLSISVS LFLMVMMTAS HLYFWDVWYI YHFCKAKIKG YQRLISPDCC YDAFIVYDTK    900
DPAVTEWVLA ELVAKLEDPR EKHFNLCLEE RDWLPGQPVL ENLSQSIQLS KKTVFVMTDK    960
YAKTENFKIA FYLSHQRLMD EKVDVIILIF LEKPFQKSKF LQLRKRLCGS SVLEWPTNPQ   1020
AHPYFWQCLK NALATDNHVA YSQVFKETV                                    1049

SEQ ID NO: 23           moltype = AA  length = 1041
FEATURE                 Location/Qualifiers
source                  1..1041
                        mol_type = protein
                        organism = Homo sapiens
SEQUENCE: 23
MENMFLQSSM LTCIFLLISG SCELCAEENF SRSYPCDEKK QNDSVIAECS NRRLQEVPQT     60
VGKYVTELDL SDNFITHITN ESFQGLQNLT KINLNHNPNV QHQNGNPGIQ SNGLNITDGA    120
FLNLKNLREL LLEDNQLPQI PSGLPESLTE LSLIQNNIYN ITKEGISRLI NLKNLYAWN     180
CYFNKVCEKT NIEDGVFETL TNLELLSLSF NSLSHVPPKL PSSLRKLFLS NTQIKYISEE    240
DFKGLINLTL LDLSGNCPRC FNAPFPCVPC DGGASINIDR FAFQNLTQLR YLNLSSTSLR    300
KINAAWFKNM PHLKVLDLEF NYLVGEIASG AFLTMLPRLE ILDLSFNYIK GSYPQHINIS    360
RNFSKLLSLR ALHLRGYVFQ ELREDDFQPL MQLPNLSTIN LGINFIKQID FKLFQNFSNL    420
EIIYLSENRI SPLVKDTRQS YANSSSFQRH IRKRRSTDFE FDPHSNFYHF TRPLIKPQCA    480
AYGKALDLSL NSIFFIGPNQ FENLPDIACL NLSANSNAQV LSGTEFSAIP HVKYLDLTNN    540
RLDFDNASAL TELSDLEVLD LSYNSHYFRI AGVTHHLEFI QNFTNLKVLN LSHNNIYTLT    600
DKYNLESKSL VELVFSGNRL DILWNDDDNR YISIFKGLKN LTRLDLSLNR LKHIPNEAFL    660
NLPASLTELH INDNMLKFFN WTLLQQFPRL ELLDLRGNKL LFLTDSLSDF TSSLRTLLLS    720
HNRISHLPSG FLSEVSSLKH LDLSSNLLKT INKSALETKT TTKLSMLELH GNPFECTCDI    780
GDFRRWMDEH LNVKIPRLVD VICASPGDQR GKSIVSLELT TCVSDVTAVI LFFFTFFITT    840
MVMLAALAHH LFYWDVWFIY NVCLAKVKGY RSLSTSQYTY DAYISYDTKD ASVTDWVINE    900
LRYHLEESRD KNVLLCLEER DWDPGLAIID NLMQSINQSK KTVFVLTKKY AKSWNFKTAF    960
YLALQRLMDE NMDVIIFILL EPVLQHSQYL RLRQRICKSS ILQWPDNPKA EGLFWQTLRN   1020
VVLTENDSRY NNMYVDSIKQ Y                                            1041

SEQ ID NO: 24           moltype = AA  length = 1032
FEATURE                 Location/Qualifiers
source                  1..1032
                        mol_type = protein
                        organism = Homo sapiens
SEQUENCE: 24
MGFCRSALHP LSLLVQAIML AMTLALGTLP AFLPCELQPH GLVNCNWLFL KSVPHFSMAA     60
PRGNVTSLSL SSNRIHHLHD SDFAHLPSLR HLNLKWNCPP VGLSPMHFPC HMTIEPSTFL    120
AVPTLEELNL SYNNIMTVPA LPKSLISLSL SHTNILMLDS ASLAGLHALR FLFMDGNCYY    180
KNPCRQALEV APGALLGLGN LTHLSLKYNN LTVVPRNLPS SLEYLLLSYN RIVKLAPEDL    240
ANLTALRVLD VGGNCRRCDH APNPCMECPR HFPQLHPDTF SHLSRLEGLV LKDSSLSWLN    300
ASWFRGLGNL RVLDLSENFL YKCITKTKAF QGLTQLRKLN LSFNYQKRVS FAHLSLAPSF    360
GSLVALKELD MHGIFFRSLD ETTLRPLARL PMLQTLRLQM NFINQAQLGI FRAFPGLRYV    420
DLSDNRISGA SELTATMGEA DGGEKVWLQP GDLAPAVPDT PSSEDFRPNC STLNFTLDLS    480
RNNLVTVQPE MFAQLSHLQC LRLSHNCISQ AVNGSQFLPL TGLQVLDLSH NKLDLYHEHS    540
FTELPRLEAL DLSYNSQPFG MQGVGHNFSF VAHLRTLRHL SLAHNNIHSQ VSQQLCSTSL    600
```

```
RALDFSGNAL GHMWAEGDLY LHFFQGLSGL IWLDLSQNRL HTLLPQTLRN LPKSLQVLRL   660
RDNYLAFFKW WSLHFLPKLE VLDLAGNQLK ALTNGSLPAG TRLRRLDVSC NSISFVAPGF   720
FSKAKELREL NLSANALKTV DHSWFGPLAS ALQILDVSAN PLHCACGAAF MDFLLEVQAA   780
VPGLPSRVKC GSPGQLQGLS IFAQDLRLCL DEALSWDCFA LSLLAVALGL GVPMLHHLCG   840
WDLWYCFHLC LAWLPWRGRQ SGRDEDALPY DAFVVFDKTQ SAVADWVYNE LRGQLEECRG   900
RWALRLCLEE RDWLPGKTLF ENLWASVYGS RKTLFVLAHT DRVSGLLRAS FLLAQQRLLE   960
DRKDVVVLVI LSPDGRRSRY VRLRQRLCRQ SVLLWPHQPS GQRSFWAQLG MALTRDNHHF  1020
YNRNFCQGPT AE                                                     1032

SEQ ID NO: 25              moltype = AA  length = 811
FEATURE                    Location/Qualifiers
source                     1..811
                           mol_type = protein
                           organism = Homo sapiens
SEQUENCE: 25
MRLIRNIYIF CSIVMTAEGD APELPEEREL MTNCSNMSLR KVPADLTPAT TTLDLSYNLL    60
FQLQSSDFHS VSKLRVLILC HNRIQQLDLK TFEFNKELRY LDLSNNRLKS VTWYLLAGLR   120
YLDLSFNDFD TMPICEEAGN MSHLEILGLS GAKIQKSDFQ KIAHLHLNTV FLGFRTLPHY   180
EEGSLPILNT TKLHIVLPMD TNFWVLLRDG IKTSKILEMT NIDGKSQFVS YEMQRNLSLE   240
NAKTSVLLLN KVDLLWDDLF LILQFVWHTS VEHFQIRNVT FGGKAYLDHN SFDYSNTVMR   300
TIKLEHVHFR VFYIQQDKIY LLLTKMDIEN LTISNAQMPH MLFPNYPTKF QYLNFANNIL   360
TDELFKRTIQ LPHLKTLILN GNKLETLSLV SCFANNTLKE HLDLSQNLLQ HKNDENCSWP   420
ETVVNMNLSY NKLSDSVFRC LPKSIQILDL NNNQIQTVPK ETIHLMALRE LNIAFNFLTD   480
LPGCSHFSRL SVLNIEMNFI LSPSLDFVQS CQEVKTLNAG RNPFRCTCEL KNFIQLETYS   540
EVMMVGWSDS YTCEYPLNLR GTRLKDVHLH ELSCNTALLI VTIVVIMLVL GLAVAFCCLH   600
FDLPWYLRML GQCTQTWHRV RKTTQEQLKR NVRFHAFISY SEHDSLWVKN ELIPNLEKED   660
GSILICLYES YFDPGKSISE NIVSFIEKSY KSIFVLSPNF VQNEWCHYEF YFAHHNLFHE   720
NSDHIILILL EPIPFYCIPT RYHKLKALLE KKAYLEWPKD RRKCGLFWAN LRAAINVNVL   780
ATREMYELQT FTELNEESRG STISLMRTDC L                                 811

SEQ ID NO: 26              moltype = AA  length = 243
FEATURE                    Location/Qualifiers
REGION                     1..243
                           note = Made in Lab - Synthesized fusion protein
source                     1..243
                           mol_type = protein
                           organism = synthetic construct
SEQUENCE: 26
MEAAVAAPRP RLLLLVLAAA AAAAAALLPG ATALQCFCHL CTKDNFTCVT DGLCFVSVTE    60
TTDKVIHNSM CIAEIDLIPR DRPFVCAPSS KTGSVTTTYC CNQDHCNKIE LPTTVKSSPG   120
LGPVELWLIF FASLGSFLSI LLVGVLGYLG LNRAARHLCP PLPTPCASSA IEFPGGKETW   180
QWINPVDFQE EASLQEALVV EMSWDKGERT EPLEKTELPE GAPELALDTE LSLEDGDRCK   240
AKM                                                                243

SEQ ID NO: 27              moltype = AA  length = 406
FEATURE                    Location/Qualifiers
REGION                     1..406
                           note = Made in Lab - synthesized fusion protein
source                     1..406
                           mol_type = protein
                           organism = synthetic construct
SEQUENCE: 27
MGRGLLRGLW PLHIVLWTRI ASTIPPHVQK SVNNDMIVTD NNGAVKFPQL CKFCDVRFST    60
CDNQKSCMSN CSITSICEKP QEVCAVVWRK NDENITLETV CHDPKLPYHD FILEDAASPK   120
CIMKEKKKPG ETFFMCSCSS DECNDNIIFS EEYNTSNPDL LLVIFQWMAF VAPSICIAII   180
MVGIFSTHYF QQKVFVLLAA LRPQWCSREI PDPANSTCAK KYPIAEEKTQ LPLDRLLIDW   240
PTPEDPEPLV ISEVLHQVTP VFRHPPCSNW PQREKGIQGH QASEKDMMHS ASSPPPPRAL   300
QAESRQLVDL YKVLESRGSD PKPENPACPW TVLPAGDLPT HDGYLPSNID DLPSHEAPLA   360
DSLEELEPQH ISLSVFPSSS LHPLTFSCGD KLTLDQLKMR CDSLML                 406

SEQ ID NO: 28              moltype = AA  length = 671
FEATURE                    Location/Qualifiers
REGION                     1..671
                           note = Made in Lab - Synthesized fusion protein
source                     1..671
                           mol_type = protein
                           organism = synthetic construct
SEQUENCE: 28
MGRGLLRGLW PLHIVLWTRI ASTIPPHVQK SVNNDMIVTD NNGAVKFPQL CKFCDVRFST    60
CDNQKSCMSN CSITSICEKP QEVCAVVWRK NDENITLETV CHDPKLPYHD FILEDAASPK   120
CIMKEKKKPG ETFFMCSCSS DECNDNIIFS EEYNTSNPDL LLVIFQWMAF VAPSICIAII   180
MVGIFSTHYF QQKVFVLLAA LRPQWCSREI PDPANSTCAK KYPIAEEKTQ LPLDRLLIDW   240
PTPEDPEPLV ISEVLHQVTP VFRHPPCSNW PQREKGIQGH QASEKDMMHS ASSPPPPRAL   300
QAESRQLVDL YKVLESRGSD PKPENPACPW TVLPAGDLPT HDGYLPSNID DLPSHEAPLA   360
DSLEELEPQH ISLSVFPSSS LHPLTFSCGD KLTLDQLKMR CDSLMLGSGA TNFSLLKQAG   420
DVEENPGPME AAVAAPRPRL LLLVLAAAAA AAAALLPGAT ALQCFCHLCT KDNFTCVTDG   480
LCFVSVTETT DKVIHNSMCI AEIDLIPRDR PFVCAPSSKT GSVTTTYCCN QDHCNKIELP   540
TTVKSSPGLG PVELWLIFFA SLGSFLSILL VGVLGYLGLN RAARHLCPPL PTPCASSAIE   600
FPGGKETWQW INPVDFQEEA SLQEALVVEM SWDKGERTEP LEKTELPEGA PELALDTELS   660
```

LEDGDRCKAK M                                                                     671

SEQ ID NO: 29          moltype = AA  length = 1183
FEATURE                Location/Qualifiers
REGION                 1..1183
                       note = Made in Lab - Synthesized fusion protein
source                 1..1183
                       mol_type = protein
                       organism = synthetic construct
SEQUENCE: 29
MALPVTALLL PLALLLHAAR PQSALTQPPS ASGTPGQRVT ISCSGSSSNI GSNYVYWYQQ      60
LPGTAPKLLI YRNNQRPSGV PDRFSGSKSG TSASLAISGL RSEDEADYYC AAWDDSLSGY     120
VFGTGTKVTV LGGGGSGGG GSGGGGSQMQ LVQSGAEVKK PGASVKVSCK ASGYTFSRYY      180
IHWVRQAPGQ GLEWMGLINP GGGSTNYAQK FQGRVTMTRD TSTNTVYLEL SSLRSDDTAV     240
YYCARDYGTI DARRFDFWGQ GTLVTVSSTT TPAPRPPTPA PTIASQPLSL RPEACRPAAG     300
GAVHTRGLDF ACDIYIWAPL AGTCGVLLLS LVITLYCKRG RKKLLYIFKQ PFMRPVQTTQ     360
EEDGCSCRFP EEEEGGCELR VKFSRSADAP AYQQGQNQLY NELNLGRREE YDVLDKRRGR     420
DPEMGGKPRR KNPQEGLYNE LQKDKMAEAY SEIGMKGERR RGKGHDGLYQ GLSTATKDTY     480
DALHMQALPP RGSGEGRGSL LTCGDVEENP GPMGRGLLRG LWPLHIVLWT RIASTIPPHV     540
QKSVNNDMIV TDNNGAVKFP QLCKFCDVRF STCDNQKSCM SNCSITSICE KPQEVCVAVW     600
RKNDENITLE TVCHDPKLPY HDFILEDAAS PKCIMKEKKK PGETFFMCSC SSDECNDNII     660
FSEEYNTSNP DLLLVIFQWM AFVAPSICIA IIMVGIFSTH YFQQKVFVLL AALRPQWCSR     720
EIPDPANSTC AKKYPIAEEK TQLPLDRLLI DWPTPEDPEP LVISEVLHQV TPVFRHPPCS     780
NWPQREKGIQ GHQASEKDMM HSASSPPPPR ALQAESRQLV DLYKVLESRG SDPKPENPAC     840
PWTVLPAGDL PTHDGYLPSN IDDLPSHEAP LADSLEELEP QHISLSVFPS SSLHPLTFSC     900
GDKLTLDQLK MRCDSLMLGS GATNFSLLKQ AGDVEENPGP MEAAVAAPRP RLLLLVLAAA     960
AAAAAALLPG ATALQCFCHL CTKDNFTCVT DGLCFVSVTE TTDKVIHNSM CIAEIDLIPR    1020
DRPFVCAPSS KTGSVTTTYC CNQDHCNKIE LPTTVKSSPG LGPVELWLIF FASLGSFLSI    1080
LLVGVLGYLG LNRAARHLCP PLPTPCASSA IEFPGGKETW QWINPVDFQE EASLQEALVV    1140
EMSWDKGERT EPLEKTELPE GAPELALDTE LSLEDGDRCK AKM                     1183

SEQ ID NO: 30          moltype = AA  length = 937
FEATURE                Location/Qualifiers
REGION                 1..937
                       note = Made in Lab - Synthesized fusion protein
VARIANT                22
                       note = Xaa can be any naturally occurring amino acid
source                 1..937
                       mol_type = protein
                       organism = synthetic construct
SEQUENCE: 30
MALPVTALLL PLALLLHAAR PXTTTPAPRP PTPAPTIASQ PLSLRPEACR PAAGGAVHTR      60
GLDFACDIYI WAPLAGTCGV LLLSLVITLY CKRGRKKLLY IFKQPFMRPV QTTQEEDGCS     120
CRFPEEEEGG CELRVKFSRS ADAPAYQQGQ NQLYNELNLG RREEYDVLDK RRGRDPEMGG     180
KPRRKNPQEG LYNELQKDKM AEAYSEIGMK GERRRGKGHD GLYQGLSTAT KDTYDALHMQ     240
ALPPRGSGEG RGSLLTCGDV EENPGPMGRG LLRGLWPLHI VLWTRIASTI PPHVQKSVNN     300
DMIVTDNNGA VKFPQLCKFC DVRFSTCDNQ KSCMSNCSIT SICEKPQEVC VAVWRKNDEN     360
ITLETVCHDP KLPYHDFILE DAASPKCIMK EKKKPGETFF MCSCSSDECN DNIIFSEEYN     420
TSNPDLLLVI FQWMAFVAPS ICIAIIMVGI FSTHYFQQKV FVLLAALRPQ WCSREIPDPA     480
NSTCAKKYPI AEEKTQLPLD RLLIDWPTPE DPEPLVISEV LHQVTPVFRH PPCSNWPQRE     540
KGIQGHQASE KDMMHSASSP PPPRALQAES RQLVDLYKVL ESRGSDPKPE NPACPWTVLP     600
AGDLPTHDGY LPSNIDDLPS HEAPLADSLE ELEPQHISLS VFPSSSLHPL TFSCGDKLTL     660
DQLKMRCDSL MLGSGATNFS LLKQAGDVEE NPGPMEAAVA APRPRLLLLV LAAAAAAAAA     720
LLPGATALQC FCHLCTKDNF TCVTDGLCFV SVTETTDKVI HNSMCIAEID LIPRDRPFVC     780
APSSKTGSVT TTYCCNQDHC NKIELPTTVK SSPGLGPVEL WLIFFASLGS FLSILLVGVL     840
GYLGLNRAAR HLCPPLPTPC ASSAIEFPGG KETWQWINPV DFQEEASLQE ALVVEMSWDK     900
GERTEPLEKT ELPEGAPELA LDTELSLEDG DRCKAKM                             937

SEQ ID NO: 31          moltype = AA  length = 233
FEATURE                Location/Qualifiers
REGION                 1..233
                       note = Made in Lab - Synthesized fusion protein
source                 1..233
                       mol_type = protein
                       organism = synthetic construct
SEQUENCE: 31
MEAAVAAPRP RLLLLVLAAA AAAAAALLPG ATALQCFCHL CTKDNFTCVT DGLCFVSVTE      60
TTDKVIHNSM CIAEIDLIPR DRPFVCAPSS KTGSVTTTYC CNQDHCNKIE LPTTVKSSPG     120
LGPVELVVIS VGSMGLIISL LCVYFWLERT MPRIPTLKNL EDLVTEYHGN FSAWSGVSKG     180
LAESLQPDYS ERLCLVSEIP PKGGALGEGP GASPCNQHSP YWAPPCYTLK PET            233

SEQ ID NO: 32          moltype = AA  length = 386
FEATURE                Location/Qualifiers
REGION                 1..386
                       note = Made in Lab - Synthesized fusion protein
source                 1..386
                       mol_type = protein
                       organism = synthetic construct
SEQUENCE: 32

```
MGRGLLRGLW PLHIVLWTRI ASTIPPHVQK SVNNDMIVTD NNGAVKFPQL CKFCDVRFST    60
CDNQKSCMSN CSITSICEKP QEVCVAVWRK NDENITLETV CHDPKLPYHD FILEDAASPK   120
CIMKEKKKPG ETFFMCSCSS DECNDNIIFS EEYNTSNPDL LLVIFQPILL TISILSFFSV   180
ALLVILACVL WKKRIKPIVW PSLPDHKKTL EHLCKKPRKN LNVSFNPESF LDCQIHRVDD   240
IQARDEVEGF LQDTFPQQLE ESEKQRLGGD VQSPNCPSED VVITPESFGR DSSLTCLAGN   300
VSACDAPILS SSRSLDCRES GKNGPHVYQD LLLSLGTTNS TLPPPFSLQS GILTLNPVAQ   360
GQPILTSLGS NQEEAYVTMS SFYQNQ                                       386

SEQ ID NO: 33           moltype = AA  length = 641
FEATURE                 Location/Qualifiers
REGION                  1..641
                        note = Made in Lab - Synthesized fusion protein
source                  1..641
                        mol_type = protein
                        organism = synthetic construct
SEQUENCE: 33
MGRGLLRGLW PLHIVLWTRI ASTIPPHVQK SVNNDMIVTD NNGAVKFPQL CKFCDVRFST    60
CDNQKSCMSN CSITSICEKP QEVCVAVWRK NDENITLETV CHDPKLPYHD FILEDAASPK   120
CIMKEKKKPG ETFFMCSCSS DECNDNIIFS EEYNTSNPDL LLVIFQPILL TISILSFFSV   180
ALLVILACVL WKKRIKPIVW PSLPDHKKTL EHLCKKPRKN LNVSFNPESF LDCQIHRVDD   240
IQARDEVEGF LQDTFPQQLE ESEKQRLGGD VQSPNCPSED VVITPESFGR DSSLTCLAGN   300
VSACDAPILS SSRSLDCRES GKNGPHVYQD LLLSLGTTNS TLPPPFSLQS GILTLNPVAQ   360
GQPILTSLGS NQEEAYVTMS SFYQNQGSGA TNFSLLKQAG DVEENPGPME AAVAAPRPRL   420
LLLVLAAAAA AAAALLPGAT ALQCFCHLCT KDNFTCVTDG LCFVSVTETT DKVIHNSMCI   480
AEIDLIPRDR PFVCAPSSKT GSVTTTYCCN QDHCNKIELP TTVKSSPGLG PVELVVISVG   540
SMGLIISLLC VYFWLERTMP RIPTLKNLED LVTEYHGNFS AWSGVSKGLA ESLQPDYSER   600
LCLVSEIPPK GGALGEGPGA SPCNQHSPYW APPCYTLKPE T                      641

SEQ ID NO: 34           moltype = AA  length = 1153
FEATURE                 Location/Qualifiers
REGION                  1..1153
                        note = Made in Lab - Synthesized fusion protein
source                  1..1153
                        mol_type = protein
                        organism = synthetic construct
SEQUENCE: 34
MALPVTALLL PLALLLHAAR PQSALTQPPS ASGTPGQRVT ISCSGSSSNI GSNYVYWYQQ    60
LPGTAPKLLI YRNNQRPSGV PDRFSGSKSG TSASLAISGL RSEDEADYYC AAWDDSLSGY   120
VFGTGTKVTV LGGGGSGGG GSGGGGSQMQ LVQSGAEVKK PGASVKVSCK ASGYTFSRYY   180
IHWVRQAPGQ GLEWMGLINP GGGSTNYAQK FQGRVTMTRD TSTNTVYLEL SSLRSDDTAV   240
YYCARDYGTI DARRFDFWGQ GTLVTVSSTT TPAPRPPTPA PTIASQPLSL RPEACRPAAG   300
GAVHTRGLDF ACDIYIWAPL AGTCGVLLLS LVITLYCKRG RKKLLYIFKQ PFMRPVQTTQ   360
EEDGCSCRFP EEEEGGCELR VKFSRSADAP AYQQGQNQLY NELNLGRREE YDVLDKRRGR   420
DPEMGGKPRR KNPQEGLYNE LQKDKMAEAY SEIGMKGERR RGKGHDGLYQ GLSTATKDTY   480
DALHMQALPP RGSGEGRGSL LTCGDVEENP GPMGRGLLRG LWPLHIVLWT RIASTIPPHV   540
QKSVNNDMIV TDNNGAVKFP QLCKFCDVRF STCDNQKSCM SNCSITSICE KPQEVCVAVW   600
RKNDENITLE TVCHDPKLPY HDFILEDAAS PKCIMKEKKK PGETFFMCSC SSDECNDNII   660
FSEEYNTSNP DLLLVIFQPI LLTISILSFF SVALLVILAC VLWKKRIKPI VWPSLPDHKK   720
TLEHLCKKPR KNLNVSFNPE SFLDCQIHRV DDIQARDEVE GFLQDTFPQQ LEESEKQRLG   780
GDVQSPNCPS EDVVITPESF GRDSSLTCLA GNVSACDAPI LSSSRSLDCR ESGKNGPHVY   840
QDLLLSLGTT NSTLPPPFSL QSGILTLNPV AQGQPILTSL GSNQEEAYVT MSSFYQNQGS   900
GATNFSLLKQ AGDVEENPGP MEAAVAAPRP RLLLLVLAAA AAAAALLPG ATALQCFCHL   960
CTKDNFTCVT DGLCFVSVTE TTDKVIHNSM CIAEIDLIPR DRPFVCAPSS KTGSVTTTYC  1020
CNQDHCNKIE LPTTVKSSPG LGPVELVVIS VGSMGLIISL LCVYFWLERT MPRIPTLKNL  1080
EDLVTEYHGN FSAWSGVSKG LAESLQPDYS ERLCLVSEIP PKGGALGEGP GASPCNQHSP  1140
YWAPPCYTLK PET                                                    1153

SEQ ID NO: 35           moltype = AA  length = 907
FEATURE                 Location/Qualifiers
REGION                  1..907
                        note = Made in Lab - Synthesized fusion protein
VARIANT                 22
                        note = Xaa can be any naturally occurring amino acid
source                  1..907
                        mol_type = protein
                        organism = synthetic construct
SEQUENCE: 35
MALPVTALLL PLALLLHAAR PXTTTPAPRP PTPAPTIASQ PLSLRPEACR PAAGGAVHTR    60
GLDFACDIYI WAPLAGTCGV LLLSLVITLY CKRGRKKLLY IFKQPFMRPV QTTQEEDGCS   120
CRFPEEEEGG CELRVKFSRS ADAPAYQQGQ NQLYNELNLG RREEYDVLDK RRGRDPEMGG   180
KPRRKNPQEG LYNELQKDKM AEAYSEIGMK GERRRGKGHD GLYQGLSTAT KDTYDALHMQ   240
ALPPRGSGEG RGSLLTCGDV EENPGPMGRG LLRGLWPLHI VLWTRIASTI PPHVQKSVNN   300
DMIVTDNNGA VKFPQLCKFC DVRFSTCDNQ KSCMSNCSIT SICEKPQEVC VAVWRKNDEN   360
ITLETVCHDP KLPYHDFILE DAASPKCIMK EKKKPGETFF MCSCSSDECN DNIIFSEEYN   420
TSNPDLLLVI FQPILLTISI LSFFSVALLV ILACVLWKKR IKPIVWPSLP DHKKTLEHLC   480
KKPRKNLNVS FNPESFLDCQ IHRVDDIQAR DEVEGFLQDT FPQQLEESEK QRLGGDVQSP   540
NCPSEDVVIT PESFGRDSSL TCLAGNVSAC DAPILSSSRS LDCRESGKNG PHVYQDLLLS   600
LGTTNSTLPP PFSLQSGILT LNPVAQGQPI LTSLGSNQEE AYVTMSSFYQ NQGSGATNFS   660
LLKQAGDVEE NPGPMEAAVA APRPRLLLLV LAAAAAAAAA LLPGATALQC FCHLCTKDNF   720
```

```
TCVTDGLCFV SVTETTDKVI HNSMCIAEID LIPRDRPFVC APSSKTGSVT TTYCCNQDHC    780
NKIELPTTVK SSPGLGPVEL VVISVGSMGL IISLLCVYFW LERTMPRIPT LKNLEDLVTE    840
YHGNFSAWSG VSKGLAESLQ PDYSERLCLV SEIPPKGGAL GEGPGASPCN QHSPYWAPPC    900
YTLKPET                                                              907

SEQ ID NO: 36           moltype =   length =
SEQUENCE: 36
000

SEQ ID NO: 37           moltype = AA   length = 5
FEATURE                 Location/Qualifiers
REGION                  1..5
                        note = Exemplary linker sequence
source                  1..5
                        mol_type = protein
                        organism = synthetic construct
SEQUENCE: 37
DGGGS                                                                  5

SEQ ID NO: 38           moltype = AA   length = 5
FEATURE                 Location/Qualifiers
REGION                  1..5
                        note = Exemplary linker sequence
source                  1..5
                        mol_type = protein
                        organism = synthetic construct
SEQUENCE: 38
TGEKP                                                                  5

SEQ ID NO: 39           moltype = AA   length = 4
FEATURE                 Location/Qualifiers
REGION                  1..4
                        note = Exemplary linker sequence
source                  1..4
                        mol_type = protein
                        organism = synthetic construct
SEQUENCE: 39
GGRR                                                                   4

SEQ ID NO: 40           moltype = AA   length = 5
FEATURE                 Location/Qualifiers
REGION                  1..5
                        note = Exemplary linker sequence
source                  1..5
                        mol_type = protein
                        organism = synthetic construct
SEQUENCE: 40
GGGGS                                                                  5

SEQ ID NO: 41           moltype = AA   length = 14
FEATURE                 Location/Qualifiers
REGION                  1..14
                        note = Exemplary linker sequence
source                  1..14
                        mol_type = protein
                        organism = synthetic construct
SEQUENCE: 41
EGKSSGSGSE SKVD                                                       14

SEQ ID NO: 42           moltype = AA   length = 18
FEATURE                 Location/Qualifiers
REGION                  1..18
                        note = Exemplary linker sequence
source                  1..18
                        mol_type = protein
                        organism = synthetic construct
SEQUENCE: 42
KESGSVSSEQ LAQFRSLD                                                   18

SEQ ID NO: 43           moltype = AA   length = 8
FEATURE                 Location/Qualifiers
REGION                  1..8
                        note = Exemplary linker sequence
source                  1..8
                        mol_type = protein
                        organism = synthetic construct
SEQUENCE: 43
GGRRGGGS                                                               8
```

```
SEQ ID NO: 44            moltype = AA  length = 9
FEATURE                  Location/Qualifiers
REGION                   1..9
                         note = Exemplary linker sequence
source                   1..9
                         mol_type = protein
                         organism = synthetic construct
SEQUENCE: 44
LRQRDGERP                                                                 9

SEQ ID NO: 45            moltype = AA  length = 12
FEATURE                  Location/Qualifiers
REGION                   1..12
                         note = Exemplary linker sequence
source                   1..12
                         mol_type = protein
                         organism = synthetic construct
SEQUENCE: 45
LRQKDGGGSE RP                                                            12

SEQ ID NO: 46            moltype = AA  length = 16
FEATURE                  Location/Qualifiers
REGION                   1..16
                         note = Exemplary linker sequence
source                   1..16
                         mol_type = protein
                         organism = synthetic construct
SEQUENCE: 46
LRQKDGGGSG GGSERP                                                        16

SEQ ID NO: 47            moltype =     length =
SEQUENCE: 47
000

SEQ ID NO: 48            moltype = AA  length = 7
FEATURE                  Location/Qualifiers
REGION                   1..7
                         note = Cleavage sequence by TEV protease
source                   1..7
                         mol_type = protein
                         organism = synthetic construct
SEQUENCE: 48
ENLYFQG                                                                   7

SEQ ID NO: 49            moltype = AA  length = 7
FEATURE                  Location/Qualifiers
REGION                   1..7
                         note = Cleavage sequence by TEV protease
source                   1..7
                         mol_type = protein
                         organism = synthetic construct
SEQUENCE: 49
ENLYFQS                                                                   7

SEQ ID NO: 50            moltype = AA  length = 22
FEATURE                  Location/Qualifiers
REGION                   1..22
                         note = Self-cleaving polypeptide comprising 2A site
source                   1..22
                         mol_type = protein
                         organism = synthetic construct
SEQUENCE: 50
GSGATNFSLL KQAGDVEENP GP                                                 22

SEQ ID NO: 51            moltype = AA  length = 19
FEATURE                  Location/Qualifiers
REGION                   1..19
                         note = Self-cleaving polypeptide comprising 2A site
source                   1..19
                         mol_type = protein
                         organism = synthetic construct
SEQUENCE: 51
ATNFSLLKQA GDVEENPGP                                                     19

SEQ ID NO: 52            moltype = AA  length = 14
FEATURE                  Location/Qualifiers
REGION                   1..14
                         note = Self-cleaving polypeptide comprising 2A site
source                   1..14
```

```
                        mol_type = protein
                        organism = synthetic construct
SEQUENCE: 52
LLKQAGDVEE NPGP                                                        14

SEQ ID NO: 53           moltype = AA   length = 21
FEATURE                 Location/Qualifiers
REGION                  1..21
                        note = Self-cleaving polypeptide comprising 2A site
source                  1..21
                        mol_type = protein
                        organism = synthetic construct
SEQUENCE: 53
GSGEGRGSLL TCGDVEENPG P                                                21

SEQ ID NO: 54           moltype = AA   length = 18
FEATURE                 Location/Qualifiers
REGION                  1..18
                        note = Self-cleaving polypeptide comprising 2A site
source                  1..18
                        mol_type = protein
                        organism = synthetic construct
SEQUENCE: 54
EGRGSLLTCG DVEENPGP                                                    18

SEQ ID NO: 55           moltype = AA   length = 13
FEATURE                 Location/Qualifiers
REGION                  1..13
                        note = Self-cleaving polypeptide comprising 2A site
source                  1..13
                        mol_type = protein
                        organism = synthetic construct
SEQUENCE: 55
LLTCGDVEEN PGP                                                         13

SEQ ID NO: 56           moltype = AA   length = 23
FEATURE                 Location/Qualifiers
REGION                  1..23
                        note = Self-cleaving polypeptide comprising 2A site
source                  1..23
                        mol_type = protein
                        organism = synthetic construct
SEQUENCE: 56
GSGQCTNYAL LKLAGDVESN PGP                                              23

SEQ ID NO: 57           moltype = AA   length = 20
FEATURE                 Location/Qualifiers
REGION                  1..20
                        note = Self-cleaving polypeptide comprising 2A site
source                  1..20
                        mol_type = protein
                        organism = synthetic construct
SEQUENCE: 57
QCTNYALLKL AGDVESNPGP                                                  20

SEQ ID NO: 58           moltype = AA   length = 14
FEATURE                 Location/Qualifiers
REGION                  1..14
                        note = Self-cleaving polypeptide comprising 2A site
source                  1..14
                        mol_type = protein
                        organism = synthetic construct
SEQUENCE: 58
LLKLAGDVES NPGP                                                        14

SEQ ID NO: 59           moltype = AA   length = 25
FEATURE                 Location/Qualifiers
REGION                  1..25
                        note = Self-cleaving polypeptide comprising 2A site
source                  1..25
                        mol_type = protein
                        organism = synthetic construct
SEQUENCE: 59
GSGVKQTLNF DLLKLAGDVE SNPGP                                            25

SEQ ID NO: 60           moltype = AA   length = 22
FEATURE                 Location/Qualifiers
REGION                  1..22
                        note = Self-cleaving polypeptide comprising 2A site
```

```
source                  1..22
                        mol_type = protein
                        organism = synthetic construct
SEQUENCE: 60
VKQTLNFDLL KLAGDVESNP GP                                                   22

SEQ ID NO: 61           moltype = AA   length = 14
FEATURE                 Location/Qualifiers
REGION                  1..14
                        note = Self-cleaving polypeptide comprising 2A site
source                  1..14
                        mol_type = protein
                        organism = synthetic construct
SEQUENCE: 61
LLKLAGDVES NPGP                                                            14

SEQ ID NO: 62           moltype = AA   length = 19
FEATURE                 Location/Qualifiers
REGION                  1..19
                        note = Self-cleaving polypeptide comprising 2A site
source                  1..19
                        mol_type = protein
                        organism = synthetic construct
SEQUENCE: 62
LLNFDLLKLA GDVESNPGP                                                       19

SEQ ID NO: 63           moltype = AA   length = 19
FEATURE                 Location/Qualifiers
REGION                  1..19
                        note = Self-cleaving polypeptide comprising 2A site
source                  1..19
                        mol_type = protein
                        organism = synthetic construct
SEQUENCE: 63
TLNFDLLKLA GDVESNPGP                                                       19

SEQ ID NO: 64           moltype = AA   length = 14
FEATURE                 Location/Qualifiers
REGION                  1..14
                        note = Self-cleaving polypeptide comprising 2A site
source                  1..14
                        mol_type = protein
                        organism = synthetic construct
SEQUENCE: 64
LLKLAGDVES NPGP                                                            14

SEQ ID NO: 65           moltype = AA   length = 17
FEATURE                 Location/Qualifiers
REGION                  1..17
                        note = Self-cleaving polypeptide comprising 2A site
source                  1..17
                        mol_type = protein
                        organism = synthetic construct
SEQUENCE: 65
NFDLLKLAGD VESNPGP                                                         17

SEQ ID NO: 66           moltype = AA   length = 20
FEATURE                 Location/Qualifiers
REGION                  1..20
                        note = Self-cleaving polypeptide comprising 2A site
source                  1..20
                        mol_type = protein
                        organism = synthetic construct
SEQUENCE: 66
QLLNFDLLKL AGDVESNPGP                                                      20

SEQ ID NO: 67           moltype = AA   length = 24
FEATURE                 Location/Qualifiers
REGION                  1..24
                        note = Self-cleaving polypeptide comprising 2A site
source                  1..24
                        mol_type = protein
                        organism = synthetic construct
SEQUENCE: 67
APVKQTLNFD LLKLAGDVES NPGP                                                 24

SEQ ID NO: 68           moltype = AA   length = 40
FEATURE                 Location/Qualifiers
REGION                  1..40
```

```
                    note = Self-cleaving polypeptide comprising 2A site
source              1..40
                    mol_type = protein
                    organism = synthetic construct
SEQUENCE: 68
VTELLYRMKR AETYCPRPLL AIHPTEARHK QKIVAPVKQT                                    40

SEQ ID NO: 69       moltype = AA  length = 18
FEATURE             Location/Qualifiers
REGION              1..18
                    note = Self-cleaving polypeptide comprising 2A site
source              1..18
                    mol_type = protein
                    organism = synthetic construct
SEQUENCE: 69
LNFDLLKLAG DVESNPGP                                                           18

SEQ ID NO: 70       moltype = AA  length = 40
FEATURE             Location/Qualifiers
REGION              1..40
                    note = Self-cleaving polypeptide comprising 2A site
source              1..40
                    mol_type = protein
                    organism = synthetic construct
SEQUENCE: 70
LLAIHPTEAR HKQKIVAPVK QTLNFDLLKL AGDVESNPGP                                    40

SEQ ID NO: 71       moltype = AA  length = 33
FEATURE             Location/Qualifiers
REGION              1..33
                    note = Self-cleaving polypeptide comprising 2A site
source              1..33
                    mol_type = protein
                    organism = synthetic construct
SEQUENCE: 71
EARHKQKIVA PVKQTLNFDL LKLAGDVESN PGP                                           33

SEQ ID NO: 72       moltype = DNA  length = 10
FEATURE             Location/Qualifiers
misc_feature        1..10
                    note = Consensus Kozak sequence
source              1..10
                    mol_type = other DNA
                    organism = synthetic construct
SEQUENCE: 72
gccrccatgg                                                                    10

SEQ ID NO: 73       moltype =    length =
SEQUENCE: 73
000

SEQ ID NO: 74       moltype =    length =
SEQUENCE: 74
000

SEQ ID NO: 75       moltype = AA  length = 5
FEATURE             Location/Qualifiers
REGION              1..5
                    note = Exemplary rule for determining heavy chain CDR-H2
                     motif
source              1..5
                    mol_type = protein
                    organism = synthetic construct
SEQUENCE: 75
LEWIG                                                                          5

SEQ ID NO: 76       moltype =    length =
SEQUENCE: 76
000
```

>
TGFβ SIGNAL CONVERTOR

CROSS REFERENCE TO RELATED APPLICATIONS

This application is a continuation of U.S. application Ser. No. 16/348,450, filed on May 8, 2019, issued as U.S. Pat. No. 11,654,158 on May 23, 2023, which is a National Stage application under 35 U.S.C. § 371 of International Application No. PCT/US2017/062358, filed Nov. 17, 2017, which claims the benefit under 35 U.S.C. § 119(e) of U.S. Provisional Application No. 62/423,565, filed Nov. 17, 2016, and U.S. Provisional Application No. 62/467,496, filed Mar. 6, 2017, which are incorporated by reference herein in their entirety.

STATEMENT REGARDING SEQUENCE LISTING

The Sequence Listing XML associated with this application is provided in XML file format and is hereby incorporated by reference into the specification. The name of the XML file containing the Sequence Listing XML is 2SEV_080_03US_SeqList_ST26.xml. The XML file is 106,423 bytes, created on Apr. 6, 2023, and is being submitted electronically via USPTO Patent Center, concurrent with the filing of the specification.

BACKGROUND

Technical Field

The present disclosure relates to improved adoptive cell therapies. More particularly, the disclosure relates to improved signaling molecules, cells, and methods of using the same.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

The immune system has a key role in detecting and combating human cancer. The majority of transformed cells are quickly detected by immune sentinels and destroyed through the activation of antigen-specific T cells via clonally expressed T cell receptors (TCR). Accordingly, cancer can be considered an immunological disorder, a failure of immune system to mount the necessary anti-tumor response to durably suppress and eliminate the disease. In order to more effectively combat cancer, certain immunotherapy interventions developed over the last few decades have specifically focused on enhancing T cell immunity. These treatments have yielded only sporadic cases of disease remission, and have not had substantial overall success. More recent therapies that use monoclonal antibodies targeting molecules that inhibit T cell activation, such as CTLA-4 or PD-1, have shown a more substantial anti-tumor effect; however, these treatments are also associated with substantial toxicity due to systemic immune activation.

Most recently, adoptive cellular immunotherapy strategies, which are based on the isolation, modification, expansion and reinfusion of T cells, have been explored and tested in early stage clinical trials. T cells have often been the effector cells of choice for cancer immunotherapy due to their selective recognition and powerful effector mechanisms. These treatments have shown mixed rates of success, but a small number of patients have experienced durable remissions, highlighting the as-yet unrealized potential for T cell-based immunotherapies.

Successful recognition of tumor cell associated antigens by cytolytic T cells initiates targeted tumor lysis and underpins any effective cancer immunotherapy approach. Tumor-infiltrating T cells (TILs) express TCRs specifically directed to tumor-associated antigens; however, substantial numbers of TILs are limited to only a few human cancers. Engineered T cell receptors (TCRs) and chimeric antigen receptors (CARs) potentially increase the applicability of T cell-based immunotherapy to many cancers and other immune disorders.

In addition, state of the art engineered T cells are still regulated by a complex immunosuppressive tumor microenvironment that consists of cancer cells, inflammatory cells, stromal cells and cytokines. Among these components, cancer cells, inflammatory cells and suppressive cytokines adversely impact T cell phenotype and function. Collectively, the tumor microenvironment drives T cells to terminally differentiate into exhausted T cells.

T cell exhaustion is a state of T cell dysfunction in a chronic environment marked by increased expression of, or increased signaling by inhibitory receptors; reduced effector cytokine production; and a decreased ability to persist and eliminate cancer. Exhausted T cells also show loss of function in a hierarchical manner: decreased IL-2 production and ex vivo killing capacity are lost at the early stage of exhaustion, TNF-α production is lost at the intermediate stage, and IFN-γ and GzmB production are lost at the advanced stage of exhaustion. Most T cells in the tumor microenvironment differentiate into exhausted T cells and lose the ability to eliminate cancer and are eventually cleared.

Transforming growth factor beta (TGFβ) is a pleiotropic cytokine that has been implicated as an immunosuppressive signaling molecule in the tumor microenvironment. TGFβ binds to the TGFβR1 and TGFβR2 serine/threonine kinase receptor complexes, resulting in receptor-mediated phosphorylation of downstream transcription factors Smad2 and Smad3. Many tumors evade the cytostatic and anti-proliferative effects of TGFβ by acquiring mutations in the TGFβR2 receptors and/or downstream Smad signaling proteins. TGFβ suppresses key molecules involved in the effector and cytolytic activities of T cells in vitro, including IFNγ secretion.

To date, clinical trials directed to the inhibition of TGFβ signaling using neutralizing Abs or kinase inhibitors have yielded disappointing results and significant therapeutic benefits have not yet been reported.

BRIEF SUMMARY

The present disclosure generally relates, in part, to improved TGFβ signal convertors (chimeric TGFβ receptors or CTBRs), genetically modified cells, compositions, and methods of using the same.

In various embodiments, a fusion polypeptide is contemplated comprising: a first polypeptide comprising: an extracellular TGFβ1-binding domain of TGFβR2, a transmembrane domain, and an immune receptor intracellular signaling domain; a polypeptide cleavage signal; and a second polypeptide comprising an extracellular TGFβ1-binding domain of TGFβR1, a transmembrane domain, and an immune receptor intracellular signaling domain.

In additional embodiments, the immune receptor intracellular signaling domain of the first polypeptide is isolated from a cytokine receptor, an interleukin receptor, a pattern recognition receptor, or a toll-like receptor.

In particular embodiments, the immune receptor intracellular signaling domain of the second polypeptide is isolated from a cytokine receptor, an interleukin receptor, a pattern recognition receptor, or a toll-like receptor.

In some embodiments, the immune receptor intracellular signaling domain of the first polypeptide is an IL-12Rβ2 intracellular signaling domain and the immune receptor intracellular signaling domain of the second polypeptide is an IL-12Rβ1 intracellular signaling domain. In various embodiments, the transmembrane domain of the first polypeptide comprises an IL-12Rβ2 transmembrane domain. In particular embodiments, the transmembrane domain of the second polypeptide comprises an IL-12Rβ1 transmembrane domain. In particular embodiments, the fusion protein is referred to as a CTBR12 or CTBR12 signal convertor.

In certain embodiments, the immune receptor intracellular signaling domain of the first polypeptide is an IL-12Rβ1 intracellular signaling domain and the immune receptor intracellular signaling domain of the second polypeptide is an IL-12Rβ2 intracellular signaling domain. In further embodiments, the transmembrane domain of the first polypeptide comprises an IL-12Rβ1 transmembrane domain. In particular embodiments, the transmembrane domain of the second polypeptide comprises an IL-12Rβ2 transmembrane domain. In particular embodiments, the fusion protein is referred to as a CTBR12 or CTBR12 signal convertor.

In additional embodiments, the immune receptor intracellular signaling domain of the first polypeptide is an IL-7Rα intracellular signaling domain and the immune receptor intracellular signaling domain of the second polypeptide is an IL-2Rγ intracellular signaling domain. In some embodiments, the transmembrane domain of the first polypeptide comprises an IL-7Rα transmembrane domain. In particular embodiments, the transmembrane domain of the second polypeptide comprises an IL-2Rγ transmembrane domain. In particular embodiments, the fusion protein is referred to as a CTBR7 or CTBR7 signal convertor.

In various embodiments, the immune receptor intracellular signaling domain of the first polypeptide is an IL-2Rγ intracellular signaling domain and the immune receptor intracellular signaling domain of the second polypeptide is an IL-7Rα intracellular signaling domain. In further embodiments, the transmembrane domain of the first polypeptide comprises an IL-2Rγ transmembrane domain. In certain embodiments, the transmembrane domain of the second polypeptide comprises an IL-7Rα transmembrane domain. In particular embodiments, the fusion protein is referred to as a CTBR7 or CTBR7 signal convertor.

In additional embodiments, the immune receptor intracellular signaling domain of the first polypeptide is an IL-2Rβ intracellular signaling domain and the immune receptor intracellular signaling domain of the second polypeptide is an IL-2Rγ intracellular signaling domain. In various embodiments, the transmembrane domain of the first polypeptide comprises an IL-2Rβ transmembrane domain. In various embodiments, the transmembrane domain of the second polypeptide comprises an IL-2Rγ transmembrane domain. In particular embodiments, the fusion protein is referred to as a CTBR15 or CTBR15 signal convertor.

In particular embodiments, the immune receptor intracellular signaling domain of the first polypeptide is an IL-2Rγ intracellular signaling domain and the immune receptor intracellular signaling domain of the second polypeptide is an IL-2Rβ intracellular signaling domain. In some embodiments, the transmembrane domain of the first polypeptide comprises an IL-2Rγ transmembrane domain. In certain embodiments, the transmembrane domain of the second polypeptide comprises an IL-2Rβ transmembrane domain. In particular embodiments, the fusion protein is referred to as a CTBR15 or CTBR15 signal convertor.

In further embodiments, the immune receptor intracellular signaling domain of the first polypeptide is an IL-21R intracellular signaling domain and the immune receptor intracellular signaling domain of the second polypeptide is an IL-2Rγ intracellular signaling domain. In particular embodiments, the transmembrane domain of the first polypeptide comprises an IL-21R transmembrane domain. In various embodiments, the transmembrane domain of the second polypeptide comprises an IL-2Rγ transmembrane domain. In particular embodiments, the fusion protein is referred to as a CTBR21 or CTBR21 signal convertor.

In additional embodiments, the immune receptor intracellular signaling domain of the first polypeptide is an IL-2Rγ intracellular signaling domain and the immune receptor intracellular signaling domain of the second polypeptide is an IL-21R intracellular signaling domain. In certain embodiments, the transmembrane domain of the first polypeptide comprises an IL-2Rγ transmembrane domain. In further embodiments, the transmembrane domain of the second polypeptide comprises an IL-21R transmembrane domain. In particular embodiments, the fusion protein is referred to as a CTBR21 or CTBR21 signal convertor.

In various embodiments, the immune receptor intracellular signaling domain of the first polypeptide is an IL-18R1 intracellular signaling domain and the immune receptor intracellular signaling domain of the second polypeptide is an IL-18RAP intracellular signaling domain. In some embodiments, the transmembrane domain of the first polypeptide comprises an IL-18R1 transmembrane domain. In various embodiments, the transmembrane domain of the second polypeptide comprises an IL-18RAP transmembrane domain. In particular embodiments, the fusion protein is referred to as a CTBR18 or CTBR18 signal convertor.

In some embodiments, the immune receptor intracellular signaling domain of the first polypeptide is an IL-18RAP intracellular signaling domain and the immune receptor intracellular signaling domain of the second polypeptide is an IL-18R1 intracellular signaling domain. In additional embodiments, the transmembrane domain of the first polypeptide comprises an IL-18RAP transmembrane domain. In particular embodiments, the transmembrane domain of the second polypeptide comprises an IL-18R1 transmembrane domain. In particular embodiments, the fusion protein is referred to as a CTBR18 or CTBR18 signal convertor.

In certain embodiments, the immune receptor intracellular signaling domain of the first polypeptide is an IL-1R1 intracellular signaling domain and the immune receptor intracellular signaling domain of the second polypeptide is an IL-1RAP intracellular signaling domain. In further embodiments, the transmembrane domain of the first polypeptide comprises an IL-1R1 transmembrane domain. In various embodiments, the transmembrane domain of the second polypeptide comprises an IL-1RAP transmembrane domain. In particular embodiments, the fusion protein is referred to as a CTBR1 or CTBR1 signal convertor.

In certain embodiments, the immune receptor intracellular signaling domain of the first polypeptide is an IL-1RAP intracellular signaling domain and the immune receptor intracellular signaling domain of the second polypeptide is an IL-1R1 intracellular signaling domain. In various embodiments, the transmembrane domain of the first polypeptide comprises an IL-1RAP transmembrane domain. In some embodiments, the transmembrane domain of the second polypeptide comprises an IL-1R1 transmembrane domain. In particular embodiments, the fusion protein is referred to as a CTBR1 or CTBR1 signal convertor.

In additional embodiments, the immune receptor intracellular signaling domain of the first polypeptide is an IL-1RAP intracellular signaling domain and the immune receptor intracellular signaling domain of the second polypeptide is an IL-1RL2 intracellular signaling domain. In various embodiments, the transmembrane domain of the first polypeptide comprises an IL-1RAP transmembrane domain. In further embodiments, the transmembrane domain of the second polypeptide comprises an IL-1RL2 transmembrane domain. In particular embodiments, the fusion protein is referred to as a CTBR36 or CTBR36 signal convertor.

In particular embodiments, the immune receptor intracellular signaling domain of the first polypeptide is an IL-1RL2 intracellular signaling domain and the immune receptor intracellular signaling domain of the second polypeptide is an IL-1RAP intracellular signaling domain. In certain embodiments, the transmembrane domain of the first polypeptide comprises an IL-1RL2 transmembrane domain. In some embodiments, the transmembrane domain of the second polypeptide comprises an IL-1RAP transmembrane domain. In particular embodiments, the fusion protein is referred to as a CTBR36 or CTBR36 signal convertor.

In various embodiments, the immune receptor intracellular signaling domain of the first polypeptide is an IFNAR1 intracellular signaling domain and the immune receptor intracellular signaling domain of the second polypeptide is an IFNAR2 intracellular signaling domain. In further embodiments, the transmembrane domain of the first polypeptide comprises an IFNAR1 transmembrane domain. In particular embodiments, the transmembrane domain of the second polypeptide comprises an IFNAR2 transmembrane domain. In particular embodiments, the fusion protein is referred to as a CTBRIFN1 or CTBRIFN1 signal convertor.

In various embodiments, the immune receptor intracellular signaling domain of the first polypeptide is an IFNAR2 intracellular signaling domain and the immune receptor intracellular signaling domain of the second polypeptide is an IFNAR1 intracellular signaling domain. In certain embodiments, the transmembrane domain of the first polypeptide comprises an IFNAR2 transmembrane domain. In various embodiments, the transmembrane domain of the second polypeptide comprises an IFNAR1 transmembrane domain. In particular embodiments, the fusion protein is referred to as a CTBR.IFN1 or CTBR.IFN1 signal convertor.

In further embodiments, the immune receptor intracellular signaling domain of the first polypeptide is a TLR1 intracellular signaling domain and the immune receptor intracellular signaling domain of the second polypeptide is a TLR1 intracellular signaling domain. In additional embodiments, the transmembrane domain of the first polypeptide comprises a TLR1 transmembrane domain. In some embodiments, the transmembrane domain of the second polypeptide comprises a TLR1 transmembrane domain. In particular embodiments, the fusion protein is referred to as a CTBR.TLR1 or CTBR.TLR1 signal convertor.

In particular embodiments, the immune receptor intracellular signaling domain of the first polypeptide is a TLR2 intracellular signaling domain and the immune receptor intracellular signaling domain of the second polypeptide is a TLR2 intracellular signaling domain. In certain embodiments, the transmembrane domain of the first polypeptide comprises a TLR2 transmembrane domain. In further embodiments, the transmembrane domain of the second polypeptide comprises a TLR2 transmembrane domain. In particular embodiments, the fusion protein is referred to as a CTBR.TLR2 or CTBR.TLR2 signal convertor.

In various embodiments, the immune receptor intracellular signaling domain of the first polypeptide is a TLR3 intracellular signaling domain and the immune receptor intracellular signaling domain of the second polypeptide is a TLR3 intracellular signaling domain. In further embodiments, the transmembrane domain of the first polypeptide comprises a TLR3 transmembrane domain. In particular embodiments, the transmembrane domain of the second polypeptide comprises a TLR3 transmembrane domain. In particular embodiments, the fusion protein is referred to as a CTBR.TLR3 or CTBR.TLR3 signal convertor.

In various embodiments, the immune receptor intracellular signaling domain of the first polypeptide is a TLR4 intracellular signaling domain and the immune receptor intracellular signaling domain of the second polypeptide is a TLR4 intracellular signaling domain. In some embodiments, the transmembrane domain of the first polypeptide comprises a TLR4 transmembrane domain. In certain embodiments, the transmembrane domain of the second polypeptide comprises a TLR4 transmembrane domain. In particular embodiments, the fusion protein is referred to as a CTBR.TLR4 or CTBR.TLR4 signal convertor.

In additional embodiments, the immune receptor intracellular signaling domain of the first polypeptide is a TLR5 intracellular signaling domain and the immune receptor intracellular signaling domain of the second polypeptide is a TLR5 intracellular signaling domain. In particular embodiments, the transmembrane domain of the first polypeptide comprises a TLR5 transmembrane domain. In various embodiments, the transmembrane domain of the second polypeptide comprises a TLR5 transmembrane domain. In particular embodiments, the fusion protein is referred to as a CTBR.TLR5 or CTBR.TLR5 signal convertor.

In some embodiments, the immune receptor intracellular signaling domain of the first polypeptide is a TLR6 intracellular signaling domain and the immune receptor intracellular signaling domain of the second polypeptide is a TLR6 intracellular signaling domain. In further embodiments, the transmembrane domain of the first polypeptide comprises a TLR6 transmembrane domain. In particular embodiments, the transmembrane domain of the second polypeptide comprises a TLR6 transmembrane domain. In particular embodiments, the fusion protein is referred to as a CTBR.TLR6 or CTBR.TLR6 signal convertor.

In some embodiments, the immune receptor intracellular signaling domain of the first polypeptide is a TLR7 intracellular signaling domain and the immune receptor intracellular signaling domain of the second polypeptide is a TLR7 intracellular signaling domain. In various embodiments, the transmembrane domain of the first polypeptide comprises a TLR7 transmembrane domain. In further embodiments, the transmembrane domain of the second polypeptide comprises a TLR7 transmembrane domain. In particular embodiments, the fusion protein is referred to as a CTBR.TLR7 or CTBR.TLR7 signal convertor.

In certain embodiments, the immune receptor intracellular signaling domain of the first polypeptide is a TLR8 intracellular signaling domain and the immune receptor intracellular signaling domain of the second polypeptide is a TLR8 intracellular signaling domain. In particular embodiments, the transmembrane domain of the first polypeptide comprises a TLR8 transmembrane domain. In some embodiments, the transmembrane domain of the second polypeptide comprises a TLR8 transmembrane domain. In particular embodiments, the fusion protein is referred to as a CTBR.TLR8 or CTBR.TLR8 signal convertor.

In various embodiments, the immune receptor intracellular signaling domain of the first polypeptide is a TLR9 intracellular signaling domain and the immune receptor intracellular signaling domain of the second polypeptide is a TLR9 intracellular signaling domain. In further embodiments, the transmembrane domain of the first polypeptide comprises a TLR9 transmembrane domain. In additional embodiments, the transmembrane domain of the second polypeptide comprises a TLR9 transmembrane domain. In particular embodiments, the fusion protein is referred to as a CTBR.TLR9 or CTBR.TLR9 signal convertor.

In certain embodiments, the immune receptor intracellular signaling domain of the first polypeptide is a TLR10 intracellular signaling domain and the immune receptor intracellular signaling domain of the second polypeptide is a TLR10 intracellular signaling domain. In certain embodiments, the transmembrane domain of the first polypeptide comprises a TLR10 transmembrane domain. In particular embodiments, the transmembrane domain of the second polypeptide comprises a TLR10 transmembrane domain. In particular embodiments, the fusion protein is referred to as a CTBR.TLR10 or CTBR.TLR10 signal convertor.

In further embodiments, the polypeptide cleavage signal is a viral self-cleaving polypeptide.

In various embodiments, the polypeptide cleavage signal is a viral self-cleaving 2A polypeptide.

In some embodiments, the polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In particular embodiments, a fusion polypeptide comprises: a TGFβR2 polypeptide comprising an extracellular TGFβ1-binding domain of TGFβR2, an IL-12Rβ2 transmembrane domain, and an IL-12Rβ2 intracellular signaling domain; a viral self-cleaving 2A peptide; and a TGFβR1 polypeptide comprising an extracellular TGFβ1-binding domain of TGFβR1, an IL-12Rβ1 transmembrane domain, and an IL-12Rβ1 intracellular signaling domain. In particular embodiments, the fusion protein is referred to as a CTBR12 or CTBR12 signal convertor.

In various embodiments, a fusion polypeptide comprises: a TGFβR2 polypeptide comprising an extracellular TGFβ1-binding domain of TGFβR2, an IL-12Rβ1 transmembrane domain, and an IL-12Rβ1 intracellular signaling domain; a viral self-cleaving 2A peptide; and a TGFβR1 polypeptide comprising an extracellular TGFβ1-binding domain of TGFβR1, an IL-12Rβ2 transmembrane domain, and an IL-12Rβ2 intracellular signaling domain. In particular embodiments, the fusion protein is referred to as a CTBR12 or CTBR12 signal convertor.

In additional embodiments, a fusion polypeptide comprises: a TGFβR2 polypeptide comprising an extracellular TGFβ1-binding domain of TGFβR2, an IL-7Rα transmembrane domain, and an IL-7Rα intracellular signaling domain; a viral self-cleaving 2A peptide; and a TGFβR1 polypeptide comprising an extracellular TGFβ1-binding domain of TGFβR1, an IL-2Rγ transmembrane domain, and an IL-2Rγ intracellular signaling domain. In particular embodiments, the fusion protein is referred to as a CTBR7 or CTBR7 signal convertor.

In particular embodiments, a fusion polypeptide comprises: a TGFβR2 polypeptide comprising an extracellular TGFβ1-binding domain of TGFβR2, an IL-2Rγ transmembrane domain, and an IL-2Rγ intracellular signaling domain; a viral self-cleaving 2A peptide; and a TGFβR1 polypeptide comprising an extracellular TGFβ1-binding domain of TGFβR1, an IL-7Rα transmembrane domain, and an IL-7Rα intracellular signaling domain. In particular embodiments, the fusion protein is referred to as a CTBR7 or CTBR7 signal convertor.

In certain embodiments, a fusion polypeptide comprises: a TGFβR2 polypeptide comprising an extracellular TGFβ1-binding domain of TGFβR2, an IL-2Rβ transmembrane domain, and an IL-2Rβ intracellular signaling domain; a viral self-cleaving 2A peptide; and a TGFβR1 polypeptide comprising an extracellular TGFβ1-binding domain of TGFβR1, an IL-2Rγ transmembrane domain, and an IL-2Rγ intracellular signaling domain. In particular embodiments, the fusion protein is referred to as a CTBR15 or CTBR15 signal convertor.

In various embodiments, a fusion polypeptide comprises: a TGFβR2 polypeptide comprising an extracellular TGFβ1-binding domain of TGFβR2, an IL-2Rγ transmembrane domain, and an IL-2Rγ intracellular signaling domain; a viral self-cleaving 2A peptide; and a TGFβR1 polypeptide comprising an extracellular TGFβ1-binding domain of TGFβR1, an IL-2Rβ transmembrane domain, and an IL-2Rβ intracellular signaling domain. In particular embodiments, the fusion protein is referred to as a CTBR15 or CTBR15 signal convertor.

In some embodiments, a fusion polypeptide comprises: a TGFβR2 polypeptide comprising an extracellular TGFβ1-binding domain of TGFβR2, an IL-21R transmembrane domain, and an IL-21R intracellular signaling domain; a viral self-cleaving 2A peptide; and a TGFβR1 polypeptide comprising an extracellular TGFβ1-binding domain of TGFβR1, an IL-2Rγ transmembrane domain, and an IL-2Rγ intracellular signaling domain. In particular embodiments, the fusion protein is referred to as a CTBR21 or CTBR21 signal convertor.

In certain embodiments, a fusion polypeptide comprises: a TGFβR2 polypeptide comprising an extracellular TGFβ1-binding domain of TGFβR2, an IL-2Rγ transmembrane domain, and an IL-2Rγ intracellular signaling domain; a viral self-cleaving 2A peptide; and a TGFβR1 polypeptide comprising an extracellular TGFβ1-binding domain of TGFβR1, an IL-21R transmembrane domain, and an IL-21R intracellular signaling domain. In particular embodiments, the fusion protein is referred to as a CTBR21 or CTBR21 signal convertor.

In various embodiments, a fusion polypeptide comprises: a TGFβR2 polypeptide comprising an extracellular TGFβ1-binding domain of TGFβR2, an IL-18R1 transmembrane domain, and an IL-18R1 intracellular signaling domain; a viral self-cleaving 2A peptide; and a TGFβR1 polypeptide comprising an extracellular TGFβ1-binding domain of TGFβR1, an IL-18RAP transmembrane domain, and an IL-18RAP intracellular signaling domain. In particular embodiments, the fusion protein is referred to as a CTBR18 or CTBR18 signal convertor.

In additional embodiments, a fusion polypeptide comprises: a TGFβR2 polypeptide comprising an extracellular TGFβ1-binding domain of TGFβR2, an IL-18RAP transmembrane domain, and an IL-18RAP intracellular signaling domain; a viral self-cleaving 2A peptide; and a TGFβR1 polypeptide comprising an extracellular TGFβ1-binding domain of TGFβR1, an IL-18R1 transmembrane domain, and an IL-18R1 intracellular signaling domain. In particular embodiments, the fusion protein is referred to as a CTBR18 or CTBR18 signal convertor.

In particular embodiments, a fusion polypeptide comprises: a TGFβR2 polypeptide comprising an extracellular TGFβ1-binding domain of TGFβR2, an IL-1R1 transmembrane domain, and an IL-1R1 intracellular signaling domain; a viral self-cleaving 2A peptide; and a TGFβR1 polypeptide comprising an extracellular TGFβ1-binding domain of TGFβR1, an IL-1RAP transmembrane domain, and an IL-1RAP intracellular signaling domain. In particular embodiments, the fusion protein is referred to as a CTBR36 or CTBR36 signal convertor.

In certain embodiments, a fusion polypeptide comprises: a TGFβR2 polypeptide comprising an extracellular TGFβ1-binding domain of TGFβR2, an IL-1RAP transmembrane domain, and an IL-1RAP intracellular signaling domain; a viral self-cleaving 2A peptide; and a TGFβR1 polypeptide comprising an extracellular TGFβ1-binding domain of TGFβR1, an IL-1R1 transmembrane domain, and an IL-1R1 intracellular signaling domain. In particular embodiments, the fusion protein is referred to as a CTBR36 or CTBR36 signal convertor.

In various embodiments, a fusion polypeptide comprises: a TGFβR2 polypeptide comprising an extracellular TGFβ1-binding domain of TGFβR2, an IFNAR1 transmembrane domain, and an IFNAR1 intracellular signaling domain; a viral self-cleaving 2A peptide; and a TGFβR1 polypeptide comprising an extracellular TGFβ1-binding domain of TGFβR1, an IFNAR2 transmembrane domain, and an IFNAR2 intracellular signaling domain. In particular embodiments, the fusion protein is referred to as a CTBR.IFN1 or CTBR.IFN1 signal convertor.

In some embodiments, a fusion polypeptide comprises: a TGFβR2 polypeptide comprising an extracellular TGFβ1-binding domain of TGFβR2, an IFNAR2 transmembrane domain, and an IFNAR2 intracellular signaling domain; a viral self-cleaving 2A peptide; and a TGFβR1 polypeptide comprising an extracellular TGFβ1-binding domain of TGFβR1, an IFNAR1 transmembrane domain, and an IFNAR1 intracellular signaling domain.

In further embodiments, a fusion polypeptide comprises: a TGFβR2 polypeptide comprising an extracellular TGFβ1-binding domain of TGFβR2, a TLR1 transmembrane domain, and a TLR1 intracellular signaling domain; a viral self-cleaving 2A peptide; and a TGFβR1 polypeptide comprising an extracellular TGFβ1-binding domain of TGFβR1, a TLR1 transmembrane domain, and a TLR1 intracellular signaling domain. In particular embodiments, the fusion protein is referred to as a CTBR.TLR1 or CTBR.TLR1 signal convertor.

In particular embodiments, a fusion polypeptide comprises: a TGFβR2 polypeptide comprising an extracellular TGFβ1-binding domain of TGFβR2, a TLR2 transmembrane domain, and a TLR2 intracellular signaling domain; a viral self-cleaving 2A peptide; and a TGFβR1 polypeptide comprising an extracellular TGFβ1-binding domain of TGFβR1, a TLR2 transmembrane domain, and a TLR2 intracellular signaling domain. In particular embodiments, the fusion protein is referred to as a CTBR.TLR2 or CTBR.TLR2 signal convertor.

In various embodiments, a fusion polypeptide comprises: a TGFβR2 polypeptide comprising an extracellular TGFβ1-binding domain of TGFβR2, a TLR3 transmembrane domain, and a TLR3 intracellular signaling domain; a viral self-cleaving 2A peptide; and a TGFβR1 polypeptide comprising an extracellular TGFβ1-binding domain of TGFβR1, a TLR3 transmembrane domain, and a TLR3 intracellular signaling domain. In particular embodiments, the fusion protein is referred to as a CTBR.TLR3 or CTBR.TLR3 signal convertor.

In certain embodiments, a fusion polypeptide comprises: a TGFβR2 polypeptide comprising an extracellular TGFβ1-binding domain of TGFβR2, a TLR4 transmembrane domain, and a TLR4 intracellular signaling domain; a viral self-cleaving 2A peptide; and a TGFβR1 polypeptide comprising an extracellular TGFβ1-binding domain of TGFβR1, a TLR4 transmembrane domain, and a TLR4 intracellular signaling domain. In particular embodiments, the fusion protein is referred to as a CTBR.TLR4 or CTBR.TLR4 signal convertor.

In additional embodiments, a fusion polypeptide comprises: a TGFβR2 polypeptide comprising an extracellular TGFβ1-binding domain of TGFβR2, a TLR5 transmembrane domain, and a TLR5 intracellular signaling domain; a viral self-cleaving 2A peptide; and a TGFβR1 polypeptide comprising an extracellular TGFβ1-binding domain of TGFβR1, a TLR5 transmembrane domain, and a TLR5 intracellular signaling domain. In particular embodiments, the fusion protein is referred to as a CTBR.TLR5 or CTBR.TLR5 signal convertor.

In various embodiments, a fusion polypeptide comprises: a TGFβR2 polypeptide comprising an extracellular TGFβ1-binding domain of TGFβR2, a TLR6 transmembrane domain, and a TLR6 intracellular signaling domain; a viral self-cleaving 2A peptide; and a TGFβR1 polypeptide comprising an extracellular TGFβ1-binding domain of TGFβR1, a TLR6 transmembrane domain, and a TLR6 intracellular signaling domain. In particular embodiments, the fusion protein is referred to as a CTBR.TLR6 or CTBR.TLR6 signal convertor.

In some embodiments, a fusion polypeptide comprises: a TGFβR2 polypeptide comprising an extracellular TGFβ1-binding domain of TGFβR2, a TLR7 transmembrane domain, and a TLR7 intracellular signaling domain; a viral self-cleaving 2A peptide; and a TGFβR1 polypeptide comprising an extracellular TGFβ1-binding domain of TGFβR1, a TLR7 transmembrane domain, and a TLR7 intracellular signaling domain. In particular embodiments, the fusion protein is referred to as a CTBR.TLR7 or CTBR.TLR7 signal convertor.

In particular embodiments, a fusion polypeptide comprises: a TGFβR2 polypeptide comprising an extracellular TGFβ1-binding domain of TGFβR2, a TLR8 transmembrane domain, and a TLR8 intracellular signaling domain; a viral self-cleaving 2A peptide; and a TGFβR1 polypeptide comprising an extracellular TGFβ1-binding domain of TGFβR1, a TLR8 transmembrane domain, and a TLR8 intracellular signaling domain. In particular embodiments, the fusion protein is referred to as a CTBR.TLR8 or CTBR.TLR8 signal convertor.

In additional embodiments, a fusion polypeptide comprises: a TGFβR2 polypeptide comprising an extracellular TGFβ1-binding domain of TGFβR2, a TLR9 transmembrane domain, and a TLR9 intracellular signaling domain; a viral self-cleaving 2A peptide; and a TGFβR1 polypeptide comprising an extracellular TGFβ1-binding domain of TGFβR1, a TLR9 transmembrane domain, and a TLR9 intracellular signaling domain. In particular embodiments, the fusion protein is referred to as a CTBR.TLR9 or CTBR.TLR9 signal convertor.

In various embodiments, a fusion polypeptide comprises: a TGFβR2 polypeptide comprising an extracellular TGFβ1-binding domain of TGFβR2, a TLR10 transmembrane domain, and a TLR10 intracellular signaling domain; a viral self-cleaving 2A peptide; and a TGFβR1 polypeptide comprising an extracellular TGFβ1-binding domain of TGFβR1, a TLR10 transmembrane domain, and a TLR10 intracellular signaling domain. In particular embodiments, the fusion protein is referred to as a CTBR.TLR10 or CTBR.TLR10 signal convertor.

In some embodiments, the viral self-cleaving 2A polypeptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In further embodiments, a fusion polypeptide contemplated herein further comprises an engineered antigen receptor and a second viral self-cleaving 2A polypeptide.

In certain embodiments, the second viral self-cleaving 2A polypeptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In particular embodiments, the engineered antigen receptor is selected from the group consisting of: an engineered T cell receptor (TCR), a chimeric antigen receptor (CAR), a DARIC receptor or components thereof, and a chimeric cytokine receptor; optionally, wherein the engineered antigen receptor recognizes an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Mucl, Muc16, NCAM, NKG2D Ligands, NY-ESO-1, PRAIVIE, PSCA, PSMA, ROR1, SSX, Survivin, TAG72, TEMs, VEGFR2, and WT-1.

In further embodiments, a fusion polypeptide comprises an amino acid sequence set forth in any one of SEQ ID NOs: 26 to 35.

In various embodiments, a polynucleotide encoding a fusion polypeptide contemplated herein is provided.

In additional embodiments, a vector comprising a polynucleotide or a fusion polynucleotide contemplated herein is provided.

In particular embodiments, a cell comprising a fusion polypeptide, a polynucleotide, or a vector contemplated herein is provided.

In further embodiments, the cell is a hematopoietic cell.

In certain embodiments, the cell is a T cell.

In various embodiments, the cell is a CD3+, CD4+, and/or CD8+ cell.

In some embodiments, the cell is an immune effector cell.

In additional embodiments, the cell is a cytotoxic T lymphocytes (CTLs), a tumor infiltrating lymphocytes (TILs), or a helper T cells.

In further embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In some embodiments, a cell comprising a fusion polypeptide contemplated herein further comprises an engineered antigen receptor.

In various embodiments, the engineered antigen receptor is selected from the group consisting of: an engineered T cell receptor (TCR), a chimeric antigen receptor (CAR), a DARIC receptor or components thereof, and a chimeric cytokine receptor.

In additional embodiments, a composition comprising a fusion polypeptide, a polynucleotide, a vector, or a cell contemplated herein is provided.

In particular embodiments, a pharmaceutical composition comprising a pharmaceutically acceptable carrier and a fusion polypeptide, a polynucleotide, a vector, or a cell contemplated herein is provided.

In certain embodiments, a method of treating a subject in need thereof comprises administering the subject an effective amount of a composition or pharmaceutical composition contemplated herein.

In some embodiments, a method of treating, preventing, or ameliorating at least one symptom of a cancer, infectious disease, autoimmune disease, inflammatory disease, and immunodeficiency, or condition associated therewith, comprises administering to the subject an effective amount of a composition or pharmaceutical composition contemplated herein.

In additional embodiments, a method of treating a solid cancer comprises administering to the subject an effective amount of a composition or pharmaceutical composition contemplated herein.

In various embodiments, the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, or skin cancer.

In particular embodiments, the solid cancer is a pancreatic cancer, a lung cancer, or a breast cancer.

In certain embodiments, a method of treating a hematological malignancy comprises administering to the subject an effective amount of a composition or pharmaceutical composition contemplated herein is provided.

In various embodiments, the hematological malignancy is a leukemia, lymphoma, or multiple myeloma.

BRIEF DESCRIPTION OF SEVERAL VIEWS OF THE DRAWINGS

FIG. 15 also shows phospho-SMAD2/3 expression in primary human T cells transduced with an anti-EGFR CAR alone and in combination with the TGFβ DNR, the CTBR12 signal convertor, and the CTBR7 signal convertor and treated with TGFβ1 (bottom panel) compared to untreated cells.

FIG. 20 shows a cartoon of polypeptides encoding a T cell receptor (TCR) that recognizes NY-ESO1 (A2), an NY-ESO1 TCR and a TGFβ dominant negative receptor (NY-ESO1.DNR); an NY-ESO1 TCR and CTBR7 signal convertor (NY-ESO1.CTBR7), and an NY-ESO1 TCR and CTBR12 signal convertor (NY-ESO1.CTBR12).

FIG. 22 also shows phospho-STAT4 expression in primary human T cells transduced with an NY-ESO1.CTBR12 and treated with either IL-12 or TGFβ1 (bottom panel).

FIG. 23 shows IFNγ secretion from primary human T cells transduced with an NY-ESO1 TCR, NY-ESO1.DNR, NY-ESO1.CTBR7, and NY-ESO1.CTBR12 cultured with A2(+). NY-ESO1(+) cell lines in the presence or absence of TGFβ1.

BRIEF DESCRIPTION OF THE SEQUENCE IDENTIFIERS

Figure 1:
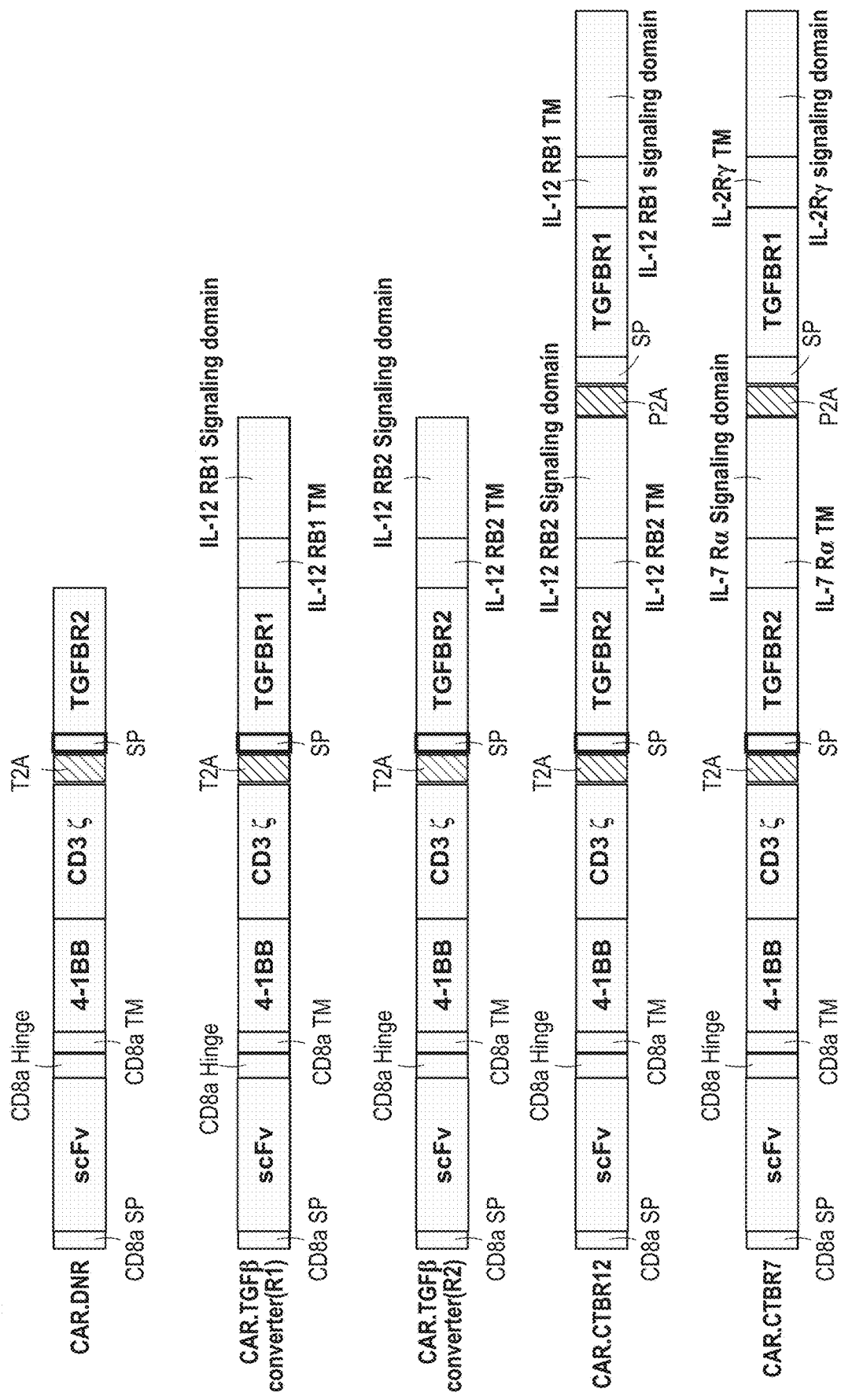
FIG. 1 shows a cartoon of polypeptides encoding a chimeric antigen receptor (CAR) and TGFβ dominant negative receptor (CAR.DNR); a CAR and a TGFβR2 subunit (R2); a CAR and CTBR12 signal convertor (CAR.CTBR12), and a CAR and CTBR7 signal convertor (CAR.CTBR7).

SEQ ID NO: 1 sets forth the polypeptide sequence of human TGFβR1.

SEQ ID NO: 2 sets forth the polypeptide sequence of human TGFβR2.

SEQ ID NO: 3 sets forth the polypeptide sequence of human IL-12Rβ1 (CD212).

SEQ ID NO: 4 sets forth the polypeptide sequence of human IL-12Rβ2.

SEQ ID NO: 5 sets forth the polypeptide sequence of human IL-7Rα (CD127).

SEQ ID NO: 6 sets forth the polypeptide sequence of human IL-2Rγ (CD132).

SEQ ID NO: 7 sets forth the polypeptide sequence of human IL-2Rβ (CD122).

SEQ ID NO: 8 sets forth the polypeptide sequence of human IL-21R (CD360).

SEQ ID NO: 9 sets forth the polypeptide sequence of human IL-18R1 (CD218a).

SEQ ID NO: 10 sets forth the polypeptide sequence of human IL-18RAP (CD218b).

SEQ ID NO: 11 sets forth the polypeptide sequence of human IL-1R1 (CD121a).

SEQ ID NO: 12 sets forth the polypeptide sequence of human IL-1RAP.

SEQ ID NO: 13 sets forth the polypeptide sequence of human IFNAR1.

SEQ ID NO: 14 sets forth the polypeptide sequence of human IFNAR2.

SEQ ID NO: 15 sets forth the polypeptide sequence of human IL-1RL2.

SEQ ID NO: 16 sets forth the polypeptide sequence of human TLR1 (CD281).

SEQ ID NO: 17 sets forth the polypeptide sequence of human TLR2 (CD282).

SEQ ID NO: 18 sets forth the polypeptide sequence of human TLR3 (CD283).

SEQ ID NO: 19 sets forth the polypeptide sequence of human TLR4 (CD284).

SEQ ID NO: 20 sets forth the polypeptide sequence of human TLR5 (CD285).

SEQ ID NO: 21 sets forth the polypeptide sequence of human TLR6 (CD286).

SEQ ID NO: 22 sets forth the polypeptide sequence of human TLR7 (CD287).

SEQ ID NO: 23 sets forth the polypeptide sequence of human TLR8 (CD288).

SEQ ID NO: 24 sets forth the polypeptide sequence of human TLR9 (CD289).

SEQ ID NO: 25 sets forth the polypeptide sequence of human TLR10 (CD290).

SEQ ID NO: 26 sets forth the polypeptide sequence of a fusion protein comprising the extracellular domain of human TGFβR1 and the transmembrane and intracellular domain of human IL-12Rβ1.

SEQ ID NO: 27 sets forth the polypeptide sequence of a fusion protein comprising the extracellular domain of human TGFβR2 and the transmembrane and intracellular domain of human IL-12Rβ2.

SEQ ID NO: 28 sets forth the polypeptide sequence of a fusion protein comprising the extracellular domain of human TGFβR2 and the transmembrane and intracellular domain of human IL-12Rβ2, a polypeptide cleavage sequence, and the extracellular domain of human TGFβR1 and the transmembrane and intracellular domain of human IL-12Rβ1.

SEQ ID NO: 29 sets forth the polypeptide sequence of a fusion protein comprising a chimeric antigen receptor, a polypeptide cleavage sequence, the extracellular domain of human TGFβR2 and the transmembrane and intracellular domain of human IL-12Rβ2, a polypeptide cleavage sequence, and the extracellular domain of human TGFβR1 and the transmembrane and intracellular domain of human IL-12Rβ1.

SEQ ID NO: 30 sets forth the polypeptide sequence of a fusion protein comprising a chimeric antigen receptor, a polypeptide cleavage sequence, the extracellular domain of human TGFβR2 and the transmembrane and intracellular domain of human IL-12Rβ2, a polypeptide cleavage sequence, and the extracellular domain of human TGFβR1 and the transmembrane and intracellular domain of human IL-12Rβ1. X represents any scFv sequence.

SEQ ID NO: 31 sets forth the polypeptide sequence of a fusion protein comprising the extracellular domain of human TGFβR1 and the transmembrane and intracellular domain of human IL-2Rγ.

SEQ ID NO: 32 sets forth the polypeptide sequence of a fusion protein comprising the extracellular domain of human TGFβR2 and the transmembrane and intracellular domain of human IL-7Rα.

SEQ ID NO: 33 sets forth the polypeptide sequence of a fusion protein comprising the extracellular domain of human TGFβR2 and the transmembrane and intracellular domain of human IL-7Rα, a polypeptide cleavage sequence, and the extracellular domain of human TGFβR1 and the transmembrane and intracellular domain of human IL-2Rγ.

SEQ ID NO: 34 sets forth the polypeptide sequence of a fusion protein comprising a chimeric antigen receptor, a polypeptide cleavage sequence, the extracellular domain of human TGFβR2 and the transmembrane and intracellular domain of human IL-7Rα, a polypeptide cleavage sequence, and the extracellular domain of human TGFβR1 and the transmembrane and intracellular domain of human IL-2Rγ.

SEQ ID NO: 35 sets forth the polypeptide sequence of a fusion protein comprising a chimeric antigen receptor, a polypeptide cleavage sequence, the extracellular domain of human TGFβR2 and the transmembrane and intracellular domain of human IL-7Rα, a polypeptide cleavage sequence, and the extracellular domain of human TGFβR1 and the transmembrane and intracellular domain of human IL-2Rγ.

SEQ ID NOs: 36-46 set forth the amino acid sequences of various linkers.

SEQ ID NOs: 47-71 set forth the amino acid sequences of protease cleavage sites and self-cleaving polypeptide cleavage sites.

DETAILED DESCRIPTION

A. Overview

Chimeric antigen receptor expressing T cells (CAR T cells) have demonstrated significant anti-tumor activity in hematologic malignancies. Activity in solid tumor indications, however, has been limited in part due to the immunosuppressive solid tumor microenvironment (TME). The overproduction of immunosuppressive cytokines, including TGFβ, by tumor cells and tumor-infiltrating lymphocytes contributes to an immunosuppressive tumor microenvironment. TGFβ inhibits T cell function via a variety of mechanisms. TGFβ is frequently associated with tumor metastasis and invasion, inhibiting the function of immune cells, and poor prognosis in patients with cancer. TGFβ signaling through TGFβR2 in tumor-specific CTLs dampens their function and frequency in the tumor, and blocking TGFβ signaling on CD8$^+$ T cells with monoclonal antibodies results in more rapid tumor surveillance and the presence of many more CTLs at the tumor site. To date, strategies to inhibit TGFβ in a clinical setting have not resulted in significant therapeutic benefits.

The present disclosure generally relates to polypeptides that convert an immunosuppressive TGFβ signal to an immunostimulatory signal and to cells expressing the polypeptides. Without wishing to be bound by any particular theory, the polypeptides contemplated herein are TGFβ signal convertors that comprise the TGFβ binding domains of TGFβR1 and TGFβR2, that when linked to immunostimulatory endodomains and co-expressed in immune effector cells, can convert TGFβ exposure from an immunosuppressive signal to an immunostimulatory one that stimulates immune effector cell activity and function. Coexpression of TGFβ signal convertor polypeptides in immune effector cells renders the cells resistant to the immunosuppressive impacts of TGFβ, e.g., by restoring or increasing proinflammatory cytokine secretion. In particular preferred embodiments, the TGFβ signal convertor polypeptide is referred to as a chimeric TGFβ receptor or CTBR.

In various embodiments, the present disclosure contemplates, in part, polypeptides that convert an immunosuppressive TGFβ signal to an immunostimulatory signal mediated through or by one or more intracellular domains of one or more immune receptors.

In various embodiments, the present disclosure contemplates, in part, polypeptides that convert an immunosuppressive TGFβ signal to an immunostimulatory signal mediated through or by one or more intracellular domains of one or more cytokine receptors.

In various embodiments, the present disclosure contemplates, in part, polypeptides that convert an immunosuppressive TGFβ signal to an immunostimulatory signal mediated through or by one or more intracellular domains of one or more interleukin receptors.

In various embodiments, the present disclosure contemplates, in part, polypeptides that convert an immunosuppressive TGFβ signal to an immunostimulatory signal mediated through or by one or more intracellular domains of one or more pattern recognition receptors.

In various embodiments, the present disclosure contemplates, in part, polypeptides that convert an immunosuppressive TGFβ signal to an immunostimulatory signal mediated through or by one or more intracellular domains of one or more toll-like receptors.

In particular embodiments, the present disclosure contemplates, in part, a polypeptide comprising a TGFβR1 extracellular domain that binds TGFβ, a transmembrane domain and one or more intracellular domains of one or more immune receptors; and a polypeptide comprising a TGFβR2 extracellular domain that binds TGFβ, a transmembrane domain and one or more intracellular domains of one or more immune receptors. In one embodiment, the polypeptides are linked to each other by a polypeptide cleavage signal, e.g., a 2A polypeptide cleavage signal.

In particular embodiments, the present disclosure contemplates, in part, an immune effector cell, e.g., CAR T cell, that expresses a polypeptide comprising a TGFβR1 extracellular domain that binds TGFβ, a transmembrane domain and one or more intracellular domains of one or more immune receptors; and a polypeptide comprising a TGFβR2 extracellular domain that binds TGFβ, a transmembrane domain and one or more intracellular domains of one or more immune receptors.

In particular embodiments, the transmembrane domains and intracellular signaling domains are isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR9 receptor, or a TLR10 receptor.

In particular embodiments, the transmembrane domains and intracellular signaling domains are isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR9, or TLR10.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

A "target antigen" or "target antigen of interest" is an antigen that a binding domain contemplated herein, is designed to bind. In particular embodiments, the target antigen is selected from the group consisting of: alpha folate receptor, 5T4, αvβ6 integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGEL HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Mucl, Muc16, NCAM, NKG2D Ligands, NY-ESO-1, PRAME, PSCA, PSMA, ROR1, SSX, Survivin, STn, TAG72, TEMs, VEGFR2, and WT-1.

In one embodiment, the antigen is an MHC-peptide complex, such as a class I MHC-peptide complex or a class II MHC-peptide complex.

As used herein, the terms, "binding domain," "extracellular domain," "antigen binding domain," "extracellular binding domain," "extracellular antigen binding domain," "antigen-specific binding domain," and "extracellular antigen specific binding domain," are used interchangeably and provide a polypeptide with the ability to specifically bind to the target antigen of interest. The binding domain may be derived either from a natural, synthetic, semi-synthetic, or recombinant source. Illustrative examples of binding domains include, but are not limited to antibodies and antigen binding fragments thereof, FN3 domains and DARPins.

The terms "specific binding affinity" or "specifically binds" or "specifically bound" or "specific binding" or "specifically targets" as used herein, describe binding of an antibody or antigen binding fragment thereof to a target antigen at greater binding affinity than background binding. A binding domain "specifically binds" to a target antigen, if it binds to or associates with the antigen with an affinity or $K_a$ (i.e., an equilibrium association constant of a particular binding interaction with units of 1/M) of, for example, greater than or equal to about $10^5$ $M^{-1}$. In certain embodiments, a binding domain (or a fusion protein thereof) binds to a target with a $K_a$ greater than or equal to about $10^6$ $M^{-1}$, $10^7$ $M^{-1}$, $10^8 M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains (or single chain fusion proteins thereof) refers to those binding domains with a $K_a$ of at least $10^7 M^{-1}$, at least $10^8 M^{-1}$, at least $10^9 M^{-1}$, at least $10^{10}$ $M^{-1}$, at least $10^{11}$ $M^{-1}$, at least $10^{12}$ $M^{-1}$, at least $10^{13} M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of binding domain polypeptides can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, NJ, or optical biosensor technology such as the EPIC system or EnSpire that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

An "antibody" refers to a binding agent that is a polypeptide comprising at least a light chain or heavy chain immunoglobulin variable region which specifically recognizes and binds an epitope of an antigen, such as a lipid, carbohydrate, polysaccharide, glycoprotein, peptide, or nucleic acid containing an antigenic determinant, such as those recognized by an immune cell.

An "epitope" or "antigenic determinant" refers to the region of an antigen to which a binding agent binds.

Antibodies include antigen binding fragments thereof, such as Camel Ig, Ig NAR, Fab fragments, Fab' fragments, F(ab)'$_2$ fragments, F(ab)'$_3$ fragments, Fv, single chain Fv proteins ("scFv"), bis-scFv, (scFv)$_2$, minibodies, diabodies, triabodies, tetrabodies, disulfide stabilized Fv proteins ("dsFv"), and single-domain antibody (sdAb, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

As would be understood by the skilled person and as described elsewhere herein, a complete antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ. Mammalian light chains are classified as λ or κ. Immunoglobulins comprising the α, δ, ε, γ, and μ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al. (Wu, TT and Kabat, E. A., *J Exp Med.* 132(2):211-50, (1970); Borden, P. and Kabat E. A., *PNAS,* 84: 2440-2443 (1987); (see, Kabat et al., *Sequences of Proteins of Immunological Interest*, U.S. Department of Health and Human Services, 1991, which is hereby incorporated by reference), or by structure according to Chothia et al (Chothia, C. and Lesk, A. M., *J Mol. Biol.,* 196(4): 901-917 (1987), Chothia, C. et al, *Nature,* 342: 877-883 (1989)).

Illustrative examples of rules for predicting light chain CDRs include: CDR-L1 starts at about residue 24, is preceded by a Cys, is about 10-17 residues, and is followed by a Trp (typically Trp-Tyr-Gln, but also, Trp-Leu-Gln, Trp-Phe-Gln, Trp-Tyr-Leu); CDR-L2 starts about 16 residues after the end of CDR-L1, is generally preceded by Ile-Tyr, but also, Val-Tyr, Ile-Lys, Ile-Phe, and is 7 residues; and CDR-L3 starts about 33 residues after the end of CDR-L2, is preceded by a Cys, is 7-11 residues, and is followed by Phe-Gly-XXX-Gly (XXX is any amino acid) [SEQ ID NO:73].

Illustrative examples of rules for predicting heavy chain CDRs include: CDR-H1 starts at about residue 26, is preceded by Cys-XXX-XXX-XXX (SEQ ID NO:74), is 10-12 residues and is followed by a Trp (typically Trp-Val, but also, Trp-Ile, Trp-Ala); CDR-H2 starts about 15 residues after the end of CDR-H1, is generally preceded by Leu-Glu-Trp-Ile-Gly (SEQ ID NO:75), or a number of variations, is 16-19 residues, and is followed by Lys/Arg-Leu/Ile/Val/Phe/Thr/Ala-Thr/Ser/Ile/Ala; and CDR-H3 starts about 33 residues after the end of CDR-H2, is preceded by Cys-XXX-XXX (typically Cys-Ala-Arg), is 3 to 25 residues, and is followed by Trp-Gly-XXX-Gly (SEQ ID NO:76).

In one embodiment, light chain CDRs and the heavy chain CDRs are determined according to the Kabat method In one embodiment, light chain CDRs and the heavy chain CDR2 and CDR3 are determined according to the Kabat method, and heavy chain CDR1 is determined according to the AbM method, which is a comprise between the Kabat and Clothia methods, see e.g., Whitelegg N & Rees A R, *Protein Eng.* 2000 Dec; 13(12):819-24 and *Methods Mol Biol.* 2004; 248:51-91. Programs for predicting CDRs are publicly available, e.g., AbYsis (www.bioinf.org.uk/abysis/).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_L$" or "VL" refer to the variable region of an immunoglobulin light chain, including that of an antibody, Fv, scFv, dsFv, Fab, or other antibody fragment as disclosed herein.

References to "$V_H$" or "VH" refer to the variable region of an immunoglobulin heavy chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In particular preferred embodiments, an antigen-specific binding domain is a chimeric antibody or antigen binding fragment thereof.

In particular embodiments, the antibody is a human antibody (such as a human monoclonal antibody) or antigen binding fragment thereof that specifically binds to a target antigen. Human antibodies can be constructed by combining Fv clone variable domain sequence(s) selected from human-derived phage display libraries with known human constant domain sequences(s) as described above. Alternatively, human monoclonal antibodies may be made by the hybridoma method. Human myeloma and mouse-human heteromyeloma cell lines for the production of human monoclonal antibodies have been described, for example, by Kozbor *J Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991). In addition, transgenic animals (e.g., mice) can be used to produce a full repertoire of human antibodies in the absence of endogenous immunoglobulin production. See, e.g., Jakobovits et al., *PNAS USA,* 90: 2551 (1993); Jakobovits et al., *Nature,* 362: 255 (1993); Bruggermann et al., *Year in Immunol.,* 7: 33 (1993). Gene shuffling can also be used to derive human antibodies from non-human, e.g., rodent antibodies, where the human antibody has similar affinities and specificities to the starting non-human antibody. See PCT WO 93/06213 published Apr. 1, 1993. Unlike traditional humanization of non-human antibodies by CDR grafting, this technique provides completely human antibodies, which have no FR or CDR residues of non-human origin.

A "humanized" antibody is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. Humanized or other monoclonal antibodies can have additional conservative amino acid substitutions, which have substantially no effect on antigen binding or other immunoglobulin functions. Humanized antibodies can be constructed by means of genetic engineering (see for example, U.S. Pat. No. 5,585,089).

"Camel Ig" or "camelid VHH" as used herein refers to the smallest known antigen-binding unit of a heavy chain antibody (Koch-Nolte, et al, *FASEB J.,* 21: 3490-3498 (2007)). A "heavy chain antibody" or a "camelid antibody" refers to an antibody that contains two VH domains and no light chains (Riechmann L. et al, *J. Immunol. Methods* 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulfide bridges, and patterns of intra-loop hydrogen bonds.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *PNAS USA* 90: 6444-6448 (1993). Triabodies and tetrabodies are also described in Hudson et al., *Nat. Med.* 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al, *Trends in Biotechnology,* 21(11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies,* vol. 113, Rosenburg and Moore eds., (Springer-Verlag, New York, 1994), pp. 269-315.

Single chain antibodies may be cloned from the V region genes of a hybridoma specific for a desired target. The production of such hybridomas has become routine. A technique which can be used for cloning the variable region heavy chain ($V_H$) and variable region light chain ($V_L$) has been described, for example, in Orlandi et al., *PNAS,* 1989; 86: 3833-3837.

A "linker" refers to a plurality of amino acid residues between the various polypeptide domains, e.g., between $V_H$ and $V_L$ domains, added for appropriate spacing and conformation of the molecule. In particular embodiments, the linker is a variable region linking sequence. A "variable region linking sequence," is an amino acid sequence that connects the $V_H$ and $V_L$ domains and provides a spacer function compatible with interaction of the two sub-binding domains so that the resulting polypeptide retains a specific binding affinity to the same target molecule as an antibody that comprises the same light and heavy chain variable regions. In particular embodiments, a linker separates one or more heavy or light chain variable domains, hinge domains, multimerization domains, transmembrane domains, co-stimulatory domains, and/or primary signaling domains.

Illustrated examples of linkers suitable for use in particular embodiments contemplated herein include, but are not limited to the following amino acid sequences: GGG; DGGGS (SEQ ID NO: 36); TGEKP (SEQ ID NO: 37) (see, e.g., Liu et al., PNAS 5525-5530 (1997)); GGRR (SEQ ID NO: 38) (Pomerantz et al. 1995, supra); (GGGGS)$_n$ wherein n=1, 2, 3, 4 or 5 (SEQ ID NO: 39) (Kim et al., PNAS 93, 1156-1160 (1996.); EGKSSGSGSESKVD (SEQ ID NO: 40) (Chaudhary et al., 1990, Proc. Natl. Acad. Sci. U.S.A. 87:1066-1070); KESGSVSSEQLAQFRSLD (SEQ ID NO: 41) (Bird et al., 1988, Science 242:423-426), GGRRGGGS (SEQ ID NO: 42); LRQRDGERP (SEQ ID NO: 43); LRQKDGGGSERP (SEQ ID NO: 44); LRQKD(GGGS)$_2$ERP (SEQ ID NO: 45). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods. In one embodiment, the linker comprises the following amino acid sequence: GSTSGSGKPGSGEGSTKG (SEQ ID NO: 46) (Cooper et al., *Blood*, 101(4): 1637-1644 (2003)).

A "spacer domain," refers to a polypeptide that separates two domains. In one embodiment, a spacer domain moves an antigen binding domain away from the effector cell surface to enable proper cell/cell contact, antigen binding and activation (Patel et al., *Gene Therapy*, 1999; 6: 412-419). In particular embodiments, a spacer domain separates one or more heavy or light chain variable domains, multimerization domains, transmembrane domains, co-stimulatory domains, and/or primary signaling domains. The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

A "hinge domain," refers to a polypeptide that plays a role in positioning the antigen binding domain away from the effector cell surface to enable proper cell/cell contact, antigen binding and activation. In particular embodiments, polypeptides may comprise one or more hinge domains between the binding domain and the multimerization domain, between the binding domain and the transmembrane domain (TM), or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region.

An "altered hinge region" refers to (a) a naturally occurring hinge region with up to 30% amino acid changes (e.g., up to 25%, 20%, 15%, 10%, or 5% amino acid substitutions or deletions), (b) a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). In certain embodiments, one or more cysteine residues in a naturally occurring immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

A "multimerization domain," as used herein, refers to a polypeptide that preferentially interacts or associates with another different polypeptide directly or via a bridging molecule, wherein the interaction of different multimerization domains substantially contributes to or efficiently promotes multimerization (i.e., the formation of a dimer, trimer, or multipartite complex, which may be a homodimer, heterodimer, homotrimer, heterotrimer, homomultimer, heteromultimer). A multimerization domain may be derived either from a natural, synthetic, semi-synthetic, or recombinant source.

Illustrative examples of multimerization domains suitable for use in particular embodiments contemplated herein include an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, or variants thereof.

A "bridging factor" refers to a molecule that associates with and that is disposed between two or more multimerization domains. In particular embodiments, multimerization domains substantially contribute to or efficiently promote formation of a polypeptide complex only in the presence of a bridging factor. In particular embodiments, multimerization domains do not contribute to or do not efficiently promote formation of a polypeptide complex in the absence of a bridging factor. Illustrative examples of bridging factors suitable for use in particular embodiments contemplated herein include, but are not limited to rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Rapamycin analogs (rapalogs) include, but are not limited to those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. In a preferred embodiment, the rapalog is AP21967 derivatives (also known as C-16-(S)-7-methylindolerapamycin, IC$_{50}$=10 nM, a chemically modified non-immunosuppressive rapamycin analogue).

A "substantially reduced immunosuppressive effect" refers to at least less than 0.1 to 0.005 times the immunosuppressive effect observed or expected for the same dose measured either clinically or in an appropriate in vitro (e.g., inhibition of T cell proliferation) or in vivo surrogate of human immunosuppressive activity.

As used herein, "anchor domain" refers to an amino acid sequence or other molecule that promotes tethering, anchoring or association of a dimerizable receptor to a cell surface. Exemplary anchor domains include an amino acid sequence with a structure that is stable in a cell membrane or an amino acid sequence that promotes the addition of a glycolipid (also known as glycosyl phosphatidylinositols or GPIs), or the like. In certain embodiments, an anchor domain is a hydrophobic domain (e.g., transmembrane domain) or a GPI signal sequence. In some embodiments, a nucleic acid molecule encoding a polypeptide contemplated herein comprises an anchor domain, optionally wherein the anchor domain is a GPI molecule.

A "transmembrane domain" or "TM domain" is a domain that anchors a polypeptide to the plasma membrane of a cell.

The TM domain may be derived either from a natural, synthetic, semi-synthetic, or recombinant source.

An "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

The term "effector function" or "effector cell function" refers to a specialized function of an immune effector cell. Effector function includes, but is not limited to, activation, cytokine production, proliferation and cytotoxic activity, including the release of cytotoxic factors, or other cellular responses elicited with antigen binding to the receptor expressed on the immune effector cell.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal.

A "primary signaling domain" refers to a signaling domain that regulates the primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are suitable for use in particular embodiments include, but are not limited to those derived from FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules from which co-stimulatory domains may be isolated include, but are not limited to: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

An "immune disorder" refers to a disease that evokes a response from the immune system. In particular embodiments, the term "immune disorder" refers to a cancer, an autoimmune disease, or an immunodeficiency. In one embodiment, immune disorders encompasse infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

"Antigen negative" refers to a cell that does not express antigen or expresses a neglible amount of antigen that is undetectable. In one embodiment, antigen negative cells do not bind receptors directed to the antigen. In one embodiment, antigen negative cells do not substantially bind receptors directed to the antigen.

An "autoimmune disease" refers to a disease in which the body produces an immunogenic (i.e., immune system) response to some constituent of its own tissue. In other words, the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, and diabetes.

An "infectious disease" refers to a disease that can be transmitted from person to person or from organism to organism, and is caused by a microbial or viral agent (e.g., common cold). Infectious diseases are known in the art and include, for example, hepatitis, sexually transmitted diseases (e.g., Chlamydia, gonorrhea), tuberculosis, HIV/AIDS, diphtheria, hepatitis B, hepatitis C, cholera, and influenza.

As used herein, the terms "individual" and "subject" are often used interchangeably and refer to any animal that exhibits a symptom of cancer or other immune disorder that can be treated with the compositions and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have, have been diagnosed with, or are at risk or having, cancer or another immune disorder.

As used herein, the term "patient" refers to a subject that has been diagnosed with cancer or another immune disorder that can be treated with the compositions and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction of the disease or condition, or the delaying of the progression of the disease or condition, e.g., delaying tumor outgrowth. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, cytokine secretion, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in a cell, as compared to the response caused by either vehicle, a control molecule/composition, or the response in a particular cell lineage. A comparable response is one that is not significantly different or measurable different from the reference response C. TGFβ Signal Convertors (Chimeric TGFβ Receptors)

In particular embodiments, a TGFβ signal convertor that transduces an immunostimulatory signal upon exposure to TGFβ, including but not limited to TGFβ1, is contemplated. As used herein, the term "TGFβ signal convertor" refers to one or more non-naturally occurring polypeptides that converts TGFβ immunosuppressive signals from the tumor microenvironment to immunostimulatory signals in a T cell, e.g., stimulating immune effector cell activity and function, increasing production and/or secretion of proinflammatory cytokines. In particular embodiments, the term "TGFβ signal convertor" is used interchangeably with the term "chimeric TGFβ receptor(s)" or "CTBR" or "CTBR signal convertor."

In particular embodiments, the CTBR signal convertor is a polypeptide comprising an extracellular TGFβ-binding domain of TGFβR2, a transmembrane domain, an intracellular signaling domain of an immune receptor including, but not limited to a cytokine receptor, an interleukin receptor, a pattern recognition receptor, and a toll-like receptor; a polypeptide cleavage signal; and an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

In particular embodiments, the CTBR signal convertor is a fusion polypeptide that comprises a first polypeptide comprising an extracellular TGFβ-binding domain of TGFβR2, a transmembrane domain, an intracellular signaling domain of an immune receptor including, but not limited to a cytokine receptor, an interleukin receptor, a pattern recognition receptor, and a toll-like receptor; a polypeptide cleavage signal; and a second polypeptide comprising an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

In other particular embodiments, the CTBR signal convertor is a complex of polypeptides comprising a polypeptide comprising an extracellular TGFβ-binding domain of TGFβR2, a transmembrane domain, and an intracellular signaling domain of an immune receptor including, but not limited to a cytokine receptor, an interleukin receptor, a pattern recognition receptor, and a toll-like receptor; and a polypeptide comprising an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

As used herein, the term "immune receptor" refers to a receptor that is expressed on the surface of an immune cell that modulates an immune response upon binding its cognate ligand. Immune receptors suitable for use in particular embodiments include, but are not limited to: cytokine receptors, interleukin receptors, pattern recognition receptors, and toll-like receptors, wherein signaling through the immune receptor stimulates an immune response.

Illustrative examples of immune receptor transmembrane and intracellular signaling domains that can be used in particular embodiments contemplated herein include, but are not limited to transmembrane and intracellular signaling domains isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR5 receptor, or a TLR10 receptor.

Further illustrative examples of immune receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR5, or TLR10.

Illustrative examples of cytokine receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, and IL-1RL2.

Illustrative examples of interleukin receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, and IL-1RL2.

Illustrative examples of toll-like receptor transmembrane and intracellular signaling domains that can be used in particular embodiments contemplated herein include, but are not limited to transmembrane and intracellular signaling domains isolated from TLR1, TLR2, TLR3, TLR4, TLR5, TLR6, TLR7, TLR8, TLR9, and TLR10.

1. CTBR12 Signal Convertor

Interleukin-12 (IL-12) is a cytokine that promotes T cell function and activity by, in part, increasing IFNγ expression, increasing T cell proliferation, and potentiating IL-12 signaling. IL-12 binds interleukin 12 receptor, beta 1 (IL-12Rβ1, also known as CD212) and interleukin 12 receptor, beta 2 (IL-12Rβ2).

IL-12 signaling through IL-12Rβ1 and IL-12Rβ2 results in STAT3, STAT4, and STAT5 phosphorylation. Phosphorylated STAT3/STAT4 translocates to the nucleus and binds the IFNγ promoter to increase IFNγ expression. Phosphorylated STAT4 also recruits Jun oncogene (c-Jun) to IFNγ promoter to increase IFNγ expression, and potentiates IL-12 signaling by increasing transcription of IL-12Rβ2. STAT5 phosphorylation increases T cell proliferation.

IL-12 signaling also increases expression of interleukin 2 receptor, alpha (IL-2R) by recruiting STAT4 and c-Jun to the promoter of IL-2R, thereby enhancing T cell proliferation.

In various embodiments, one or more immune effector cells, including immune effector cells expressing an engineered antigen receptor, are modified by introducing one or more polynucleotides or vectors encoding a CTBR12 signal convertor. In various embodiments, one or more immune effector cells are modified by introducing one or more polynucleotides or vectors encoding a CTBR12 signal convertor and an engineered antigen receptor.

In particular embodiments, the CTBR12 signal convertor converts an immunosuppressive TGFβ signal to an IL-12-mediated immunostimulatory signal. In particular embodiments a CTBR12 signal convertor contemplated herein comprises: an extracellular TGFβ1-binding domain of TGFβR1, a transmembrane domain, and an IL-12Rβ1 intracellular signaling domain; a polypeptide cleavage signal; and an extracellular TGFβ1-binding domain of TGFβR2, a transmembrane domain, and an IL-12Rβ2 intracellular signaling domain. In particular embodiments a CTBR 12 signal convertor contemplated herein comprises: an extracellular TGFβ1-binding domain of TGFβR1, a transmembrane domain, and an IL-12Rβ2 intracellular signaling domain; a polypeptide cleavage signal; and an extracellular TGFβ1-binding domain of TGFβR2, a transmembrane domain, and an IL-12Rβ1 intracellular signaling domain.

In particular embodiments a CTBR12 signal convertor contemplated herein comprises a fusion polypeptide comprising: a first polypeptide comprising an extracellular TGFβ1-binding domain of TGFβR1, a transmembrane domain, and an IL-12Rβ1 intracellular signaling domain; a polypeptide cleavage signal; and a second polypeptide comprising an extracellular TGFβ1-binding domain of TGFβR2, a transmembrane domain, and an IL-12Rβ2 intracellular signaling domain. In particular embodiments a CTBR12 signal convertor contemplated herein comprises a fusion polypeptide comprising: a first polypeptide comprising an extracellular TGFβ1-binding domain of TGFβR1, a transmembrane domain, and an IL-12Rβ2 intracellular signaling domain; a polypeptide cleavage signal; and a second polypeptide comprising an extracellular TGFβ1-binding domain of TGFβR2, a transmembrane domain, and an IL-12Rβ1 intracellular signaling domain.

In particular embodiments, the CTBR12 signal convertor is a complex of polypeptides comprising a first polypeptide comprising a polypeptide comprising an extracellular TGFβ1-binding domain of TGFβR1, a transmembrane domain, and an IL-12Rβ1 intracellular signaling domain; and a polypeptide comprising an extracellular TGFβ1-binding domain of TGFβR2, a transmembrane domain, and an IL-12Rβ2 intracellular signaling domain. In particular embodiments, the CTBR12 signal convertor is a complex of polypeptides comprising a first polypeptide comprising a polypeptide comprising an extracellular TGFβ1-binding domain of TGFβR1, a transmembrane domain, and an IL-12Rβ2 intracellular signaling domain; and a polypeptide comprising an extracellular TGFβ1-binding domain of TGFβR2, a transmembrane domain, and an IL-12Rβ1 intracellular signaling domain.

In certain embodiments, a polypeptide comprises a transmembrane domain of TGFβR1 or TGFβR2. In certain embodiments, a polypeptide comprises a transmembrane domain of IL-12Rβ1 or IL-12Rβ2. In one embodiment, a polypeptide comprises an extracellular TGFβ1-binding domain of TGFβR1 and an IL-12Rβ1 transmembrane domain and intracellular signaling domain. In one embodiment, a polypeptide comprises an extracellular TGFβ1-binding domain of TGFβR2 and an IL-12Rβ2 transmembrane domain and intracellular signaling domain. In one embodiment, a polypeptide comprises an extracellular TGFβ1-binding domain of TGFβR1 and an IL-12Rβ2 transmembrane domain and intracellular signaling domain. In one embodiment, a polypeptide comprises an extracellular TGFβ1-binding domain of TGFβR2 and an IL-12Rβ1 transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

2. CTBR7 Signal Convertor

Interleukin-7 (IL-7) is a cytokine that promotes T cell function and activity by, in part, improving T cell precursor survival and proliferation. IL-7 binds interleukin 7 receptor alpha (IL-7Rα, also known as CD127) and interleukin 2 receptor, common gamma chain (IL-2Rγ, also known as CD132 and γc). IL-7 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding a CTBR7 signal convertor. In various embodiments, one or more immune effector cells are modified by introducing one or more polynucleotides or vectors encoding a CTBR7 signal convertor and an engineered antigen receptor.

In particular embodiments, the TGFβ signal convertor converts an immunosuppressive TGFβ signal to an IL-7-mediated immunostimulatory signal. In particular embodiments, a CTBR7 signal convertor contemplated herein comprises: an extracellular TGFβ1-binding domain of TGFβR1, a transmembrane domain, and an IL-7Rα intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR7 signal convertor contemplated herein comprises: an extracellular TGFβ1-binding domain of TGFβR1, a transmembrane domain, and an IL-2Rγ intracellular signaling domain; a polypeptide cleavage signal; and an extracellular TGFβ1-binding domain of TGFβR2, a transmembrane domain, and an IL-7Rα intracellular signaling domain.

In particular embodiments a CTBR7 signal convertor contemplated herein comprises a fusion polypeptide comprising: a first polypeptide comprising an extracellular TGFβ1-binding domain of TGFβR1, a transmembrane domain, and an IL-7Rα intracellular signaling domain; a polypeptide cleavage signal; and a second polypeptide comprising an extracellular TGFβ1-binding domain of TGFβR2, a transmembrane domain, and an IL-2Rγ intracellular signaling domain. In particular embodiments, a CTBR7 signal convertor contemplated herein comprises a fusion polypeptide comprising: a first polypeptide comprising an extracellular TGFβ1-binding domain of TGFβR1, a transmembrane domain, and an IL-2Rγ intracellular signaling domain; a polypeptide cleavage signal; and a second polypeptide comprising an extracellular TGFβ1-binding domain of TGFβR2, a transmembrane domain, and an IL-7Rα intracellular signaling domain.

In particular embodiments, the CTBR7 signal convertor is a complex of polypeptides comprising a first polypeptide comprising a polypeptide comprising an extracellular TGFβ1-binding domain of TGFβR1, a transmembrane domain, and an IL-7Rα intracellular signaling domain; and a polypeptide comprising an extracellular TGFβ1-binding domain of TGFβR2, a transmembrane domain, and an IL-2Rγ intracellular signaling domain. In particular embodiments, the CTBR7 signal convertor is a complex of polypeptides comprising a first polypeptide comprising a polypeptide comprising an extracellular TGFβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-7Rα intracellular signaling domain.

In certain embodiments, a polypeptide comprises a transmembrane domain of TGFβR1 or TGFβR2. In certain embodiments, a polypeptide comprises a transmembrane domain of IL-7Rα or IL-2Rγ. In one embodiment, a polypeptide comprises an extracellular TGFβ1-binding domain of TGFβR1 and an IL-7Rα transmembrane domain and intracellular signaling domain. In one embodiment, a polypeptide comprises an extracellular TGFβ1-binding domain of TGFβR2 and an IL-2Rγ transmembrane domain and intracellular signaling domain. In one embodiment, a polypeptide comprises an extracellular TGFβ1-binding domain of TGFβR1 and an IL-2Rγ transmembrane domain and intracellular signaling domain. In one embodiment, a polypeptide comprises an extracellular TGFβ1-binding domain of TGFβR2 and an IL-7Rα transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In one embodiment, the polypeptide cleavage signal is a P2A or T2A viral self-cleaving polypeptide.

3. CTBR15 Signal Convertor

Interleukin-15 (IL-15) is a cytokine that promotes T cell function and activity by, in part, improving T cell precursor survival and proliferation. IL-15 binds with high affinity to IL-15Rα (also known as CD215), which then associates with a complex comprising IL-2Rβ (also known as IL-15R13 and CD122) and IL-2Rγ (also known as CD132 and γc), expressed either on the same cell (cis-presentation) or on a different cell (trans-presentation). IL-15 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding a CTBR15 signal convertor, and optionally, a polynucleotide or vector encoding an IL-15Rα polypeptide. In various embodiments, one or more immune effector cells are modified by introducing one or more polynucleotides or vectors encoding a CTBR15 signal convertor and an engineered antigen receptor, and optionally, a polynucleotide or vector encoding an IL-15Rα polypeptide.

In particular embodiments, the TGFβ signal convertor converts an immunosuppressive TGFβ signal to an IL-15-mediated immunostimulatory signal. In particular embodiments, a CTBR15 signal convertor contemplated herein comprises: an extracellular TGFβ1-binding domain of TGFβR1, a transmembrane domain, and an IL-2Rβ intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR15 signal convertor contemplated herein comprises: an extracellular TGFβ1-binding domain of TGFβR1, a transmembrane domain, and an IL-2Rγ intracellular signaling domain; a polypeptide cleavage signal; and an extracellular TGFβ1-binding domain of TGFβR2, a transmembrane domain, and an IL-2Rβ intracellular signaling domain.

In particular embodiments a CTBR15 signal convertor contemplated herein comprises a fusion polypeptide comprising: a first polypeptide comprising an extracellular TGFβ1-binding domain of TGFβR1, a transmembrane domain, and an IL-2Rβ intracellular signaling domain; a polypeptide cleavage signal; and a second polypeptide comprising an extracellular TGFβ1-binding domain of TGFβR2, a transmembrane domain, and an IL-2Rγ intracellular signaling domain. In particular embodiments, a CTBR15 signal convertor contemplated herein comprises a fusion polypeptide comprising: a first polypeptide comprising an extracellular TGFβ1-binding domain of TGFβR1, a transmembrane domain, and an IL-2Rγ intracellular signaling domain; a polypeptide cleavage signal; and a second polypeptide comprising an extracellular TGFβ1-binding domain of TGFβR2, a transmembrane domain, and an IL-2Rβ intracellular signaling domain.

In particular embodiments, the CTBR15 signal convertor is a complex of polypeptides comprising a first polypeptide comprising a polypeptide comprising an extracellular TGFβ1-binding domain of TGFβR1, a transmembrane domain, and an IL-2Rβ intracellular signaling domain; and a polypeptide comprising an extracellular TGFβ1-binding domain of TGFβR2, a transmembrane domain, and an IL-2Rγ intracellular signaling domain. In particular embodiments, the CTBR15 signal convertor is a complex of polypeptides comprising a first polypeptide comprising a polypeptide comprising an extracellular TGFβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-2Rβ intracellular signaling domain.

In certain embodiments, a polypeptide comprises a transmembrane domain of TGFβR1 or TGFβR2. In certain embodiments, a polypeptide comprises a transmembrane domain of IL-2Rβ or IL-2Rγ. In one embodiment, a polypeptide comprises an extracellular TGFβ1-binding domain of TGFβR1 and an IL-2Rβ transmembrane domain and intracellular signaling domain. In one embodiment, a polypeptide comprises an extracellular TGFβ1-binding domain of TGFβR2 and an IL-2Rγ transmembrane domain and intracellular signaling domain. In one embodiment, a polypeptide comprises an extracellular TGFβ1-binding domain of TGFβR1 and an IL-2Rγ transmembrane domain and intracellular signaling domain. In one embodiment, a polypeptide comprises an extracellular TGFβ1-binding domain of TGFβR2 and an IL-2Rβ transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

4. CTBR21 Signal Convertor

Interleukin-21 (IL-21) is a cytokine that promotes T cell function and activity by, in part, improving T cell precursor survival and proliferation. IL-21 binds to interleukin 21 receptor (IL-21R, also known as CD360) and IL-2Rγ (also known as CD132 and γc). IL-21 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding a CTBR21 signal convertor. In various embodiments, one or more immune effector cells are modified by introducing one or more polynucleotides or vectors encoding a CTBR21 signal convertor and an engineered antigen receptor.

In particular embodiments, the TGFβ signal convertor converts an immunosuppressive TGFβ signal to an IL-21-mediated immunostimulatory signal. In particular embodiments, a CTBR21 signal convertor contemplated herein comprises: an extracellular TGFβ1-binding domain of TGFβR1, a transmembrane domain, and an IL-21R intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR21 signal convertor contemplated herein comprises: an extracellular TGFβ1-binding domain of TGFβR1, a transmembrane domain, and an IL-2Rγ intracellular signaling domain; a polypeptide cleavage signal; and an extracellular TGFβ1-binding domain of TGFβR2, a transmembrane domain, and an IL-21R intracellular signaling domain.

In particular embodiments a CTBR21 signal convertor contemplated herein comprises a fusion polypeptide comprising: a first polypeptide comprising an extracellular TGFβ1-binding domain of TGFβR1, a transmembrane domain, and an IL-21R intracellular signaling domain; a polypeptide cleavage signal; and a second polypeptide comprising an extracellular TGFβ1-binding domain of TGFβR2, a transmembrane domain, and an IL-2Rγ intracellular signaling domain. In particular embodiments, a CTBR21 signal convertor contemplated herein comprises a fusion polypeptide comprising: a first polypeptide comprising an extracellular TGFβ1-binding domain of TGFβR1, a transmembrane domain, and an IL-2Rγ intracellular signaling domain; a polypeptide cleavage signal; and a second polypeptide comprising an extracellular TGFβ1-binding domain of TGFβR2, a transmembrane domain, and an IL-21R intracellular signaling domain.

In particular embodiments, the CTBR21 signal convertor is a complex of polypeptides comprising a first polypeptide comprising a polypeptide comprising an extracellular TGFβ1-binding domain of TGFβR1, a transmembrane domain, and an IL-21R intracellular signaling domain; and a polypeptide comprising an extracellular TGFβ1-binding domain of TGFβR2, a transmembrane domain, and an IL-2Rγ intracellular signaling domain. In particular embodiments, the CTBR21 signal convertor is a complex of polypeptides comprising a first polypeptide comprising a polypeptide comprising an extracellular TGFβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-21R intracellular signaling domain.

In certain embodiments, a polypeptide comprises a transmembrane domain of TGFβR1 or TGFβR2. In certain embodiments, a polypeptide comprises a transmembrane domain of IL-21R or IL-2Rγ. In one embodiment, a polypeptide comprises an extracellular TGFβ1-binding domain of TGFβR1 and an IL-21R transmembrane domain and intracellular signaling domain. In one embodiment, a polypeptide comprises an extracellular TGFβ1-binding domain of TGFβR2 and an IL-2Rγ transmembrane domain and intracellular signaling domain. In one embodiment, a polypeptide comprises an extracellular TGFβ1-binding domain of TGFβR1 and an IL-2Rγ transmembrane domain and intracellular signaling domain. In one embodiment, a polypeptide comprises an extracellular TGFβ1-binding domain of TGFβR2 and an IL-21R transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

5. CTBR18 Signal Convertor

Interleukin-18 (IL-18) is a cytokine that promotes T cell function and activity by, in part, increasing IFNγ expression, increasing T cell proliferation, and protecting against activation induced cell death (AICD). IL-18 binds interleukin 18 receptor 1, (IL-18R1, also known as CD218a) and interleukin 18 receptor accessory protein (IL-18RAP, CD218b).

IL-18 signaling through IL-18R1 and IL-18RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-18 also increases T cell proliferation and protects against AICD.

In various embodiments, one or more immune effector cells, including immune effector cells expressing an engineered antigen receptor, are modified by introducing one or more polynucleotides or vectors encoding a CTBR18 signal convertor. In various embodiments, one or more immune effector cells are modified by introducing one or more polynucleotides or vectors encoding a CTBR18 signal convertor and an engineered antigen receptor.

In particular embodiments, the TGFβ signal convertor converts an immunosuppressive TGFβ signal to an IL-18-mediated immunostimulatory signal. In particular embodiments, a CTBR18 signal convertor contemplated herein comprises: an extracellular TGFβ1-binding domain of TGFβR1, a transmembrane domain, and an IL-18RAP intracellular signaling domain; a polypeptide cleavage signal; and an extracellular TGFβ1-binding domain of TGFβR2, a transmembrane domain, and an IL-18R1 intracellular signaling domain. In particular embodiments, a CTBR18 signal convertor contemplated herein comprises: an extracellular TGFβ1-binding domain of TGFβR1, a transmembrane domain, and an IL-18R1 intracellular signaling domain; a polypeptide cleavage signal; and an extracellular TGFβ1-binding domain of TGFβR2, a transmembrane domain, and an IL-18RAP intracellular signaling domain.

In particular embodiments, a CTBR18 signal convertor contemplated herein comprises a fusion polypeptide comprising: a first polypeptide comprising an extracellular TGFβ1-binding domain of TGFβR1, a transmembrane domain, and an IL-18R1 intracellular signaling domain; a polypeptide cleavage signal; and a second polypeptide comprising an extracellular TGFβ1-binding domain of TGFβR2, a transmembrane domain, and an IL-18RAP intracellular signaling domain. In particular embodiments, a CTBR18 signal convertor contemplated herein comprises a fusion polypeptide comprising: a first polypeptide comprising an extracellular TGFβ1-binding domain of TGFβR1, a transmembrane domain, and an IL-18RAP intracellular signaling domain; a polypeptide cleavage signal; and a second polypeptide comprising an extracellular TGFβ1-binding domain of TGFβR2, a transmembrane domain, and an IL-18R1 intracellular signaling domain.

In particular embodiments, the CTBR18 signal convertor is a complex of polypeptides comprising a first polypeptide comprising a polypeptide comprising an extracellular TGFβ1-binding domain of TGFβR1, a transmembrane domain, and an IL-18RAP intracellular signaling domain; and a polypeptide comprising an extracellular TGFβ1-binding domain of TGFβR2, a transmembrane domain, and an IL-18R1 intracellular signaling domain. In particular embodiments, the CTBR18 signal convertor is a complex of polypeptides comprising a first polypeptide comprising a polypeptide comprising an extracellular TGFβ1-binding domain of TGFβR1, a transmembrane domain, and an IL-18R1 intracellular signaling domain; and a polypeptide comprising an extracellular TGFβ1-binding domain of TGFβR2, a transmembrane domain, and an IL-18RAP intracellular signaling domain.

In certain embodiments, a polypeptide comprises a transmembrane domain of TGFβR1 or TGFβR2. In certain embodiments, a polypeptide comprises a transmembrane domain of IL-18R1 or IL-18RAP. In one embodiment, a polypeptide comprises an extracellular TGFβ1-binding domain of TGFβR1 and an IL-18RAP transmembrane domain and intracellular signaling domain. In one embodiment, a polypeptide comprises an extracellular TGFβ1-binding domain of TGFβR2 and an IL-18R1 transmembrane domain and intracellular signaling domain. In one embodiment, a polypeptide comprises an extracellular TGFβ1-binding domain of TGFβR1 and an IL-18R1 transmembrane domain and intracellular signaling domain. In one embodiment, a polypeptide comprises an extracellular TGFβ1-binding domain of TGFβR2 and an IL-18RAP transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

6. CTBR1 Signal Convertor

Interleukin-1 (IL-1) is a cytokine that promotes T cell function and activity by, in part, increasing IFNγ expression, increasing T cell proliferation, and potentiating protecting against activation induced cell death (AICD). IL-1 binds interleukin 1 receptor 1, (IL-1R1, also known as CD121a) and interleukin 1 receptor accessory protein (IL-1RAP).

IL-1 signaling through IL-1R1 and IL-1RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-1 also increases T cell proliferation and protects against AICD.

In various embodiments, one or more immune effector cells, including immune effector cells expressing an engineered antigen receptor, are modified by introducing one or more polynucleotides or vectors encoding a CTBR1 signal convertor. In various embodiments, one or more immune effector cells are modified by introducing one or more polynucleotides or vectors encoding a CTBR1 signal convertor and an engineered antigen receptor.

In particular embodiments, the TGFβ signal convertor converts an immunosuppressive TGFβ signal to an IL-1-mediated immunostimulatory signal. In particular embodiments, a CTBR1 signal convertor contemplated herein comprises: an extracellular TGFβ1-binding domain of TGFβR1, a transmembrane domain, and an IL-1RAP intracellular signaling domain; a polypeptide cleavage signal; and an extracellular TGFβ1-binding domain of TGFβR2, a transmembrane domain, and an IL-1R1 intracellular signaling domain. In particular embodiments, a CTBR1 signal convertor contemplated herein comprises: an extracellular TGFβ1-binding domain of TGFβR1, a transmembrane domain, and an IL-1R1 intracellular signaling domain; a polypeptide cleavage signal; and an extracellular TGFβ1-binding domain of TGFβR2, a transmembrane domain, and an IL-1RAP intracellular signaling domain.

In particular embodiments, a CTBR1 signal convertor contemplated herein comprises a fusion polypeptide comprising: a first polypeptide comprising an extracellular TGFβ1-binding domain of TGFβR1, a transmembrane domain, and an IL-1R1 intracellular signaling domain; a polypeptide cleavage signal; and a second polypeptide comprising an extracellular TGFβ1-binding domain of TGFβR2, a transmembrane domain, and an IL-1RAP intracellular signaling domain. In particular embodiments, a CTBR1 signal convertor contemplated herein comprises a fusion polypeptide comprising: a first polypeptide comprising an extracellular TGFβ1-binding domain of TGFβR1, a transmembrane domain, and an IL-1RAP intracellular signaling domain; a polypeptide cleavage signal; and a second polypeptide comprising an extracellular TGFβ1-binding domain of TGFβR2, a transmembrane domain, and an IL-1R1 intracellular signaling domain.

In particular embodiments, the CTBR1 signal convertor is a complex of polypeptides comprising a first polypeptide comprising a polypeptide comprising an extracellular TGFβ1-binding domain of TGFβR1, a transmembrane domain, and an IL-1RAP intracellular signaling domain; and a polypeptide comprising an extracellular TGFβ1-binding domain of TGFβR2, a transmembrane domain, and an IL-1R1 intracellular signaling domain. In particular embodiments, the CTBR1 signal convertor is a complex of polypeptides comprising a first polypeptide comprising a polypeptide comprising an extracellular TGFβ1-binding domain of TGFβR1, a transmembrane domain, and an IL-1R1 intracellular signaling domain; and a polypeptide comprising an extracellular TGFβ1-binding domain of TGFβR2, a transmembrane domain, and an IL-1RAP intracellular signaling domain.

In certain embodiments, a polypeptide comprises a transmembrane domain of TGFβR1 or TGFβR2. In certain embodiments, a polypeptide comprises a transmembrane domain of IL-1R1 or IL-1RAP. In one embodiment, a polypeptide comprises an extracellular TGFβ1-binding domain of TGFβR1 and an IL-1RAP transmembrane domain and intracellular signaling domain. In one embodiment, a polypeptide comprises an extracellular TGFβ1-binding domain of TGFβR2 and an IL-1R1 transmembrane domain and intracellular signaling domain. In one embodiment, a polypeptide comprises an extracellular TGFβ1-binding domain of TGFβR1 and an IL-1R1 transmembrane domain and intracellular signaling domain. In one embodiment, a polypeptide comprises an extracellular TGFβ1-binding domain of TGFβR2 and an IL-1RAP transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

7. CTBR. TLR Signal Convertor

Toll like receptors (TLR1 through TLR10) are pattern recognition receptors that detect invading pathogens and activate the innate and adaptive immune responses. Activation of TLRs by various ligands leads to induction of a pro-inflammatory transcriptional program and expression of multiple inflammatory cytokines.

TLR signaling occurs via homodimerization of TLR signaling domains leading to activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase inflammatory cytokine production and induce proliferation. TLR activation can also lead to the activation of IRF3 and IRF7 transcription factors.

In various embodiments, one or more immune effector cells, including immune effector cells expressing an engineered antigen receptor, are modified by introducing one or more polynucleotides or vectors encoding a CTBR.TLR signal convertor. In various embodiments, one or more immune effector cells are modified by introducing one or more polynucleotides or vectors encoding a CTBR.TLR signal convertor and an engineered antigen receptor.

In particular embodiments, the TGFβ signal convertor converts an immunosuppressive TGFβ signal to a TLR-mediated immunostimulatory signal. In particular embodiments, a CTBR.TLR signal convertor contemplated herein comprises: an extracellular TGFβ1-binding domain of TGFβR1, a transmembrane domain, and a TLR intracellular signaling domain; a polypeptide cleavage signal; and an extracellular TGFβ1-binding domain of TGFβR2, a transmembrane domain, and an identical TLR signaling domain.

In particular embodiments, a CTBR.TLR signal convertor contemplated herein comprises a fusion polypeptide comprising: a first polypeptide comprising an extracellular TGFβ1-binding domain of TGFβR1, a transmembrane domain, and a TLR intracellular signaling domain; a polypeptide cleavage signal; and a second polypeptide comprising an extracellular TGFβ1-binding domain of TGFβR2, a transmembrane domain, and an identical TLR signaling domain.

In particular embodiments, the CTBR.TLR signal convertor is a complex of polypeptides comprising a first polypeptide comprising a polypeptide comprising an extracellular TGFβ1-binding domain of TGFβR1, a transmembrane domain, and a TLR intracellular signaling domain; and a polypeptide comprising an extracellular TGFβ1-binding domain of TGFβR2, a transmembrane domain, and an identical TLR intracellular signaling domain.

In certain embodiments, a polypeptide comprises a transmembrane domain of TGFβR1 or TGFβR2. In certain embodiments, a polypeptide comprises a transmembrane domain of a TLR. In one embodiment, a polypeptide comprises an extracellular TGFβ1-binding domain of TGFβR1 and a TLR transmembrane domain and intracellular signaling domain. In one embodiment, a polypeptide comprises an extracellular TGFβ1-binding domain of TGFβR2 and a TLR transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

D. Engineered Antigen Receptors

In particular embodiments, a polypeptide comprises an engineered antigen receptor, a polypeptide cleavage signal and a CTBR. In other particular embodiments, a polynucleotide or vector encoding a CTBR is introduced into an immune effector cell that comprises an engineered antigen receptor. Without wishing to be bound by any particular theory, it is contemplated in particular embodiments, that any mechanism known in the art may be used to introduce and co-express an engineered antigen receptor and a CTBR in the same immune effector cell or population of cells to increase the resistance of the immune effector cells to the TME and potentiate and increase the efficiency, potency, and durability of the immune effector cell response.

In particular embodiments, immune effector cells contemplated herein comprise an engineered antigen receptor and a CTBR. In particular embodiments, the engineered antigen receptor is an engineered T cell receptor (TCR), a chimeric antigen receptor (CAR), a DARIC receptor or components thereof, or a zetakine.

1. Engineered TCRs

In particular embodiments, immune effector cells contemplated herein comprise an engineered TCR and a CTBR signal convertor. In one embodiment, T cells are engineered by introducing a polynucleotide or vector encoding an engineered TCR and a CTBR signal convertor separated by one or more polypeptide cleavage signals. In one embodiment, T cells are engineered by introducing a polynucleotide or vector encoding an engineered TCR and a polynucleotide or vector encoding a CTBR signal convertor. In one embodiment, T cells are engineered to express an engineered TCR are further engineered by introducing a polynucleotide or vector encoding a CTBR signal convertor.

Naturally occurring T cell receptors comprise two subunits, an alpha chain and a beta chain subunit, each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy.

In one embodiment, T cells are modified by introducing a TCR subunit has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the alpha chain or beta chain of a TCR so long as the attached additional polypeptide does not interfere with the ability of the alpha chain or beta chain to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to alpha folate receptor, alpha folate receptor, 5T4, $\alpha v\beta 6$ integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FR$\alpha$, GD2, GD3, Glypican-3 (GPC3), HLA-A1+MAGEL HLA-A2+MAGE1, HLA-A3+ MAGE1, HLA-A1+NY-ESO-1, HLA-A2+NY-ESO-1, HLA-A3+NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAIVIE, PSCA, PSMA, ROR1, SSX, Survivin, TAG72, TEMs, VEGFR2, and WT-1.

2. Chimeric Antigen Receptors

In various embodiments, immune effector cells express CARs that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

In particular embodiments, immune effector cells contemplated herein comprise CAR and a CTBR signal convertor. In one embodiment, T cells are engineered by introducing a polynucleotide or vector encoding a CAR and a CTBR signal convertor separated by one or more polypeptide cleavage signals. In one embodiment, T cells are engineered by introducing a polynucleotide or vector encoding a CAR and a polynucleotide or vector encoding a CTBR signal convertor. In one embodiment, T cells are engineered to express a CAR are further engineered by introducing a polynucleotide or vector encoding a CTBR signal convertor.

In various embodiments, a CAR comprises an extracellular domain that binds to a specific target antigen (also referred to as a binding domain or antigen-specific binding domain), a transmembrane domain and an intracellular signaling domain. The main characteristic of CARs is their ability to redirect immune effector cell specificity, thereby triggering proliferation, cytokine production, phagocytosis or production of molecules that can mediate cell death of the target antigen expressing cell in a major histocompatibility (WIC) independent manner, exploiting the cell specific targeting abilities of monoclonal antibodies, soluble ligands or cell specific coreceptors.

In particular embodiments, CARs comprise an extracellular binding domain that specifically binds to a target polypeptide, e.g., target antigen, expressed on tumor cell. As used herein, the terms, "binding domain," "extracellular domain," "extracellular binding domain," "antigen binding domain," "antigen-specific binding domain," and "extracellular antigen specific binding domain," are used interchangeably and provide a chimeric receptor, e.g., a CAR or DARIC, with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the CAR comprises an extracellular domain that binds an antigen selected from the group consisting of: alpha folate receptor, 5T4, $\alpha v\beta 6$ integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FR$\alpha$, GD2, GD3, Glypican-3 (GPC3), HLA-A1+MAGEL HLA-A2+MAGE1, HLA-A3+MAGE1, HLA-A1+NY-ESO-1, HLA-A2+NY-ESO-1, HLA-A3+NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In certain embodiments, the CARs comprise linker residues between the various domains. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In particular embodiments, CARs comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 of IgG1, IgG4, or IgD.

In one embodiment, the binding domain of the CAR is linked to one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8a, and CD4, which may be wild-type hinge regions from these molecules or may be altered. In another embodiment, the hinge domain comprises a CD8a hinge region.

In one embodiment, the hinge is a PD-1 hinge or CD152 hinge.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a CAR comprises a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In particular embodiments, a CAR comprises an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, a CAR comprises an intracellular signaling domain that comprises one or more "costimulatory signaling domains" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

In particular embodiments, a CAR comprises one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

Illustrative examples of such costimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more costimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CSPG4, PSCA, ROR1, and TAG72; a transmembrane domain isolated from a polypeptide selected from the group consisting of: CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FCRβ, CD3γ, CD3δ, CD3ε, CD3, CD22, CD79a, CD79b, and CD66d.

3. DARIC

In particular embodiments, immune effector cells comprise one or more chains of a DARIC receptor. As used herein, the term "DARIC receptor" refers to a multi-chain engineered antigen receptor.

In particular embodiments, immune effector cells contemplated herein comprise one or more chains of a DARIC receptor and a CTBR signal convertor. In one embodiment, T cells are engineered by introducing a polynucleotide or vector encoding one or more chains of a DARIC receptor and a CTBR signal convertor separated by one or more polypeptide cleavage signals. In one embodiment, T cells are engineered by introducing a polynucleotide or vector encoding one or more chains of a DARIC receptor and a polynucleotide or vector encoding a CTBR signal convertor. In one embodiment, T cells are engineered to express one or more chains of a DARIC receptor are further engineered by introducing a polynucleotide or vector encoding a CTBR signal convertor.

Illustrative examples of DARIC architectures and components are disclosed in PCT Publication No. WO2015/017214 and U.S. Patent Publication No. 20150266973, each of which is incorporated here by reference in its entirety.

In one embodiment, a donor repair template comprises the following DARIC components: a signaling polypeptide comprising a first multimerization domain, a first transmembrane domain, and one or more intracellular co-stimulatory signaling domains and/or primary signaling domains; and a binding polypeptide comprising a binding domain, a second multimerization domain, and optionally a second transmembrane domain. A functional DARIC comprises a bridging factor that promotes the formation of a DARIC receptor complex on the cell surface with the bridging factor associated with and disposed between the multimerization domains of the signaling polypeptide and the binding polypeptide.

In particular embodiments, the first and second multimerization domains associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, and any combination thereof.

Illustrative examples of rapamycin analogs (rapalogs) include those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. In one embodiment, "substantially reduced immunosuppressive effect" refers to a rapalog having an EC50 value in such an in vitro assay that is at least 10 to 250 times larger than the EC50 value observed for rapamycin in the same assay.

Other illustrative examples of rapalogs include, but are not limited to everolimus, novolimus, pimecrolimus, ridaforolimus, tacrolimus, temsirolimus, umirolimus, and zotarolimus.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT 1, or RAFT) from human and other species; yeast proteins including Tor1 and Tor2; and a Candida FRAP homolog. Information concerning the nucleotide sequences, cloning, and other aspects of these proteins is already known in the art. For example, a protein sequence accession number for a human mTOR is GenBank Accession No. L34075.1 (Brown et al., Nature 369:756, 1994).

FRB domains suitable for use in particular embodiments contemplated herein generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. An FRB domain for use in DARICs contemplated in particular embodiments will be capable of binding to a complex of an FKBP protein bound to rapamycin or a rapalog thereof. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain." Information concerning the nucleotide sequences, cloning, and other aspects of various FKBP species is known in the art (see, e.g., Staendart et al., Nature 346:671, 1990 (human FKBP12); Kay, Biochem. J. 314:361, 1996). Homologous FKBP proteins in other mammalian species, in yeast, and in other organisms are also known in the art and may be used in the fusion proteins disclosed herein. An FKBP domain contemplated in particular embodiments will be capable of binding to rapamycin or a rapalog thereof and participating in a tripartite complex with an FRB-containing protein (as may be determined by any means, direct or indirect, for detecting such binding).

Illustrative examples of FKBP domains suitable for use in a DARIC contemplated in particular embodiments include, but are not limited to: a naturally occurring FKBP peptide sequence, preferably isolated from the human FKBP12 protein (GenBank Accession No. AAA58476.1) or a peptide sequence isolated therefrom, from another human FKBP, from a murine or other mammalian FKBP, or from some other animal, yeast or fungal FKBP; a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

Other illustrative examples of multimerization domain pairs suitable for use in a DARIC contemplated in particular embodiments include, but are not limited to include from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In yet other embodiments, an anti-bridging factor blocks the association of a signaling polypeptide and a binding polypeptide with the bridging factor. For example, cyclosporin or FK506 could be used as anti-bridging factors to titrate out rapamycin and, therefore, stop signaling since only one multimerization domain is bound. In certain embodiments, an anti-bridging factor (e.g., cyclosporine, FK506) is an immunosuppressive agent. For example, an immunosuppressive anti-bridging factor may be used to block or minimize the function of the DARIC components contemplated in particular embodiments and at the same time inhibit or block an unwanted or pathological inflammatory response in a clinical setting.

In one embodiment, the first multimerization domain comprises FRB T2098L, the second multimerization domain comprises FKBP12, and the bridging factor is rapalog AP21967.

In another embodiment, the first multimerization domain comprises FRB, the second multimerization domain comprises FKBP12, and the bridging factor is Rapamycin, temsirolimus or everolimus.

In particular embodiments, a signaling polypeptide a first transmembrane domain and a binding polypeptide comprises a second transmembrane domain or GPI anchor.

Illustrative examples of the first and second transmembrane domains are isolated from a polypeptide independently selected from the group consisting of: CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a signaling polypeptide comprises one or more intracellular co-stimulatory signaling domains and/or primary signaling domains.

Illustrative examples of primary signaling domains suitable for use in DARIC signaling components contemplated in particular embodiments include those derived from FcRγ, FCRβ, CD3γ, CD3δ, CD3ε, CD3ζ, CD22, CD79a, CD79b, and CD66d. In particular preferred embodiments, a DARIC signaling component comprises a CD3ζ primary signaling domain and one or more costimulatory signaling domains. The intracellular primary signaling and costimulatory signaling domains may be linked in any order in tandem to the carboxyl terminus of the transmembrane domain.

Illustrative examples of such costimulatory molecules suitable for use in DARIC signaling components contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a DARIC signaling component comprises one or more costimulatory signaling domains selected from the group consisting of CD28, CD137, and CD134, and a CD3ζ primary signaling domain.

In particular embodiments, a DARIC binding component comprises a binding domain. In one embodiment, the binding domain is an antibody or antigen binding fragment thereof.

The antibody or antigen binding fragment thereof comprises at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the DARIC binding component comprises an extracellular domain that binds an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, the DARIC binding component comprises an extracellular domain, e.g., antibody or antigen binding fragment thereof that binds an MHC-peptide complex, such as a class I MHC-peptide complex or class II MHC-peptide complex.

In particular embodiments, the DARIC components contemplated herein comprise a linker or spacer that connects two proteins, polypeptides, peptides, domains, regions, or motifs. In certain embodiments, a linker comprises about two to about 35 amino acids, or about four to about 20 amino acids or about eight to about 15 amino acids or about 15 to about 25 amino acids. In other embodiments, a spacer may have a particular structure, such as an antibody CH2CH3 domain, hinge domain or the like. In one embodiment, a spacer comprises the CH2 and CH3 domains of IgG1, IgG4, or IgD.

In particular embodiments, the DARIC components contemplated herein comprise one or more "hinge domains," which plays a role in positioning the domains to enable proper cell/cell contact, antigen binding and activation. A DARIC may comprise one or more hinge domains between the binding domain and the multimerization domain and/or the transmembrane domain (TM) or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region. In particular embodiment, the hinge is a CD8α hinge or a CD4 hinge.

In one embodiment, a DARIC comprises a signaling polypeptide comprises a first multimerization domain of FRB T2098L, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is rapalog AP21967.

In one embodiment, a DARIC comprises a signaling polypeptide comprises a first multimerization domain of FRB, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is Rapamycin, temsirolimus or everolimus.

4. Zetakines

In various embodiments, immune effector cells comprise chimeric cytokine receptor that redirect cytotoxicity toward tumor cells. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In particular embodiments, immune effector cells contemplated herein comprise one or more chains of a zetakine receptor and a CTBR signal convertor. In one embodiment, T cells are engineered by introducing a polynucleotide or vector encoding one or more chains of a zetakine receptor and a CTBR signal convertor separated by one or more polypeptide cleavage signals. In one embodiment, T cells are engineered by introducing a polynucleotide or vector encoding one or more chains of a zetakine receptor and a polynucleotide or vector encoding a CTBR signal convertor. In one embodiment, T cells are engineered to express one or more chains of a zetakine receptor are further engineered by introducing a polynucleotide or vector encoding a CTBR signal convertor.

In particular embodiments, the zetakine comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8α or CD4 hinge domain.

In particular embodiments, the transmembrane domain is selected from the group consisting of: the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In particular embodiments, the intracellular signaling domain is selected from the group consisting of: an ITAM containing primary signaling domain and/or a costimulatory domain.

In particular embodiments, the intracellular signaling domain is selected from the group consisting of: FcRγ, FcRβ, CD3γ, CD3δ, CD3ε, CD3, CD22, CD79a, CD79b, and CD66d.

In particular embodiments, the intracellular signaling domain is selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In one embodiment, a chimeric cytokine receptor comprises one or more costimulatory signaling domains selected from the group consisting of CD28, CD137, and CD134, and a CD3ζ primary signaling domain.

E. Polypeptides

Various polypeptides are contemplated herein, including, but not limited to, TGFβ signal convertor polypeptides, CTBRs, engineered TCRs, CARs, DARICs, zetakines, fusion proteins comprising the foregoing polypeptides and fragments thereof. In preferred embodiments, a polypeptide comprises an amino acid sequence set forth in any one of SEQ ID NOs: 1-71. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full length protein, or a fusion protein, and may include post-translational modifications of the polypeptide, for example, glycosylations, acetylations, phosphorylations and the like, as well as other modifications known in the art, both naturally occurring and non-naturally occurring.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long.

In particular embodiments, the polypeptides set forth herein may comprise one or more amino acids denoted as "X." "X" if present in an amino acid SEQ ID NO, refers to any one or more amino acids. In particular embodiments, SEQ ID NOs denoting a fusion protein comprise a sequence of continuous X residues that cumulatively represent any amino acid sequence.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acari Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene,* Fourth Edition, Benjamin/Cummings, Menlo Park, Calif, 1987) and the references cited therein. Guidance as to appropriate amino acid substitutions that do not affect biological activity of the protein of interest may be found in the model of Dayhoff et al., (1978) *Atlas of Protein Sequence and Structure (Natl. Biomed. Res. Found,* Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | | GCU | |
| Cysteine | C | Cys | UGC | | | UGU | | |
| Aspartic acid | D | Asp | GAC | | | GAU | | |
| Glutamic acid | E | Glu | GAA | | | GAG | | |
| Phenylalanine | F | Phe | UUC | | | UUU | | |
| Glycine | G | Gly | GGA | GGC | GGG | | GGU | |
| Histidine | H | His | CAC | | | CAU | | |
| Isoleucine | I | Iso | AUA | AUC | | AUU | | |
| Lysine | K | Lys | AAA | | | AAG | | |
| Leucine | L | Leu | UUA | UUG | CUA | CUC | CUG | CUU |
| Methionine | M | Met | | | AUG | | | |
| Asparagine | N | Asn | AAC | | | AAU | | |
| Proline | P | Pro | CCA | CCC | CCG | | CCU | |
| Glutamine | Q | Gln | CAA | | | CAG | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | | ACU | |
| Valine | V | Val | GUA | GUC | GUG | | GUU | |
| Tryptophan | W | Trp | | | UGG | | | |
| Tyrosine | Y | Tyr | UAC | | | UAU | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by an IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus Ma proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 47), for example, ENLYFQG (SEQ ID NO: 48) and ENLYFQS (SEQ ID NO: 49), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FIVIDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

Illustrative examples of 2A sites are provided in Table 2.

TABLE 2

| | |
|---|---|
| SEQ ID NO: 50 | GSGATNFSLLKQAGDVEENPGP |
| SEQ ID NO: 51 | ATNFSLLKQAGDVEENPGP |
| SEQ ID NO: 52 | LLKQAGDVEENPGP |
| SEQ ID NO: 53 | GSGEGRGSLLTCGDVEENPGP |
| SEQ ID NO: 54 | EGRGSLLTCGDVEENPGP |
| SEQ ID NO: 55 | LLTCGDVEENPGP |
| SEQ ID NO: 56 | GSGQCTNYALLKLAGDVESNPGP |
| SEQ ID NO: 57 | QCTNYALLKLAGDVESNPGP |
| SEQ ID NO: 58 | LLKLAGDVESNPGP |
| SEQ ID NO: 59 | GSGVKQTLNFDLLKLAGDVESNPGP |
| SEQ ID NO: 60 | VKQTLNFDLLKLAGDVESNPGP |
| SEQ ID NO: 61 | LLKLAGDVESNPGP |
| SEQ ID NO: 62 | LLNFDLLKLAGDVESNPGP |
| SEQ ID NO: 63 | TLNFDLLKLAGDVESNPGP |
| SEQ ID NO: 64 | LLKLAGDVESNPGP |
| SEQ ID NO: 65 | NFDLLKLAGDVESNPGP |

TABLE 2-continued

| | |
|---|---|
| SEQ ID NO: 66 | QLLNFDLLKLAGDVESNPGP |
| SEQ ID NO: 67 | APVKQTLNFDLLKLAGDVESNPGP |
| SEQ ID NO: 68 | VTELLYRMKRAETYCPRPLLAIHPTEARHKQKIVAPVKQT |
| SEQ ID NO: 69 | LNFDLLKLAGDVESNPGP |
| SEQ ID NO: 70 | LLAIHPTEARHKQKIVAPVKQTLNFDLLKLAGDVESNPGP |
| SEQ ID NO: 71 | EARHKQKIVAPVKQTLNFDLLKLAGDVESNPGP |

In preferred embodiments, a polypeptide comprises a CTBR signal convertor polypeptide.

F. Polynucleotides

In particular embodiments, polynucleotides encoding TGFβ signal convertor polypeptides, CTBRs, engineered TCRs, CARs, DARICs, zetakines, fusion proteins comprising the foregoing polypeptides and fragments thereof are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include, but are not limited to polynucleotides encoding SEQ ID NOs: 1-71.

In various illustrative embodiments, polynucleotides contemplated herein include, but are not limited to polynucleotides encoding TGFβ signal convertors, CTBR signal convertors, engineered antigen receptors, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

In various embodiments, a polynucleotide comprises an mRNA encoding a polypeptide contemplated herein. In certain embodiments, the mRNA comprises a cap, one or more nucleotides, and a poly(A) tail.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' CAT GAC T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In particular embodiments, the polynucleotides are codon optimized for expression and/or stability. Further, alleles of the genes comprising the polynucleotide sequences provided herein may also be used. Alleles are endogenous genes that are altered as a result of one or more mutations, such as deletions, additions and/or substitutions of nucleotides.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., Sleeping Beauty, PiggyBac.

Additional Illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4N5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/ enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter (Challita et al., *J Virol.* 69(2):748-55 (1995)).

In one embodiment, a vector comprises an MND promoter.

In one embodiment, a vector comprises an EF1a promoter comprising the first intron of the human EF1a gene.

In one embodiment, a vector comprises an EF1a promoter that lacks the first intron of the human EF1a gene.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

In a particular embodiment, it may be desirable to express a polynucleotide a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc. Inducer agents include, but are not limited to glucocorticoids, estrogens, mifepristone (RU486), metals, interferons, small molecules, cumate, tetracycline, doxycycline, and variants thereof.

Conditional expression can also be achieved by using a site specific DNA recombinase. According to certain embodiments the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, *Current Opinion in Biotechnology* 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), F4, F5 (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagaraj an et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. *J. Virol* 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO:72), where R is a purine (A or G) (Kozak, 1986. *Cell*. 44(2):283-92, and Kozak, 1987. *Nucleic Acids Res*. 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the immune effector cells, e.g., T cells, to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., *Cell* 11:223, 1977) which confers ganciclovir sensitivity; the cellular hypoxanthine phosphribosyltransferase (HPRT) gene, the cellular adenine phosphoribosyltransferase (APRT) gene, and bacterial cytosine deaminase, (Mullen et al., *Proc. Natl. Acad. Sci. USA*. 89:33 (1992)).

In some embodiments, genetically modified immune effector cells, such as T cells, comprise a polynucleotide further comprising a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides encoding one or more polypeptides, or fusion polypeptides may be introduced into immune effector cells, e.g., T cells, by both non-viral and viral methods. In particular embodiments, delivery of one or more polynucleotides may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising nuclease variants and/or donor repair templates are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated in particular embodiments include, but are not limited to adeno-associated virus (AAV), retrovirus, herpes simplex virus, adenovirus, and vaccinia virus vectors.

In various embodiments, one or more polynucleotides are introduced into an immune effector cell, e.g., T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides are introduced into an immune effector cell, e.g., T cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (T) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81R, D41A, K42A, H51A, Q53C, D55V, D64E, D64V, E69A, K71A, E85A, E87A, D116N, D116I, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell*, 101:173.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology*, Vol. 69, No. 4; pp. 2101-2109.

The term "export element" refers to a cis-acting posttranscriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. In particular embodiments, it is desirable to eliminate enough of the U3 sequence to greatly diminish or abolish altogether the transcriptional activity of the LTR, thereby greatly diminishing or abolishing the production of full-length vector RNA in transduced cells. In the case of HIV based lentivectors, it has been discovered that such vectors tolerate significant U3 deletions, including the removal of the LTR TATA box (e.g., deletions from −418 to −18), without significant reductions in vector titers.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat.

Nos. 6,013,516; and 5,994,136, many of which may be adapted to produce a viral vector or transfer plasmid contemplated herein.

In various embodiments, one or more polynucleotides are introduced into an immune effector cell, by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad Ela, Elb, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides are introduced into an immune effector cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

G. Genetically Modified Cells

In various embodiments, cells are modified to express TGFβ signal convertor polypeptides, CTBRs, engineered TCRs, CARs, DARICs, zetakines, and fusion proteins contemplated herein, for use in the treatment of cancer. Cells may be non-genetically modified to express the polypeptides contemplated herein, or in particular preferred embodiments, cells may be genetically modified to express the polypeptides contemplated herein. As used herein, the term "genetically engineered" or "genetically modified" refers to the addition of extra genetic material in the form of DNA or RNA into the total genetic material in a cell. The terms, "genetically modified cells," "modified cells," and "redirected cells," are used interchangeably in particular embodiments.

In particular embodiments, the CTBR signal convertor polypeptides contemplated herein are introduced and expressed in immune effector cells to improve the resistance of the cells to the immunosuppressive signals in the TME mediated by TGFβ. In particular embodiments, CTBR signal convertor polypeptides are introduced and expressed in immune effector cells that have been redirected to a target cell by virtue of co-expressing an engineered antigen receptor in the cell.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, in particular cytotoxic T cells (CTLs; CD8+ T cells), TILs, and helper T cells (HTLs; CD4+ T cells). In one embodiment, immune effector cells include natural killer (NK) cells. In one embodiment, immune effector cells include natural killer T (NKT) cells. Immune effector cells can be autologous/autogeneic ("self") or non-autologous ("non-self," e.g., allogeneic, syngeneic or xenogeneic).

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are autologous.

Illustrative immune effector cells suitable for introducing the CTBR signal convertor polypeptides contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), CD4+CD8+ T cell, CD4−CD8− T cell, or any other subset of T cells. Other illustrative populations of T cells suitable for use in particular embodiments include naïve T cells and memory T cells.

As would be understood by the skilled person, other cells may also be used as immune effector cells with CTBR signal convertor polypeptides contemplated herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in particular embodiments, immune effector cell includes progenitors of immune effectors cells such as hematopoietic stem cells (HSCs) contained within the $CD34^+$ population of cells derived from cord blood, bone marrow or mobilized peripheral blood which upon administration in a subject differentiate into mature immune effector cells, or which can be induced in vitro to differentiate into mature immune effector cells.

As used herein, immune effector cells genetically engineered to contain a specific chimeric receptor may be referred to as, "antigen specific redirected immune effector cells."

The term, "$CD34^+$ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The $CD34^+$ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells which express a TGFβ signal convertor polypeptide contemplated herein are provided in particular embodiments. In one embodiment, the method comprises transfecting or transducing immune effector cells isolated from an individual such that the immune effector cells express one or more TGFβ signal convertor polypeptides as contemplated herein. In one embodiment, the method comprises transfecting or transducing immune effector cells isolated from an individual such that the immune effector cells express one or more TGFβ signal convertor polypeptides and engineered antigen receptors contemplated herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified. In this regard, the immune effector cells may be cultured before and/or after being genetically modified.

In particular embodiments, prior to in vitro manipulation or genetic modification of the immune effector cells described herein, the source of cells is obtained from a subject. In particular embodiments, the modified immune effector cells comprise T cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In other embodiments, an isolated or purified population of T cells is used. In some embodiments, after isolation of PBMC, both cytotoxic and helper T lymphocytes can be sorted into naïve, memory, and effector T cell subpopulations either before or after activation, expansion, and/or genetic modification.

In one embodiment, an isolated or purified population of T cells expresses one or more of the markers including, but not limited to a $CD3^+$, $CD4^+$, $CD8^+$, or a combination thereof.

In certain embodiments, the T cells are isolated from an individual and first activated and stimulated to proliferate in vitro prior to being modified to express a TGFβ signal convertor polypeptide.

In order to achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or polynucleotides encoding the TGFβ signal convertor polypeptides. Optionally in combination with an engineered antigen receptor contemplated herein.

In one embodiment, T cells are activated at the same time that they are modified.

In various embodiments, a method of generating an immune effector cell comprises activating a population of cells comprising T cells and expanding the population of T cells. T cell activation can be accomplished by providing a primary stimulation signal through the T cell TCR/CD3 complex and by providing a secondary costimulation signal through an accessory molecule, e.g., CD28.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1.

In addition to the primary stimulation signal provided through the TCR/CD3 complex, induction of T cell responses requires a second, costimulatory signal. In particular embodiments, a CD28 binding agent can be used to provide a costimulatory signal. Illustrative examples of CD28 binding agents include but are not limited to: natural CD 28 ligands, e.g., a natural ligand for CD28 (e.g., a member of the B7 family of proteins, such as B7-1(CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, the molecule providing the primary stimulation signal, for example a molecule which provides stimulation through the TCR/CD3 complex and the costimulatory molecule are coupled to the same surface.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex and the costimulatory molecule are displayed on antigen presenting cells.

In one embodiment, the molecule providing the primary stimulation signal, for example a molecule which provides stimulation through the TCR/CD3 complex and the costimulatory molecule are provided on separate surfaces.

In a certain embodiment, one of the binding agents that provides stimulatory and costimulatory signals is soluble (provided in solution) and the other agent(s) is provided on one or more surfaces.

In a particular embodiment, the binding agents that provide stimulatory and costimulatory signals are both provided in a soluble form (provided in solution).

In various embodiments, the methods for making T cells contemplated herein comprise activating T cells with anti-CD3 and anti-CD28 antibodies.

In one embodiment, expanding T cells activated by the methods contemplated herein further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days. Several cycles of stimulation/activation/expansion may also be desired such that culture time of T cells can be 60 days or more.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

In particular embodiments, PBMCs or isolated T cells are contacted with a stimulatory agent and costimulatory agent, such as anti-CD3 and anti-CD28 antibodies, generally attached to a bead or other surface, in a culture medium with appropriate cytokines, such as IL-2, IL-7, and/or IL-15.

In other embodiments, artificial APC (aAPC) made by engineering K562, U937, 721.221, T2, and C1R cells to direct the stable expression and secretion, of a variety of costimulatory molecules and cytokines. In a particular embodiment K32 or U32 aAPCs are used to direct the display of one or more antibody-based stimulatory molecules on the AAPC cell surface. Populations of T cells can be expanded by aAPCs expressing a variety of costimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

In a particular embodiment, polynucleotide encoding a TGFβ signal convertor and an engineered antigen receptor are introduced into the population of T cells. In a particular embodiment, polynucleotide encoding a TGFβ signal convertor is introduced into a population of T cells that express an engineered antigen receptor. The polynucleotides may be introduced into the T cells by microinjection, transfection, lipofection, heat-shock, electroporation, transduction, gene gun, microinjection, DEAE-dextran-mediated transfer, and the like.

In a preferred embodiment, polynucleotides are introduced into a T cell by viral transduction.

Illustrative examples of viral vector systems suitable for introducing a polynucleotide into an immune effector cell or $CD34^+$ cell include, but are not limited to adeno-associated virus (AAV), retrovirus, herpes simplex virus, adenovirus, vaccinia virus vectors for gene transfer.

In one embodiment, polynucleotides are introduced into a T cell by AAV transduction.

In one embodiment, polynucleotides are introduced into a T cell by retroviral transduction.

In one embodiment, polynucleotides are introduced into a T cell by lentiviral transduction.

In one embodiment, polynucleotides are introduced into a T cell by adenovirus transduction.

In one embodiment, polynucleotides are introduced into a T cell by herpes simplex virus transduction.

In one embodiment, polynucleotides are introduced into a T cell by vaccinia virus transduction.

H. Compositions and Formulations

The compositions contemplated herein may comprise one or more polypeptides, polynucleotides, vectors comprising same, genetically modified immune effector cells, etc. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the polypeptides, polynucleotides, vectors comprising same, or genetically modified immune effector cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the polypeptides, polynucleotides, vectors comprising same, or genetically modified immune effector cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the modified T cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of modifed T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In a preferred embodiment, the compositions comprising modifed T cells are formulated in PlasmaLyte.

In various embodiments, compositions comprising modified T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. $22^{nd}$ Edition. Edited by Loyd V. Allen Jr. Philadelphia, PA: Pharmaceutical Press; 2012, which is incorporated by reference herein, in its entirety.

In particular embodiments, compositions comprise an amount of immune effector cells, including CAR T cells, that express a CTBR signal convertor contemplated herein. As used herein, the term "amount" refers to "an amount effective" or "an effective amount" of cells comprising a CTBR signal convertor contemplated herein, etc., to achieve a beneficial or desired prophylactic or therapeutic result, including clinical results.

A "prophylactically effective amount" refers to an amount of cells comprising a CTBR signal convertor contemplated herein, etc., effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" refers to an amount of cells comprising a CTBR signal convertor contemplated herein that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the immune effector cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some embodiments, particularly since all the infused cells will be redirected to a particular target antigen, lower numbers of cells, in the range of $10^6$/kilogram ($10^6$-$10^{11}$ per patient) may be administered. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

Generally, compositions comprising the cells activated and expanded as described herein may be utilized in the treatment and prevention of diseases that arise in individuals who are immunocompromised. In particular, compositions contemplated herein are used in the treatment of cancer. In particular embodiments, the immune effector cells may be administered either alone, or as a pharmaceutical compositions in combination with carriers, diluents, excipients, and/or with other components such as IL-2 or other cytokines or cell populations.

In particular embodiments, pharmaceutical compositions comprise an amount of genetically modified T cells, in combination with one or more pharmaceutically or physiologically acceptable carriers, diluents or excipients.

In a particular embodiment, compositions comprise an effective amount of immune effector cells comprising a CTBR signal convertor contemplated herein, alone or in combination with one or more therapeutic agents, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising immune effector cells comprising a CTBR signal convertor contemplated herein may be administered in conjunction with any number of chemotherapeutic agents. Illustrative examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising immune effector cells comprising a CTBR signal convertor contemplated herein is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Other exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

Illustrative examples of therapeutic antibodies suitable for combination with the modified T cells comprising a CTBR signal convertor contemplated herein, include but are not limited to, bavituximab, bevacizumab (avastin), bivatuzumab, blinatumomab, conatumumab, daratumumab, duligotumab, dacetuzumab, dalotuzumab, elotuzumab (HuLuc63), gemtuzumab, ibritumomab, indatuximab, inotuzumab, lorvotuzumab, lucatumumab, milatuzumab, moxetumomab, ocaratuzumab, ofatumumab, rituximab, siltuximab, teprotumumab, and ublituximab.

In certain embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

I. Therapeutic Methods

The immune effector cells, including CAR T cells, comprising a CTBR contemplated herein provide improved methods of adoptive immunotherapy for use in the prevention, treatment, and amelioration cancers, or for preventing, treating, or ameliorating at least one symptom associated with a cancer.

The immune effector cells that comprise an engineered receptor and a CTBR contemplated herein provide improved drug products for use in the prevention, treatment, or amelioration of at least one symptom of a cancer, GVHD, an infectious disease, an autoimmune disease, an inflammatory disease, or an immunodeficiency. As used herein, the term "drug product" refers to modified cells produced using the compositions and methods contemplated herein. In particular embodiments, the drug product comprises genetically modified immune effector cells, T cells comprising an engineered receptor, or CAR T cells further modified to express a CTBR signal convertor. Moreover, the modified T cells contemplated in particular embodiments provide safer and more efficacious adoptive cell therapies because they are resistant to T cell exhaustion and display increased durability and persistence in the tumor microenvironment that can lead to sustained therapy.

In particular embodiments, an effective amount of modified immune effector cells or T cells comprising an engineered receptor and a CTBR signal convertor are administered to a subject to prevent, treat, or ameliorate at least one symptom of a cancer, GVHD, an infectious disease, an autoimmune disease, an inflammatory disease, or an immunodeficiency.

In particular embodiments, a method of preventing, treating, or ameliorating at least one symptom of a cancer comprises administering the subject an effective amount of modified immune effector cells or T cells comprising a CTBR signal convertor and an engineered TCR, CAR, or Daric, or other therapeutic transgene to redirect the cells to a tumor or cancer. The genetically modified cells are a more durable and persistent drug product because the cells are more resistant to immunosuppressive signals from the tumor microenvironment by virtue of converting an immunosuppressive TGFβ signal to an immunostimulatory signal.

In particular embodiments, the modified immune effector cells contemplated herein are used in the treatment of solid tumors or cancers.

In particular embodiments, the modified immune effector cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the modified immune effector cells contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, the modified immune effector cells contemplated herein are used in the treatment of various cancers including but not limited to pancreatic, bladder, and lung.

In particular embodiments, the modified immune effector cells contemplated herein are used in the treatment of liquid cancers or hematological cancers.

In particular embodiments, the modified immune effector cells contemplated herein are used in the treatment of B-cell malignancies, including but not limited to: leukemias, lymphomas, and multiple myeloma.

In particular embodiments, the modified immune effector cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CIVIL), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

Preferred cells for use in the methods contemplated herein include autologous/autogeneic ("self") cells, preferably hematopoietic cells, more preferably T cells, and more preferably immune effector cells.

In particular embodiments, methods comprising administering a therapeutically effective amount of modified immune effector cells contemplated herein or a composition comprising the same, to a patient in need thereof, alone or in combination with one or more therapeutic agents, are provided. In certain embodiments, the cells are used in the treatment of patients at risk for developing a cancer, GVHD, an infectious disease, an autoimmune disease, an inflammatory disease, or an immunodeficiency. Thus, particular embodiments comprise the treatment or prevention or amelioration of at least one symptom of a cancer, an infectious disease, an autoimmune disease, an inflammatory disease, or an immunodeficiency comprising administering to a subject in need thereof, a therapeutically effective amount of the genome edited cells contemplated herein.

In one embodiment, a method of treating a cancer, GVHD, an infectious disease, an autoimmune disease, an inflammatory disease, or an immunodeficiency in a subject in need thereof comprises administering an effective amount, e.g., therapeutically effective amount of a composition comprising modified immune effector cells contemplated herein. The quantity and frequency of administration will be determined by such factors as the condition of the patient, and the type and severity of the patient's disease, although appropriate dosages may be determined by clinical trials.

In one illustrative embodiment, the effective amount of modified immune effector cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of modified immune effector cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of modified immune effector cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

In one embodiment, a method of treating a subject diagnosed with a cancer, comprises removing immune effector cells from the subject, modifying the immune effector cells by introducing one or more vectors encoding an engineered antigen receptor and a TGFβ signal convertor and producing a population of modified immune effector cells, and administering the population of modified immune effector cells to the same subject. In a preferred embodiment, the immune effector cells comprise T cells.

The methods for administering the cell compositions contemplated in particular embodiments include any method which is effective to result in reintroduction of ex vivo modified immune effector cells or on reintroduction of the modified progenitors of immune effector cells that on introduction into a subject differentiate into mature immune effector cells. One method comprises modifying peripheral blood T cells ex vivo by introducing one or more vectors encoding an engineered antigen receptor and a TGFβ signal convertor and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

T Cells Expressing a TGFβ IL-12R Signal Convertor (Ctbr12) and a Chimeric Antigen Receptor (Car)

Illustrative TGFβ IL-12R based signal convertor constructs were designed as shown in FIG. 1.

Optimal IL-12 receptor signaling is initiated by dimerization of the intracellular domains of the IL-12Rβ1 and IL-12Rβ2 subunits following IL-12 ligation. To convert a TGFβ signal to induce IL-12 receptor signaling after exposure to TGFβ, the intracellular domains of TGFβ receptor 1 (TGFβR1) and TGFβ receptor 2 (TGFβR2) were replaced with the IL-12Rβ1 and IL-12Rβ2 signaling domains, respectively. The IL-12Rβ1 and IL-12Rβ2 transmembrane and signaling domains were cloned into a lentiviral vector encoding a CAR and separated by 2A self-cleaving polypeptide sequences (CAR.CTBR12).

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and a TGFβR2 subunit; or (iv) an anti-ROR1 CAR and CTBR12 (anti-ROR1.CTBR12). After 10 days of culture in IL-2 containing growth media, cell surface expression of the anti-ROR1 CAR and TGFβR2 was determined by flow cytometry. A recombinant human ROR1 protein conjugated to R-phycoerythrin (R-PE) was used to specifically stain the anti-ROR1 CAR expressing T cells. A commercially available antibody to TGFBR2 was used to detect CTBR12. Representative expression data is shown in FIG. 2.

Figure 2:
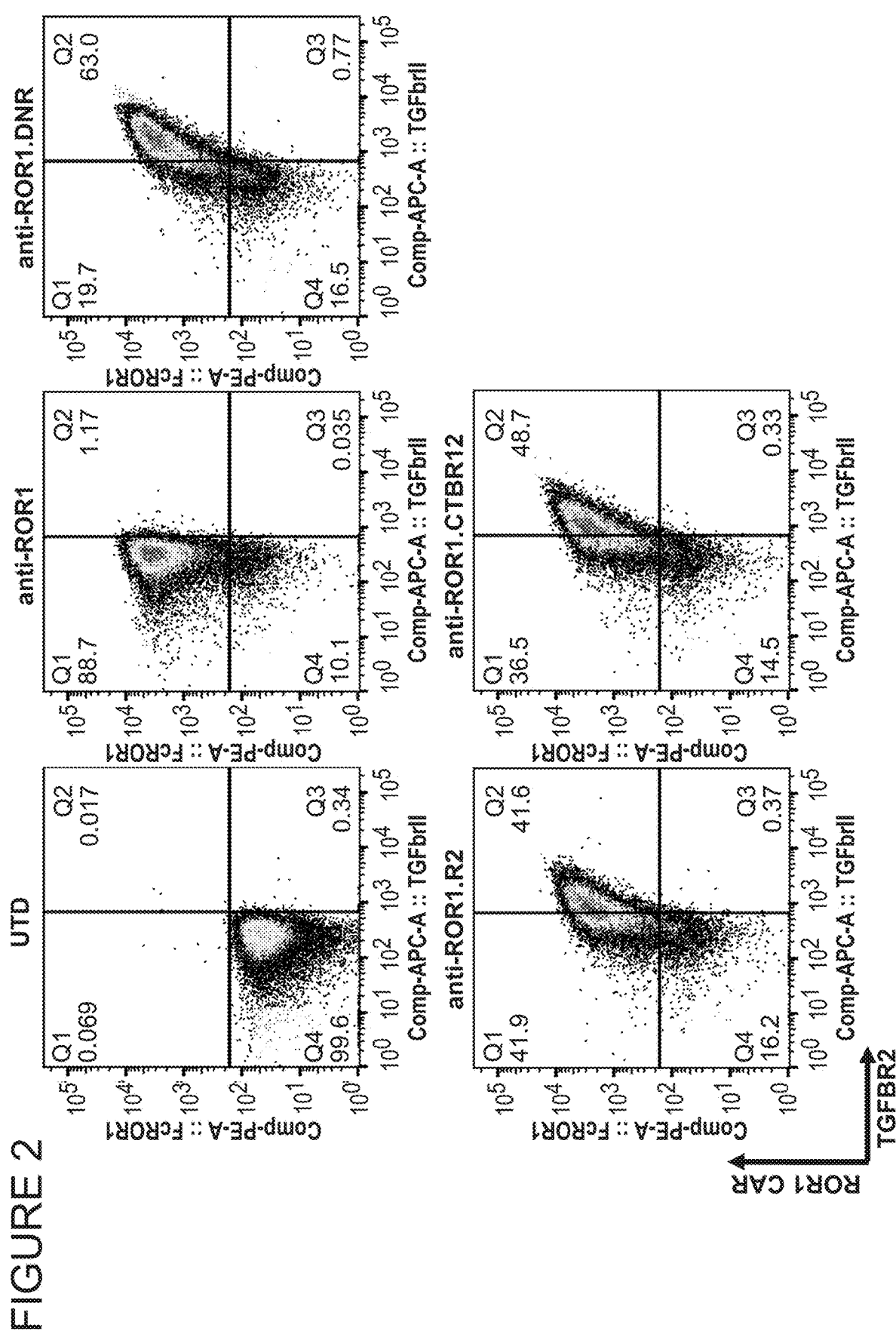
FIG. 2 shows CAR and TGFβR2 subunit expression in primary human T cells transduced with an anti-ROR1 CAR alone and in combination with the TGFβ DNR, TGFβ R2 subunit, and the CTBR12 signal convertor.

Fifty percent of T cells transduced with the lentiviral vector encoding the anti-ROR1 CAR and CTBR12 co-expressed the anti-ROR1 CAR and CTBR12 (rightmost panel of FIG. 2). In contrast, neither the anti-ROR1 CAR nor CTBR12 was detected in untransduced T cells, indicating that the antibody to TGFBR2 did not detect endogenous TGFBR2.

Example 2

Immunosuppressive TGFβ Signaling Inhibited by CTBR12

TGFβ1 ligation to a tetrameric complex containing 2 units of TGFβR1 and 2 units of TGFβR2 induces SMAD2 and SMAD3 phosphorylation to propagate an immunosuppressive signal to the cell nucleus. Overexpression of a truncated TGFβR2 (dominant negative TGFβ receptor—DNR) renders T cells insensitive to TGFβ as shown by loss of SMAD2/3 phosphorylation in response to TGFβ treatment. Thus, phospho-SMAD2/3 expression was used to interrogate TGFβ signaling pathway activation.

Figure 3:
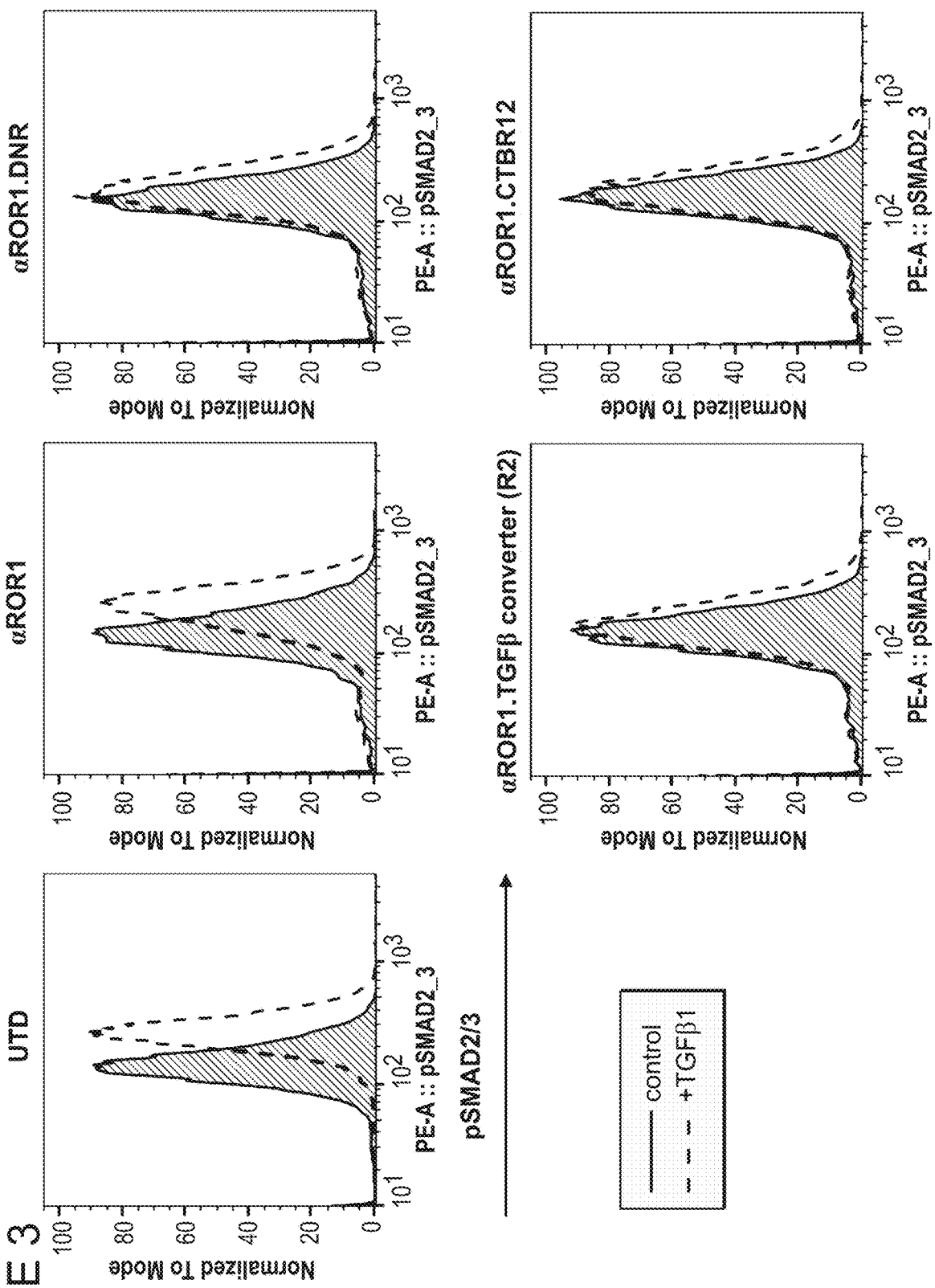
FIG. 3 shows phospho-SMAD2/3 expression in primary human T cells transduced with an anti-ROR1 CAR alone and in combination with the TGFβ DNR, TGFβ R2 subunit, and the CTBR12 signal convertor and treated with TGFβ1 compared to untreated cells.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and a TGFβR2 subunit; or (iv) an anti-ROR1 CAR and CTBR12 (anti-ROR1.CTBR12). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing either CTBR12 or DNR were completely protected from phosphorylation of SMAD2/3 (FIG. 3). These data demonstrated that expression of CTBR12 rendered anti-ROR1 CART cells insensitive to TGFβ immunosuppressive signaling.

Example 3

CTBR12 Transduces IL-12R Signaling Upon Exposure to TGFβ1

The cellular response to IL-12 is initiated by receptor dimerization and phosphorylation of STAT4 and STAT5. Thus, phospho-STAT4 and phospho-STAT5 expression was used to assess IL-12 receptor signaling pathway activation.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and a TGFβR2 subunit; or (iv) an anti-ROR1 CAR and CTBR12 (anti-ROR1.CTBR12). After 10 days of culture in IL-2 containing growth media, cultures were treated with 50 ng/mL of recombinant human IL-12 or with 10 ng/mL of recombinant human TGFβ1 for 20 minutes.

Figure 4:
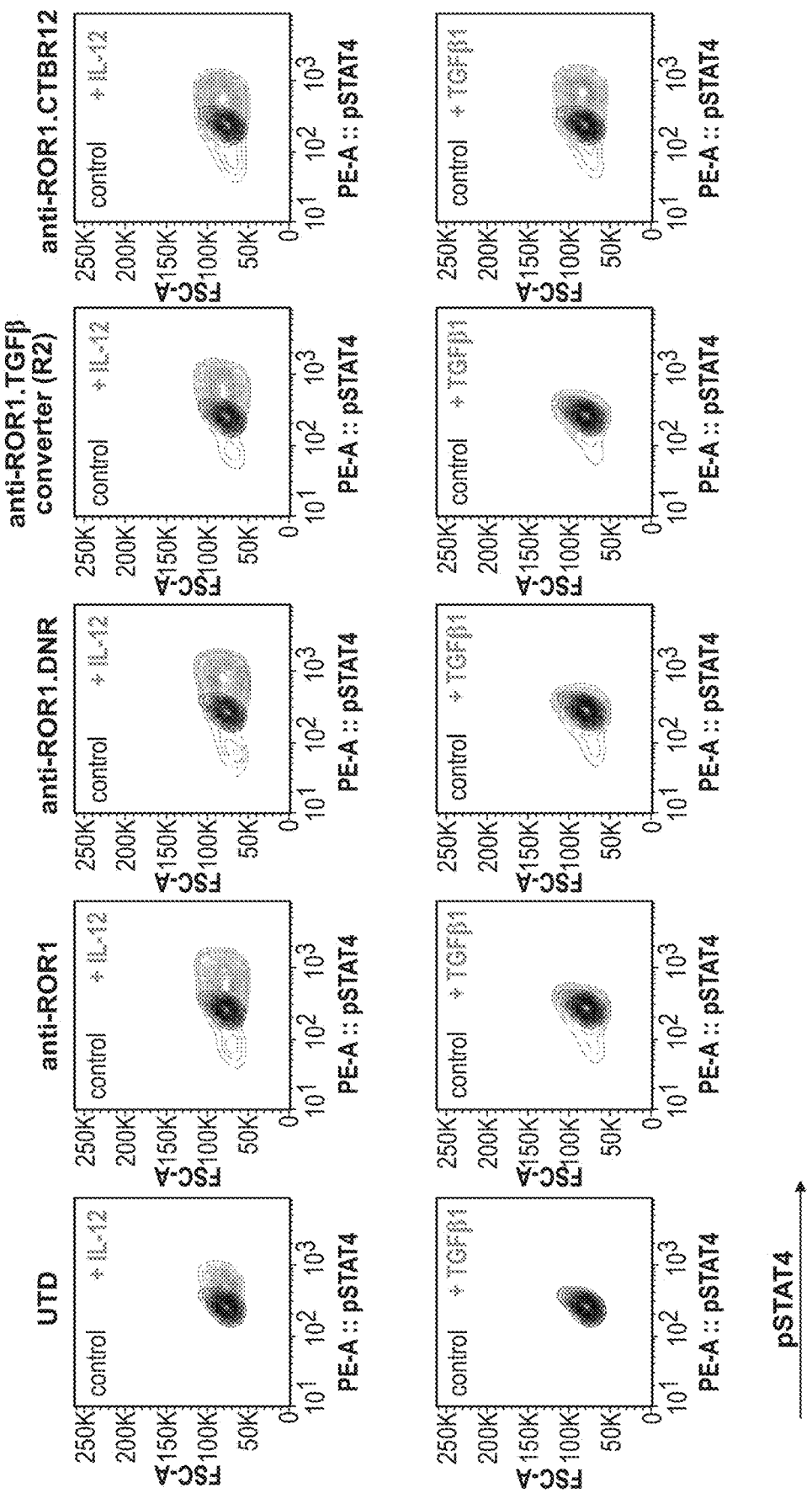
FIG. 4 shows phospho-STAT4 expression in primary human T cells transduced with an anti-ROR1 CAR alone and in combination with the TGFβ DNR, TGFβ R2 subunit, and the CTBR12 signal convertor and treated with either IL-12 (top row) or TGFβ1 (bottom row).

T cells expressing anti-ROR1 CARs cells exhibited increased levels of phosphorylated STAT4 (FIG. 4, top row, compare rightmost 4 panels to untransduced control (UTD)). Only CAR T cells expressing CTBR12 showed detectable levels of phospho-STAT4 expression when treated with recombinant human TGFβ1 (FIG. 4, bottom row, compare rightmost panel to other panels). In contrast, CAR T cells expressing only the TGFβR2 portion of the signal converter did not phosphorylate STAT4 in response to TGFβ treatment (FIG. 4, bottom row, fourth panel from the right).

Figure 5:
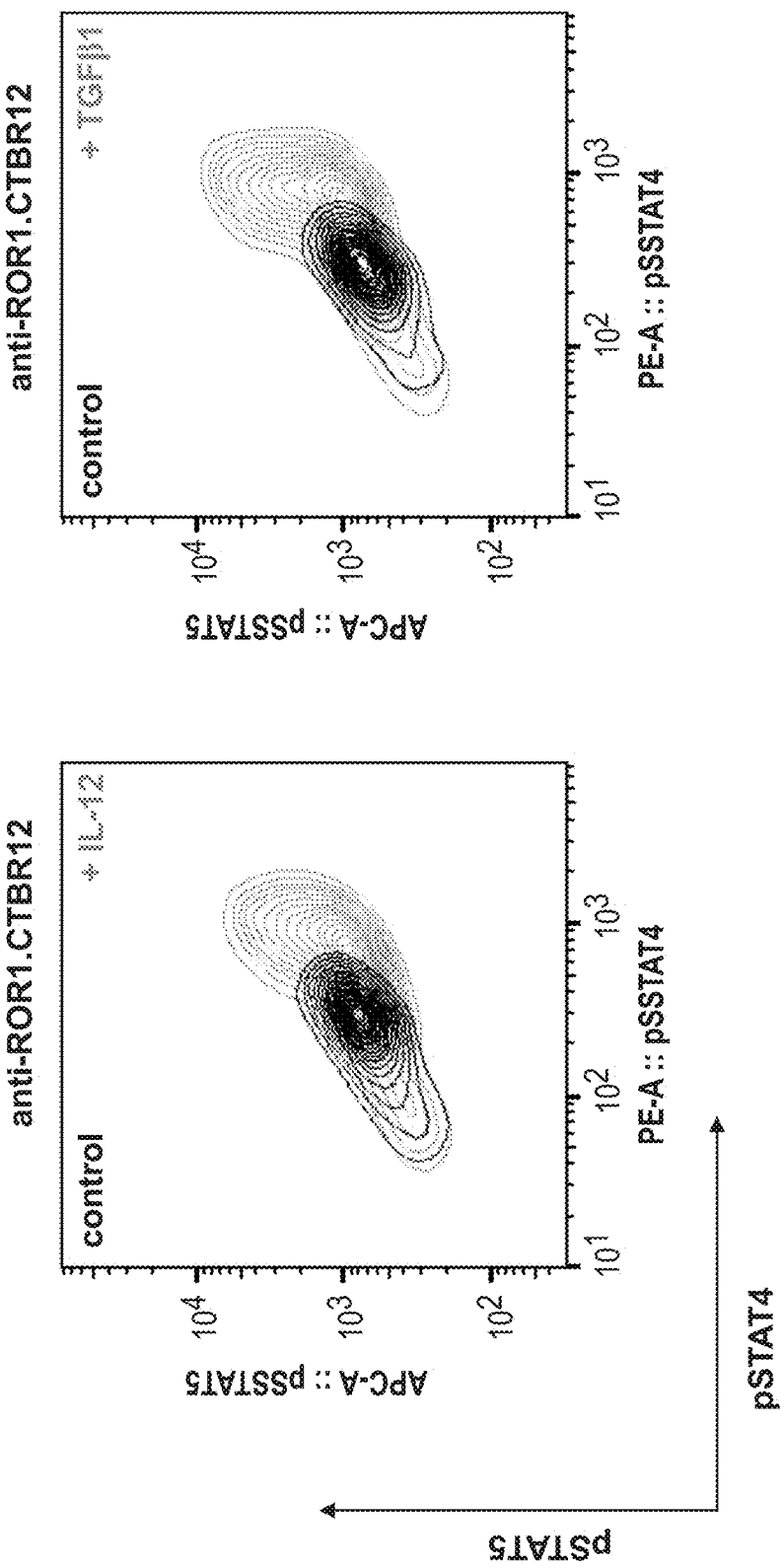
FIG. 5 shows phospho-STAT4 and phospho-STAT5 expression in primary human T cells transduced with an anti-ROR1 CAR and the CTBR12 signal convertor and treated with either IL-12 (left panel) or TGFβ1 (right panel).

CAR T cells expressing CTBR12 also exhibited detectable levels of phospho-STAT5 when treated with either IL-12 or TGFβ1, confirming that the converted TGFβ signal induces endogenous IL-12 receptor signaling (FIG. 5).

Figure 6:
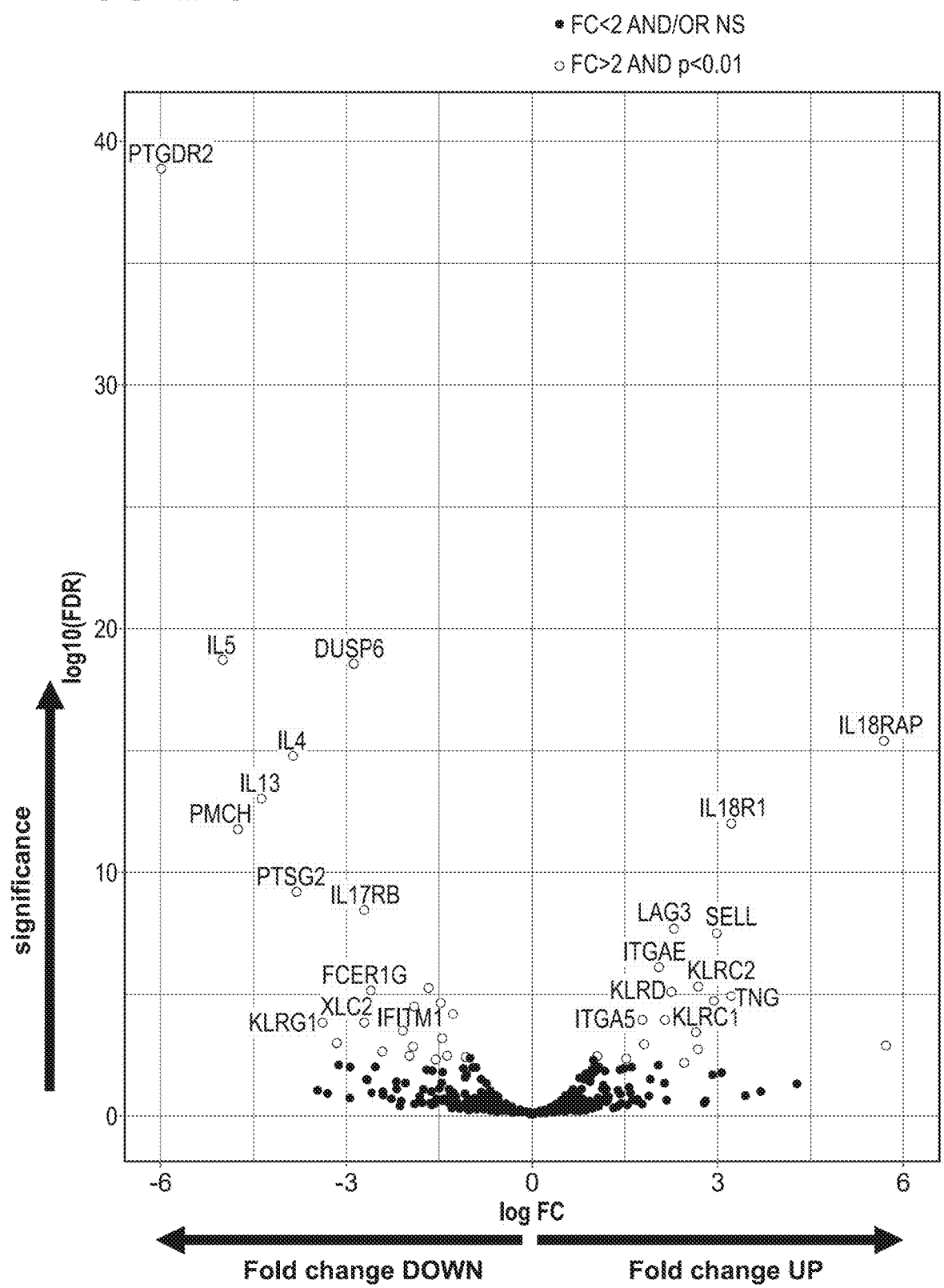
FIG. 6 shows gene expression analysis from primary human T cells transduced with anti-ROR1 CAR in combination with the CTBR12 signal convertor serially re-stimulated with ROR1 expressing target cells for 21 days in the presence or absence of TGFβ1.
Figure 6:
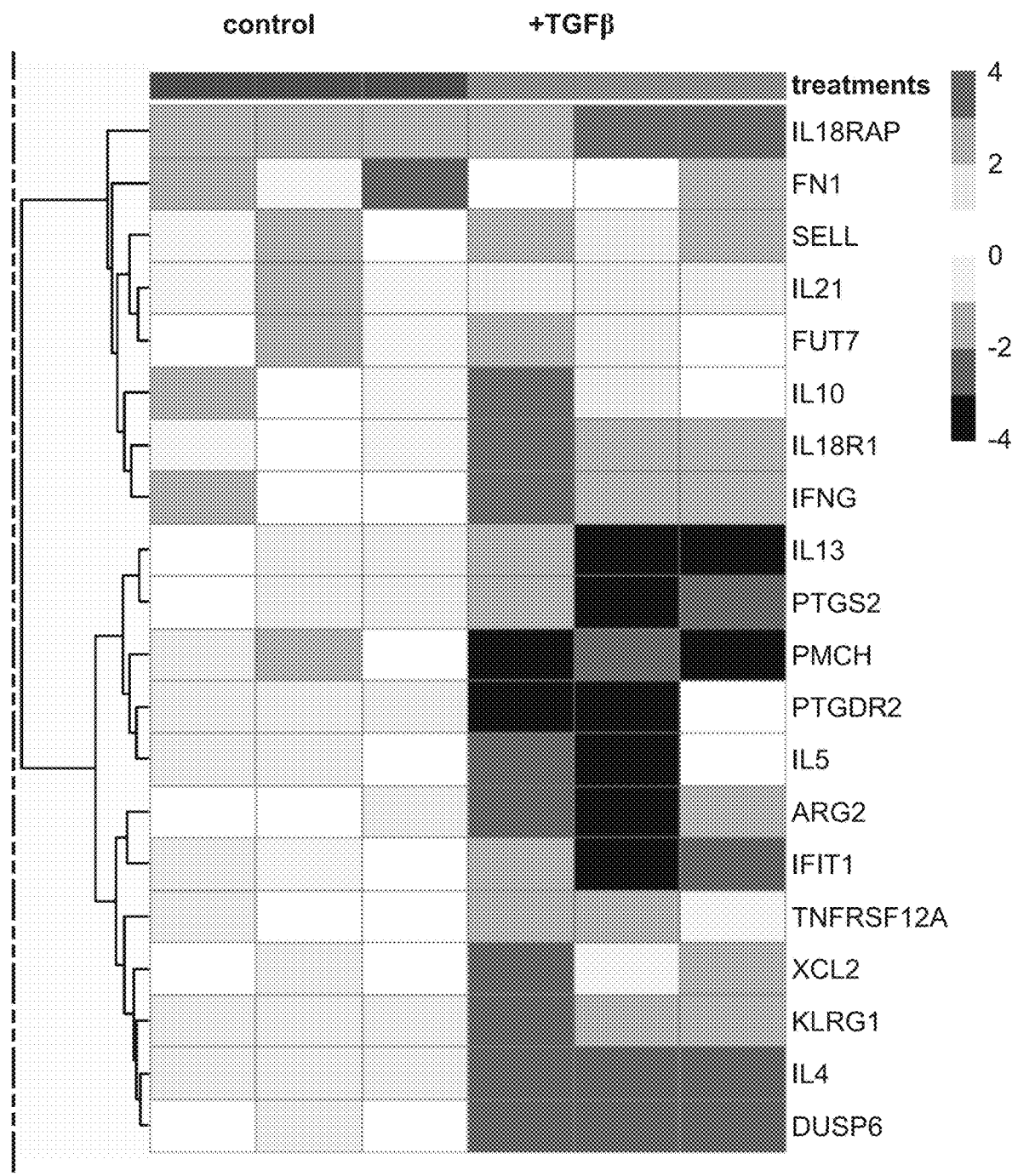

The gene expression of CART cells expressing the anti-ROR1.CTBR12 was measured in an antigen-driven serial expansion assay in the presence or absence of TGFβ1. Briefly, GFP-labeled K562 target cells that express human ROR1 antigen were used to serially expand the CART cells in the presence or absence of recombinant human TGFβ1. CAR T cells were stimulated with target cells at a 1:1 ratio once every seven days in the presence or absence of 5 ng/mL recombinant human TGFβ1. T cells were harvested and mRNA for gene expression analysis was isolated on day 21 following the initial stimulation. Gene expression analysis was performed using the Nanostring immune profiling panel. Significant gene expression changes driven by TGFβ1 treatment were identified (FIG. 6, left panel) in the anti-ROR1.CTBR12 expressing cells, including upregulation of the known IL-12R-regulated transcripts IFNG, SELL, IL18RAP, IL18R1, and IL21R (FIG. 6, right panel).

Example 4

CAR T Cells Expressing CTBR12 Secrete Increased IFNγ Upon Exposure to Antigen and TGFβ1

IL-12 receptor signaling in human T cells drives TH1 differentiation and increases effector function. IL-12 receptor signaling can cooperate with TCR signals to increase the release of IFNγ in response to antigen stimulation.

The R2/R1 signal converter amplified IFNγ production when T cells were stimulated through either a TCR or CAR in the presence of recombinant human TGFβ1. Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); or (iii) an anti-ROR1 CAR and CTBR12 (anti-ROR1.CTBR12). After 10 days of culture in IL-2 containing growth media, the cells were plated on either plate-bound anti-CD3 antibody (1 µg/mL) or recombinant human ROR1 protein (100 ng/mL) in the presence or absence of 5 ng/mL recombinant human TGFβ1. Forty eight hours post-plating, supernatants were collected and analyzed via Luminex for soluble cytokine content.

Figure 7:
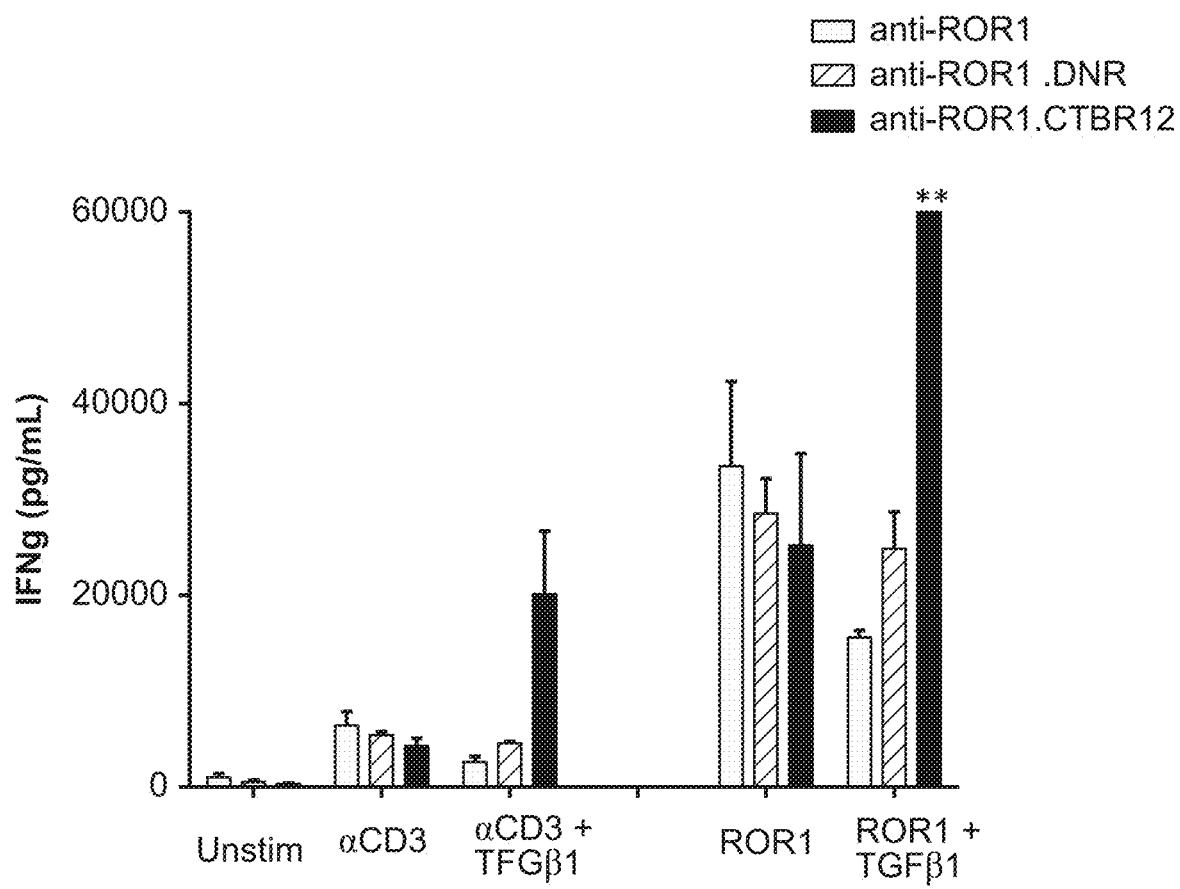
FIG. 7 shows IFNγ secretion from primary human T cells transduced with an anti-ROR1 CAR alone and in combination with the TGFβ DNR or the CTBR12 signal convertor and cultured in the presence or absence of TGFβ1 on plates coated with CD3 or ROR1.

CTBR12 expressing cells produced significantly greater amounts of IFNγ than the other cell types when stimulated through either TCR or CAR in the presence of recombinant human TGFβ1 (FIG. 7).

Example 5

CAR T Cells Expressing CTBR12 are Resistant to TGFβ1 Immunosuppressive Signals TGFβ signaling decreases T cell expansion in response to antigen stimulation. In contrast, IL-12 signaling increases T cell proliferation and reduces T cell hypofunction resulting from chronic antigen exposure.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); or (iii) an anti-ROR1 CAR and CTBR12 (anti-ROR1.CTBR12). After 10 days of culture in IL-2 containing growth media, the cells were subject to an in vitro serial re-stimulation assay.

Figure 8:
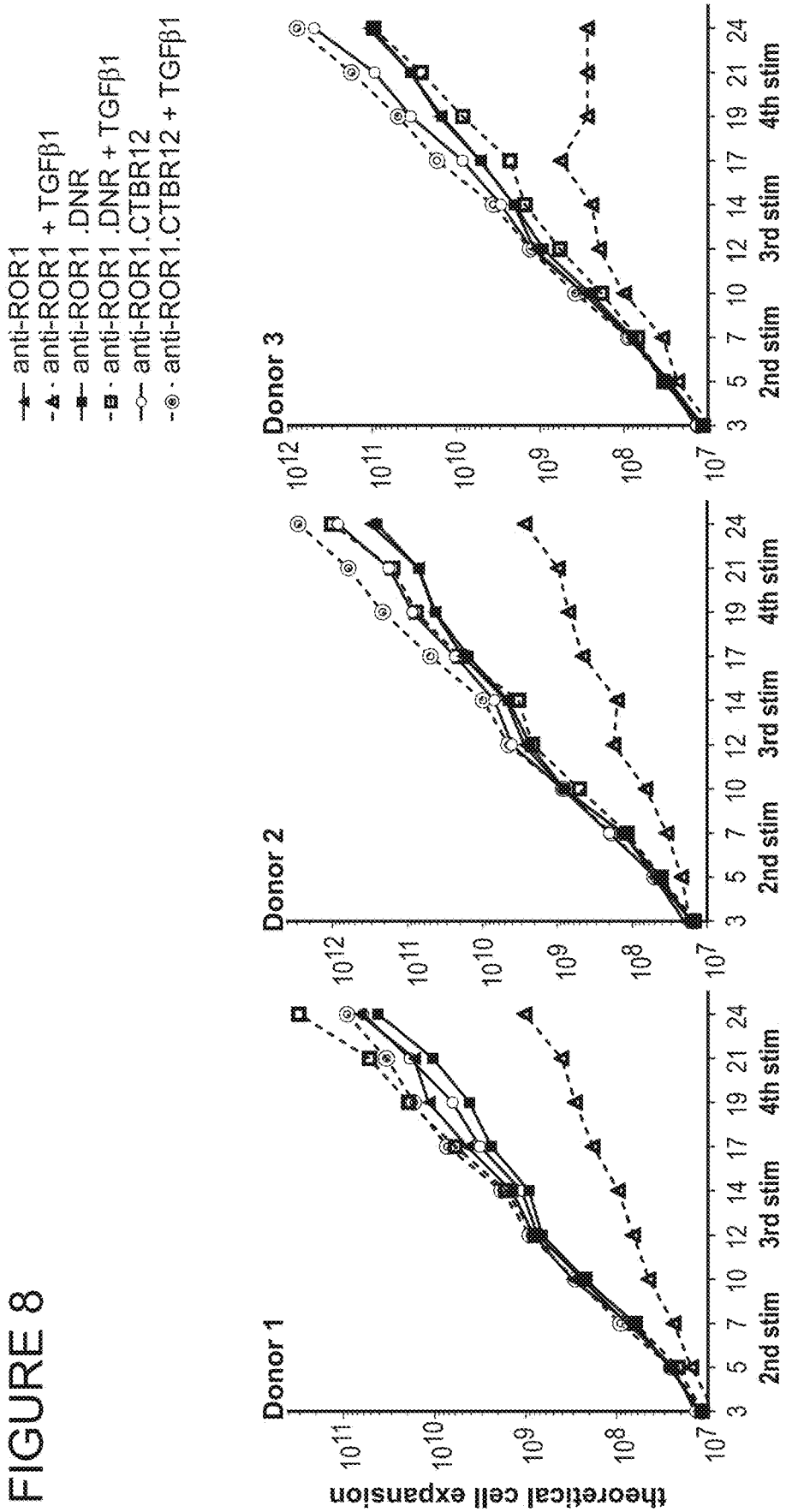
FIG. 8 shows the growth curves for primary human T cells transduced with an anti-ROR1 CAR alone and in combination with the TGFβ DNR or the CTBR12 signal convertor serially re-stimulated with ROR1 expressing target cells in the presence or absence of TGFβ1.

Briefly, GFP-labeled K562 target cells that express human ROR1 antigen were used to serially expand the CAR T cells in the presence or absence of recombinant human TGFβ1. CART cells were stimulated with target cells at a 1:1 ratio once every seven days in the presence or absence of 5 ng/mL recombinant human TGFβ1. Control anti-ROR1 CAR-T cells displayed minimal expansion in the presence of 5 ng/mL recombinant human TGFβ1 over the course of the assay. In contrast, anti-ROR1 CAR T cells co-expressing either the TGFβ DNR or CTBR12 were significantly protected from immunosuppressive TGFβ1 mediated signaling. FIG. 8. These results correlated with both the DNR's and CTBR12's ability to block SMAD phosphorylation (FIG. 8).

Example 6

T Cells Expressing a TGFβ-IL-7R Signal Convertor R2/R1 (CTBR7) and a Chimeric Antigen Receptor (CAR)

Illustrative TGFβ IL-7R based signal convertor (CTBR7) constructs were designed as shown in FIG. 1.

Optimal IL-7 receptor signaling is initiated by dimerization of the intracellular domains of the IL-7Rα and the common gamma chain (γc; IL-2Rγ) following IL-7 ligation. To convert a TGFβ signal to induce IL-7 receptor signaling after exposure to TGFβ, the intracellular domains of TGFβ receptor 1 (TGFβR1) and TGFβ receptor 2 (TGFβR2) were replaced with the IL-2Rγ and IL-7Rα signaling domains, respectively to produce an IL-7 signaling chimeric TGFβ receptor (CTBR7). The IL-2Rγ and IL-7Rα transmembrane and signaling domains were cloned into a lentiviral vector encoding a CAR and separated by 2A self-cleaving polypeptide sequences (CAR.CTBR7).

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and CTBR7 (anti-ROR1.CTBR7). After 10 days of culture in IL-2 containing growth media, cell surface expression of the anti-ROR1 CAR and TGFβR2 were determined by flow cytometry. A recombinant human ROR1 protein conjugated to R-phycoerythrin (R-PE) was used to specifically stain the anti-ROR1 CAR expressing T cells. A commercially available antibody to TGFBR2 was used to detect CTBR7. Representative expression data is shown in FIG. 9.

Figure 9:
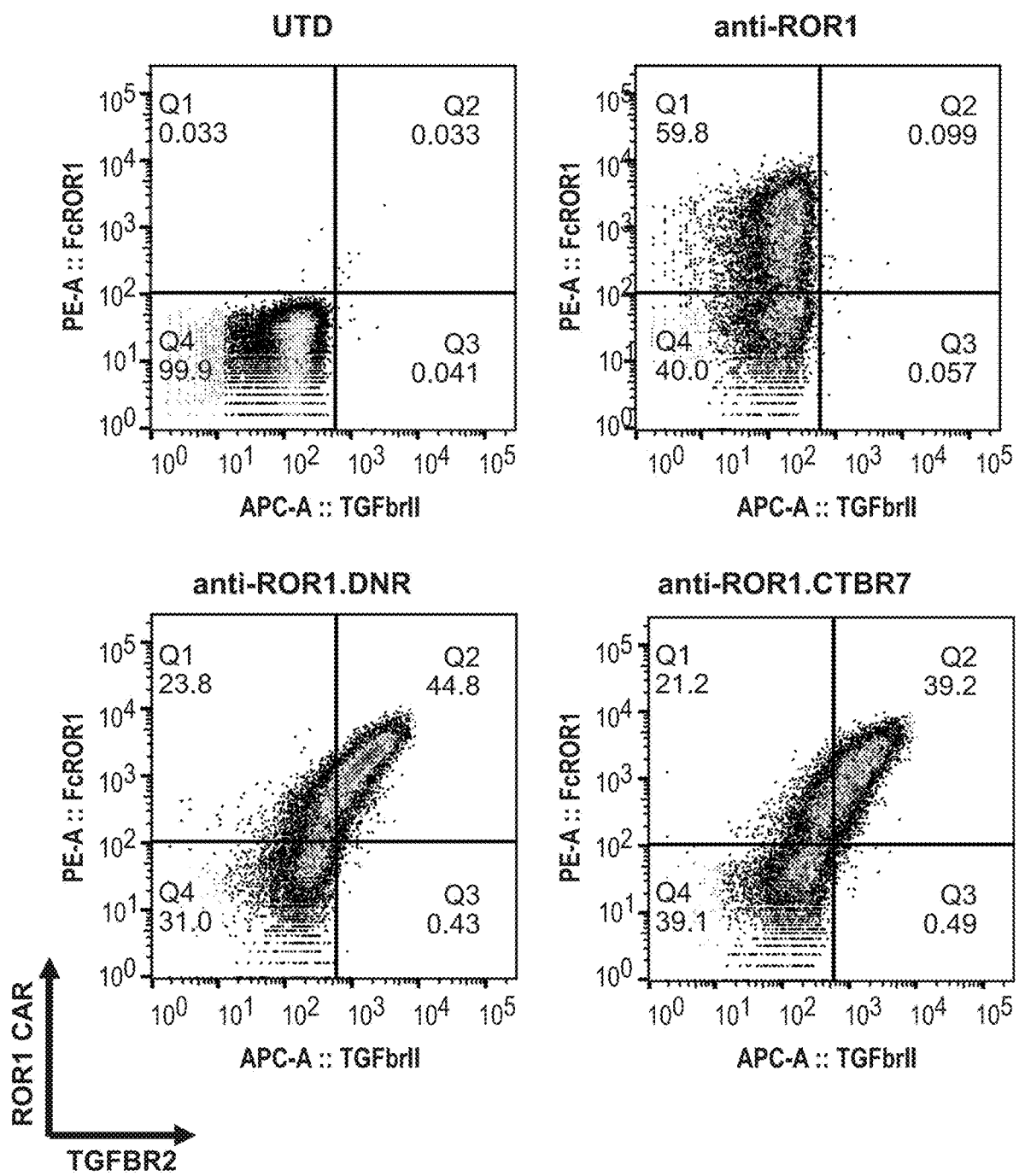
FIG. 9 shows CAR and TGFβR2 subunit expression in primary human T cells transduced with an anti-ROR1 CAR alone and in combination with the TGFβ DNR, and the CTBR7 signal convertor.

Forty percent of T cells transduced with the lentiviral vector encoding the anti-ROR1 CAR and CTBR7 co-expressed the anti-ROR1 CAR and CTBR7 (rightmost panel of FIG. 9). In contrast, neither the anti-ROR1 CAR nor CTBR7 was detected in untransduced T cells, indicating that the antibody to TGFBR2 did not detect endogenous TGFBR2.

Example 7

Immunosuppressive TGFβ Signaling Inhibited by CTBR7

TGFβ1 ligation to a tetrameric complex containing 2 units of TGFβR1 and 2 units of TGFβR2 induces SMAD2 and SMAD3 phosphorylation to propagate an immunosuppressive signal to the cell nucleus. Overexpression of a truncated TGFβR2 (dominant negative TGFβ receptor—DNR) renders T cells insensitive to TGFβ as shown by loss of SMAD2/3 phosphorylation in response to TGFβ treatment. Thus, phospho-SMAD2/3 expression was used to interrogate TGFβ signaling pathway activation.

Figure 10:
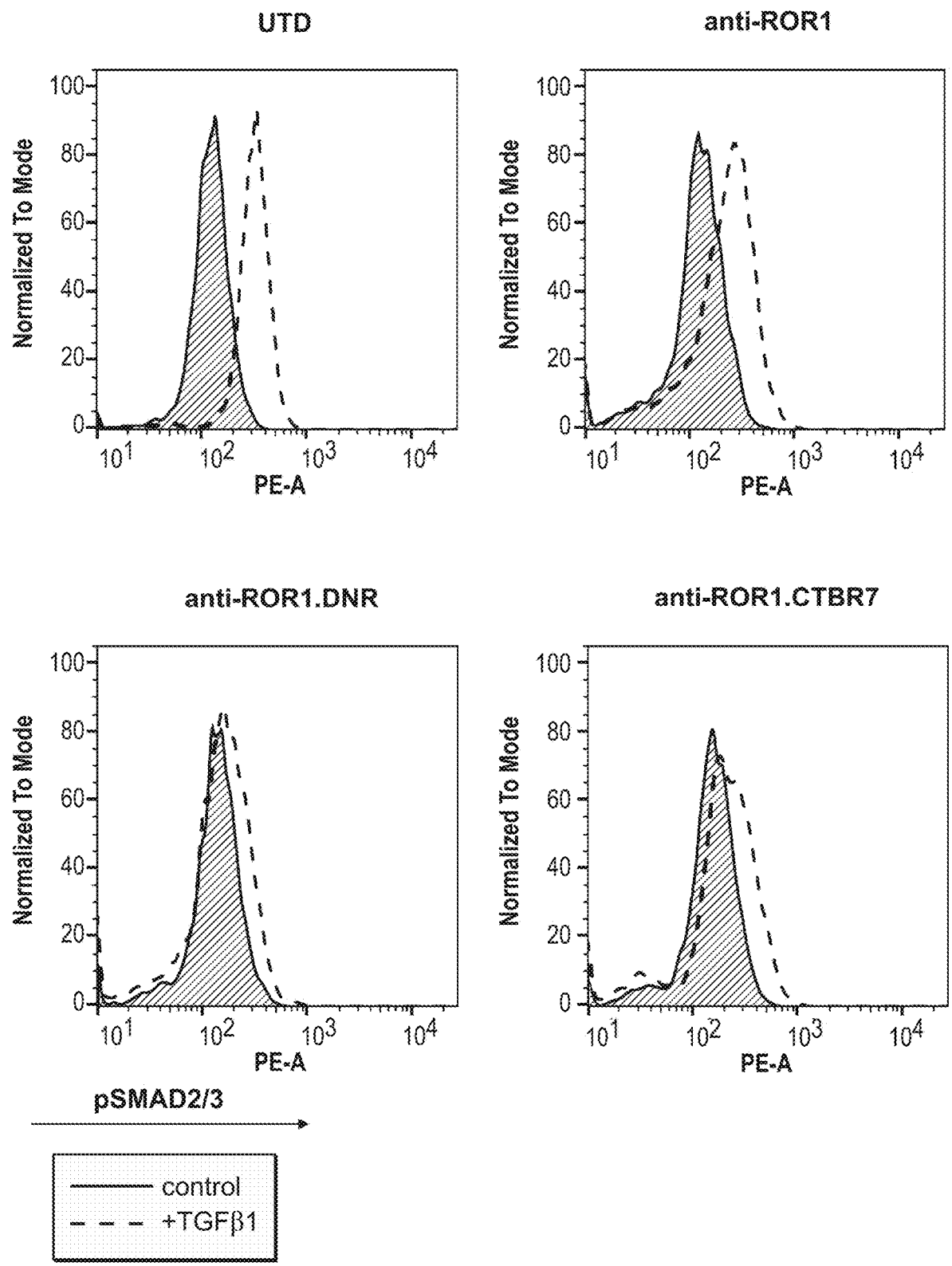
FIG. 10 shows phospho-SMAD2/3 expression in primary human T cells transduced with an anti-ROR1 CAR alone and in combination with the TGFβ DNR, and the CTBR7 signal convertor and treated with TGFβ1.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and CTBR7 (anti-ROR1.CTBR7). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing either CTBR7 or DNR were protected from phosphorylation of SMAD2/3 (FIG. 10). These data demonstrated that expression of CTBR7 rendered anti-ROR1 CART cells insensitive to TGFβ immunosuppressive signaling.

Example 8

CTBR7 Transduces IL-7R Signaling Upon Exposure to TGFβ1

The cellular response to IL-7 is initiated by receptor dimerization and phosphorylation of STAT5. Thus, phospho-STAT5 expression was used to assess IL-7 receptor signaling pathway activation for T cells expressing CTBR7.

Figure 11:
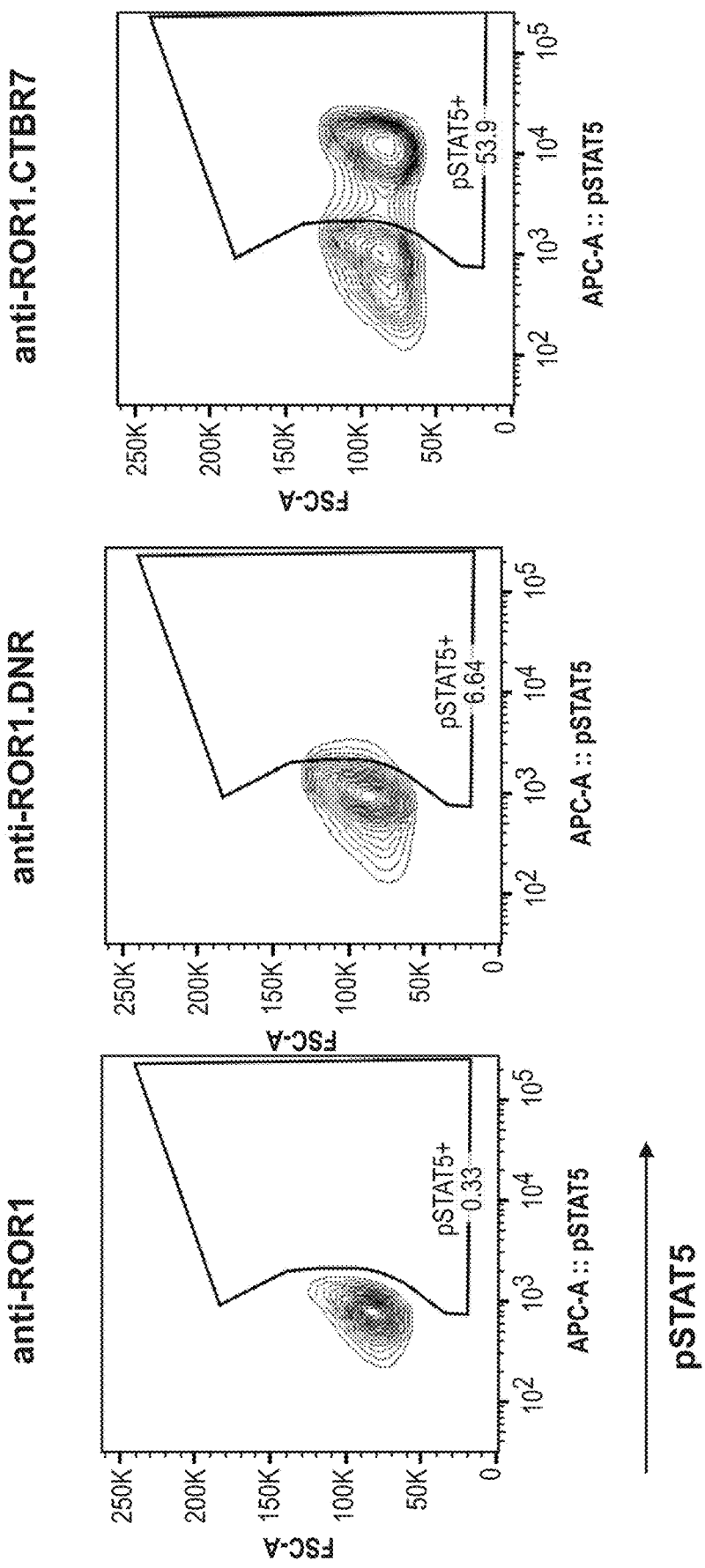
FIG. 11 shows phospho-STAT5 expression in primary human T cells transduced with an anti-ROR1 CAR alone and in combination with the TGFβ DNR, and the CTBR7 signal convertor and treated with TGFβ1.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and CTBR7 (anti-ROR1.CTBR7). After 10 days of culture in IL-2 containing growth media, cultures were treated with 10 ng/mL of recombinant human TGFβ1 for 20 minutes. Only CAR T cells expressing CTBR7 showed detectable levels of phospho-STAT5 expression when treated with recombinant human TGFβ1 (FIG. 11, compare rightmost panel to other panels).

Figure 12:
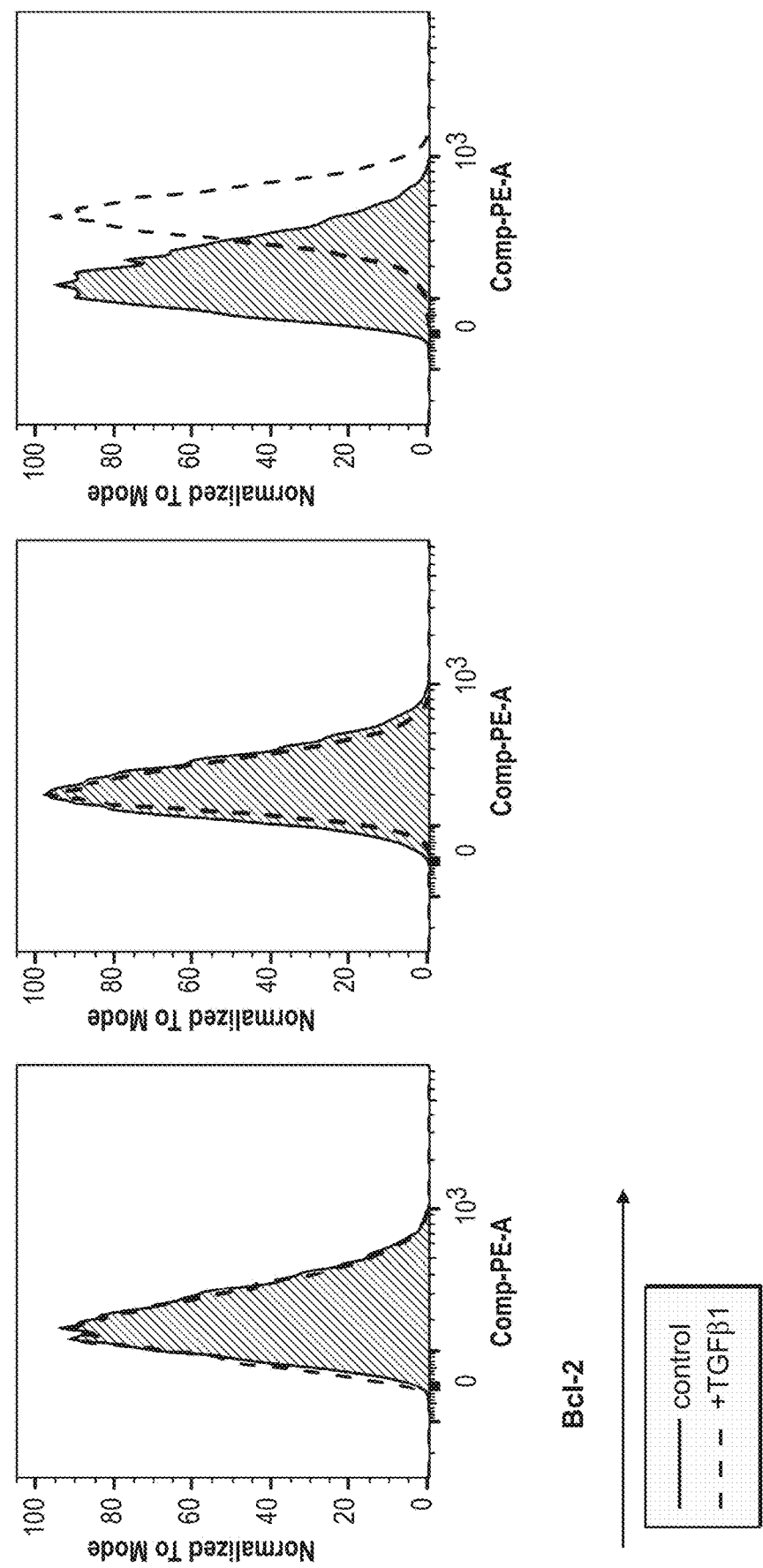
FIG. 12 shows BCL2 expression in primary human T cells transduced with an anti-ROR1 CAR alone and in combination with the TGFβ DNR, and the CTBR7 signal convertor and treated with TGFβ1.

To further interrogate the converted IL-7R signaling, the ability of CTBR7 expressing cells to upregulate Bcl-2 protein expression in response to continuous TGFβ1 exposure was determined. Control CAR T cells or CAR T cells co-expressing either the DNR (anti-ROR1.DNR) or CTBR7 (anti-ROR1.CTBR7) were subjected to an antigen-driven serial expansion assay in absence of exogenous cytokine support and either the presence or absence of TGFβ1. Briefly, GFP-labeled K562 target cells that express human ROR1 antigen were used to serially expand the CAR T cells in the presence or absence of recombinant human TGFβ1. CART cells were stimulated with target cells at a 1:1 ratio once every seven days in the presence or absence of 5 ng/mL recombinant human TGFβ1. Six days following the second stimulation, anti-ROR1 CAR, anti-ROR1 CAR.DNR, or anti-ROR1 CAR.CTBR7 T cells were interrogated for Bcl-2 protein expression by flow cytometry. Only CAR T cells expressing CTBR7 demonstrated increased levels of Bcl-2 protein expression when expanded in the presence of TGFβ1 (FIG. 12).

Example 9

Car T Cells Co-Expressing Ctbr7 Demonstrate Sustained Effector Activity in the Absence of Exogenous IL-2 and Presence of TGFβ1

TGFβ signaling decreases T cell expansion in response to antigen stimulation. In contrast, IL-7 signaling can induce T cell proliferation and survival, an activity that is particularly apparent for memory T cell populations. To assess whether CTBR7 signaling could increase CAR T cell effector activity in the presence of TGFβ1, we compared CAR.CTBR7 expansion and anti-tumor activity against control CAR T cells and CAR.DNR T cells in a serial re-stimulation assay where exogenous IL-2 cytokine support was not provided.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); or (iii) an anti-ROR1 CAR and CTBR7 (anti-ROR1.CTBR7). After 10 days of culture in IL-2 containing growth media, the cells were subjected to an in vitro serial re-stimulation assay in the absence of exogenous IL-2 cytokine support.

Figure 13:
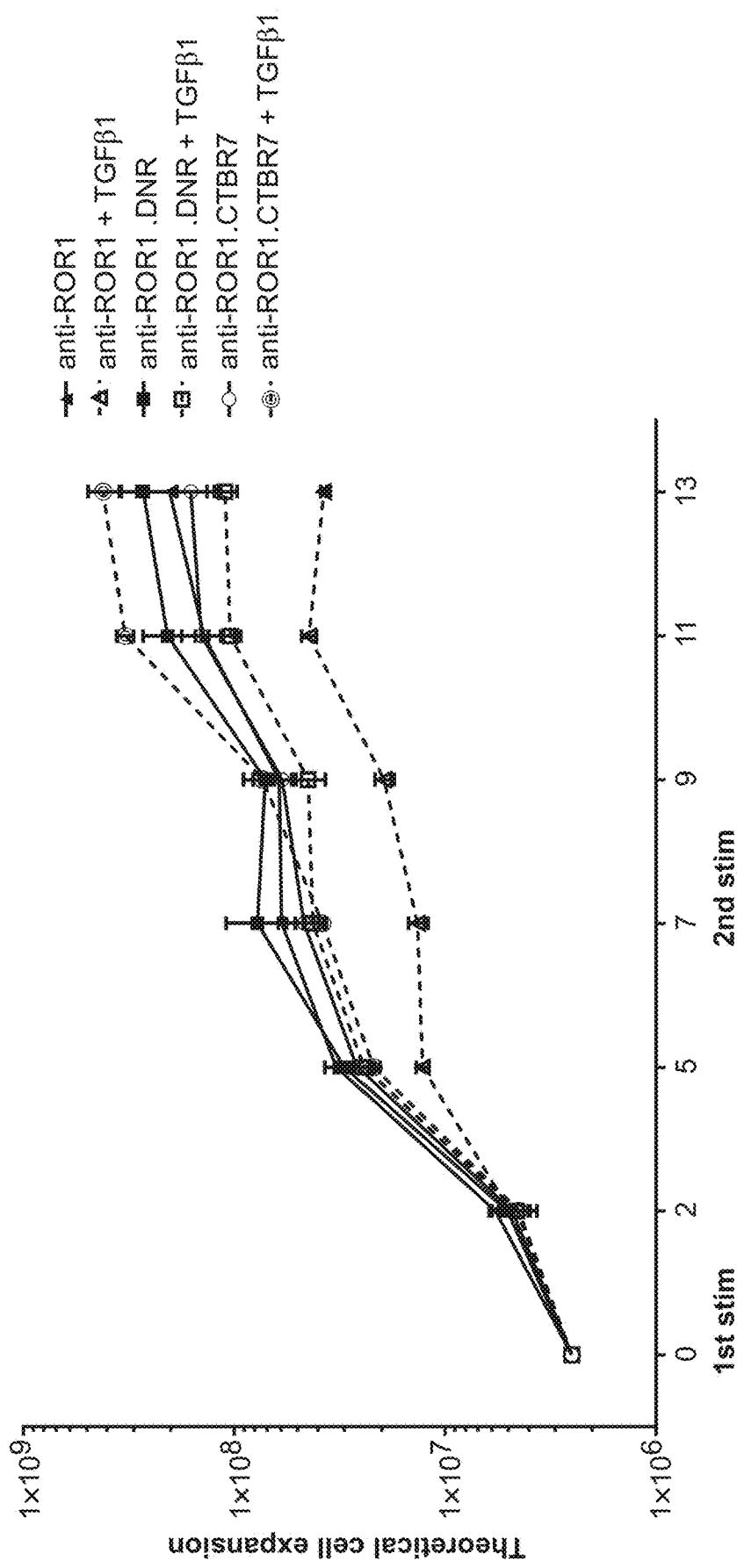
FIG. 13 shows the growth curves for primary human T cells transduced with an anti-ROR1 CAR alone and in combination with the TGFβ DNR or the CTBR7 signal convertor in the presence or absence of TGFβ1.
Figure 14:
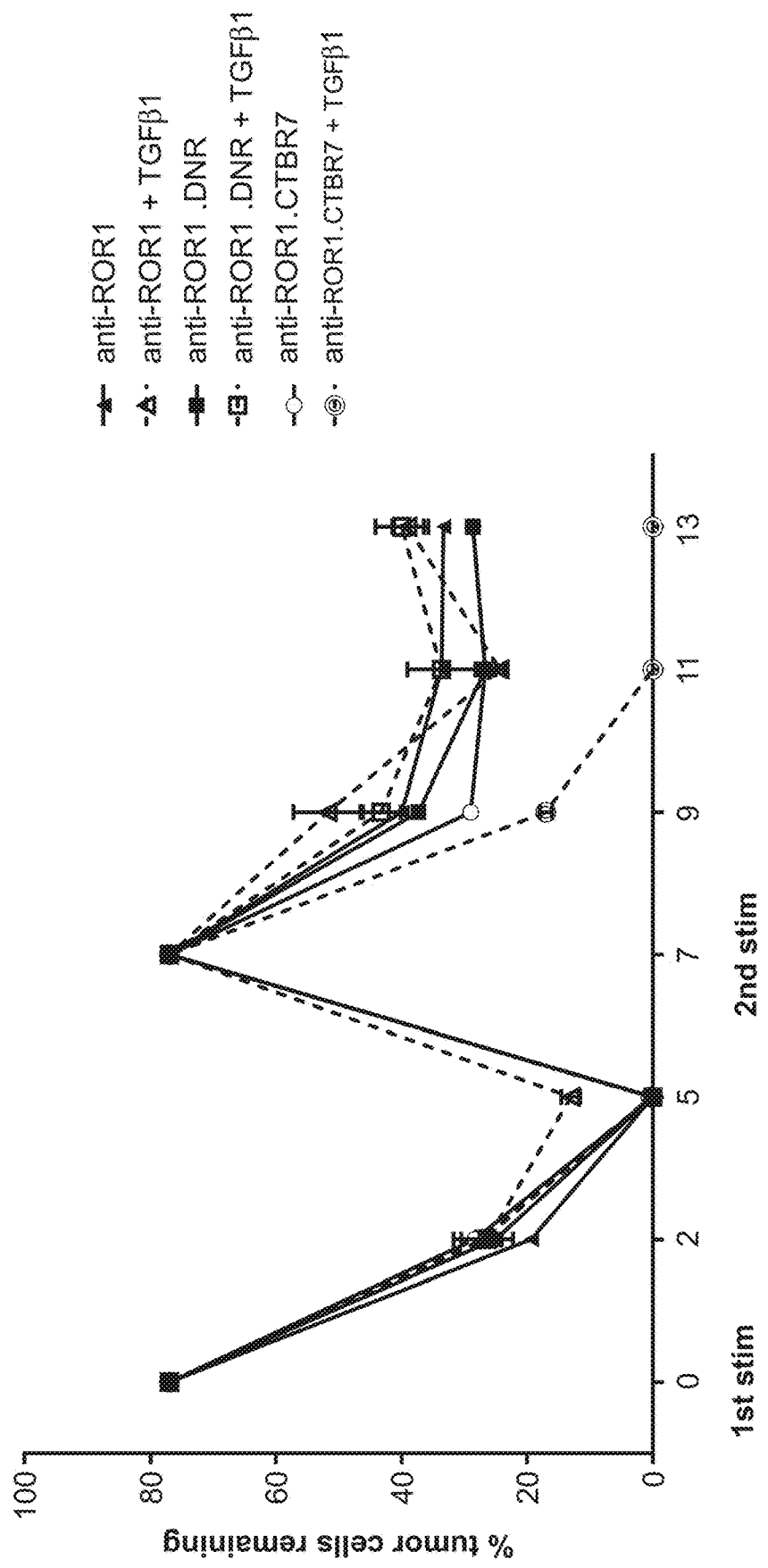
FIG. 14 shows the growth curves for primary human T cells transduced with an anti-ROR1 CAR alone and in combination with the TGFβ DNR or the CTBR7 signal convertor serially re-stimulated with ROR1 expressing target cells in the presence or absence of TGFβ1.

Briefly, GFP-labeled K562 target cells that express human ROR1 antigen were used to serially expand the CAR T cells in the presence or absence of recombinant human TGFβ1. CAR T cells were stimulated with target cells at a 1:1 ratio once every seven days in the presence or absence of 5 ng/mL recombinant human TGFβ1. No exogenous IL-2 was used for support in this assay. Control anti-ROR1 CAR T cells displayed minimal expansion in the presence of 5 ng/mL recombinant human TGFβ1 over the course of the assay. CAR T cells co-expressing the DNR also demonstrated reduced expansion when expanded in the presence of TGFβ1. In contrast, anti-ROR1 CAR T cells co-expressing CTBR7 demonstrated enhanced expansion compared to the same cells expanded in the absence of TGFβ1 (FIG. 13). These data demonstrated that active CTBR7 signaling increased T cell expansion compared to the CAR alone.

CAR T cells co-expressing CTBR7 clear tumor cells from culture in the above-described serial re-stimulation assay with no IL-2 support. After the second round of stimulation, only CAR T cells co-expressing CTBR7 and treated with TGFβ1 completely clear the tumor population (as monitored by the presence of GFP positive tumor cells remaining in culture) (FIG. 13). These data demonstrated that CTBR7 signaling was sufficient to support effector function in conditions where CAR signaling alone was not sufficient.

Example 10

T Cells Expressing a Chimeric Antigen Receptor (CAR) and a CTBR12 or CTBR7

Illustrative TGFβ IL-12R or TGFβ IL-7R signal convertor constructs were designed as shown in FIG. 1.

IL-12Rβ1 and IL-12Rβ2 transmembrane and signaling domains were cloned into a lentiviral vector encoding an anti-EGFR CAR and separated by 2A self-cleaving polypeptide sequences (anti-EGFR.CTBR12).

IL-2Rγ and IL-7Rα transmembrane and signaling domains were cloned into a lentiviral vector encoding anti-EGFR CAR and separated by 2A self-cleaving polypeptide sequences (anti-EGFR. CTBR7).

Figure 15:
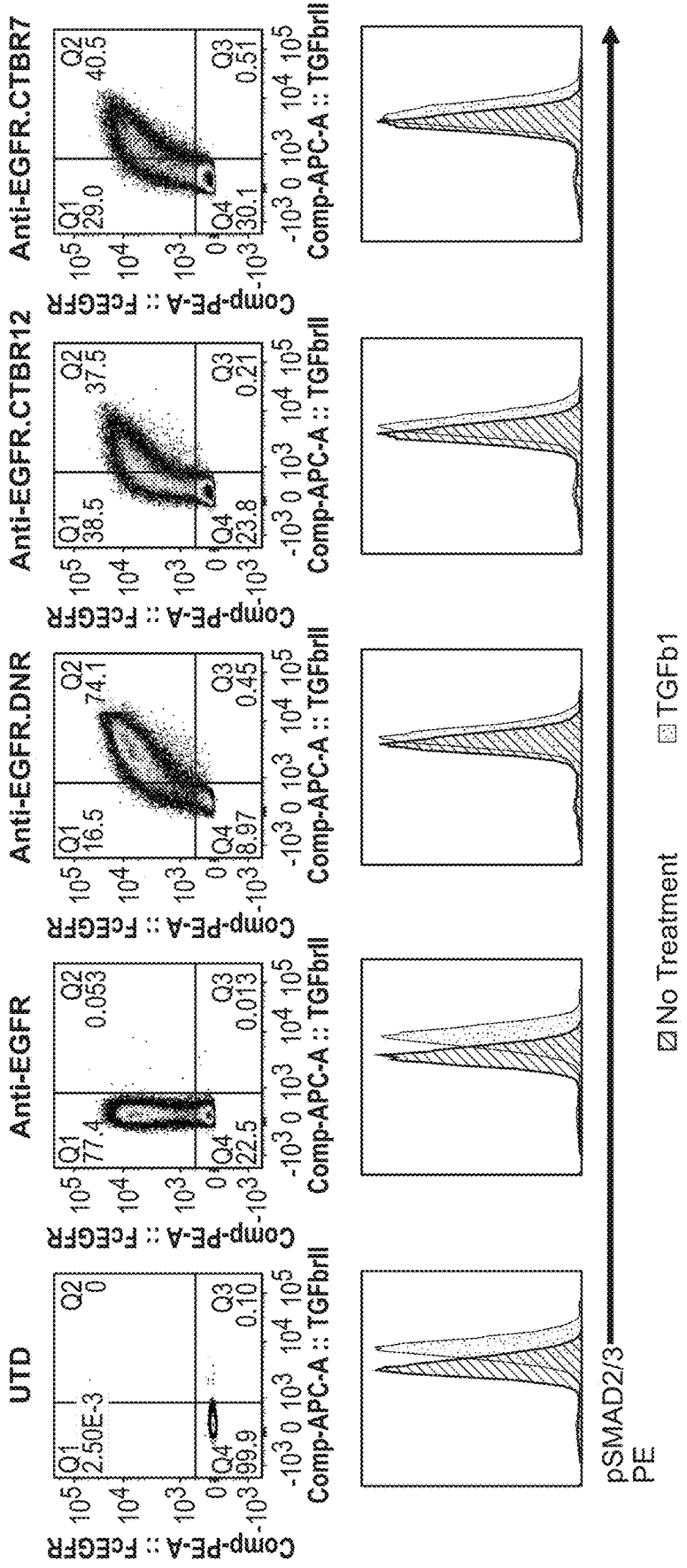
FIG. 15 shows CAR and TGFβR2 subunit expression in primary human T cells transduced with an anti-EGFR CAR alone and in combination with the TGFβ DNR, the CTBR12 signal convertor, and the CTBR7 signal convertor (top panel).

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and dominant negative TGFβ receptor (anti-EGFR.DNR); (iii) an anti-EGFR CAR and CTBR12 (anti-EFGR.CTBR12); and (iv) an anti-EGFR CAR and CTBR7 (anti-EFGR.CTBR7). After 10 days of culture in IL-2 containing growth media, cell surface expression of the anti-EGFR CAR and TGFβR2 was determined by flow cytometry. Representative expression data is shown in FIG. 15 (top panel).

Example 11

Immunosuppressive TGFβ Signaling Inhibited by T Cells Expressing Anti-EGFR CAR and CTBR12 or Anti-EGFR CAR and CTBR7

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and dominant negative TGFβ receptor (anti-EGFR.DNR); (iii) an anti-EGFR CAR and CTBR12 (anti-EFGR.CTBR12); and (iv) an anti-EGFR CAR and CTBR7 (anti-EFGR.CTBR7). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing the DNR, CTBR12 or CTBR7 were completely protected from phosphorylation of SMAD2/3 (FIG. 15, bottom panel). These data demonstrated that expression of either CTBR12 or CTBR7 rendered anti-EGFR CAR T cells insensitive to TGFβ immunosuppressive signaling.

Example 12

CTBR Transduce IL-R Signaling Upon Exposure to TGFβ1

The cellular response to IL-12 is initiated by receptor dimerization and phosphorylation of STAT4 and STAT5. Phospho-STAT4 expression was used to assess IL-12 receptor signaling pathway activation for T cells expressing anti-EGFR.CTBR12.

The cellular response to IL-7 is initiated by receptor dimerization and phosphorylation of STAT5. Thus, phospho-STAT5 expression was used to assess IL-7 receptor signaling pathway activation for T cells expressing anti-EGFR.CTBR7.

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and CTBR12 (anti-EFGR.CTBR12); and (iii) an anti-EGFR CAR and CTBR7 (anti-EFGR.CTBR7). After 10 days of culture in IL-2 containing growth media, T cell cultures were treated with recombinant human IL-12 or recombinant human TGFβ1 for 20 minutes (FIG. 16) or with recombinant human IL-7 or recombinant human TGFβ1 for 20 minutes (FIG. 17).

Figure 16:
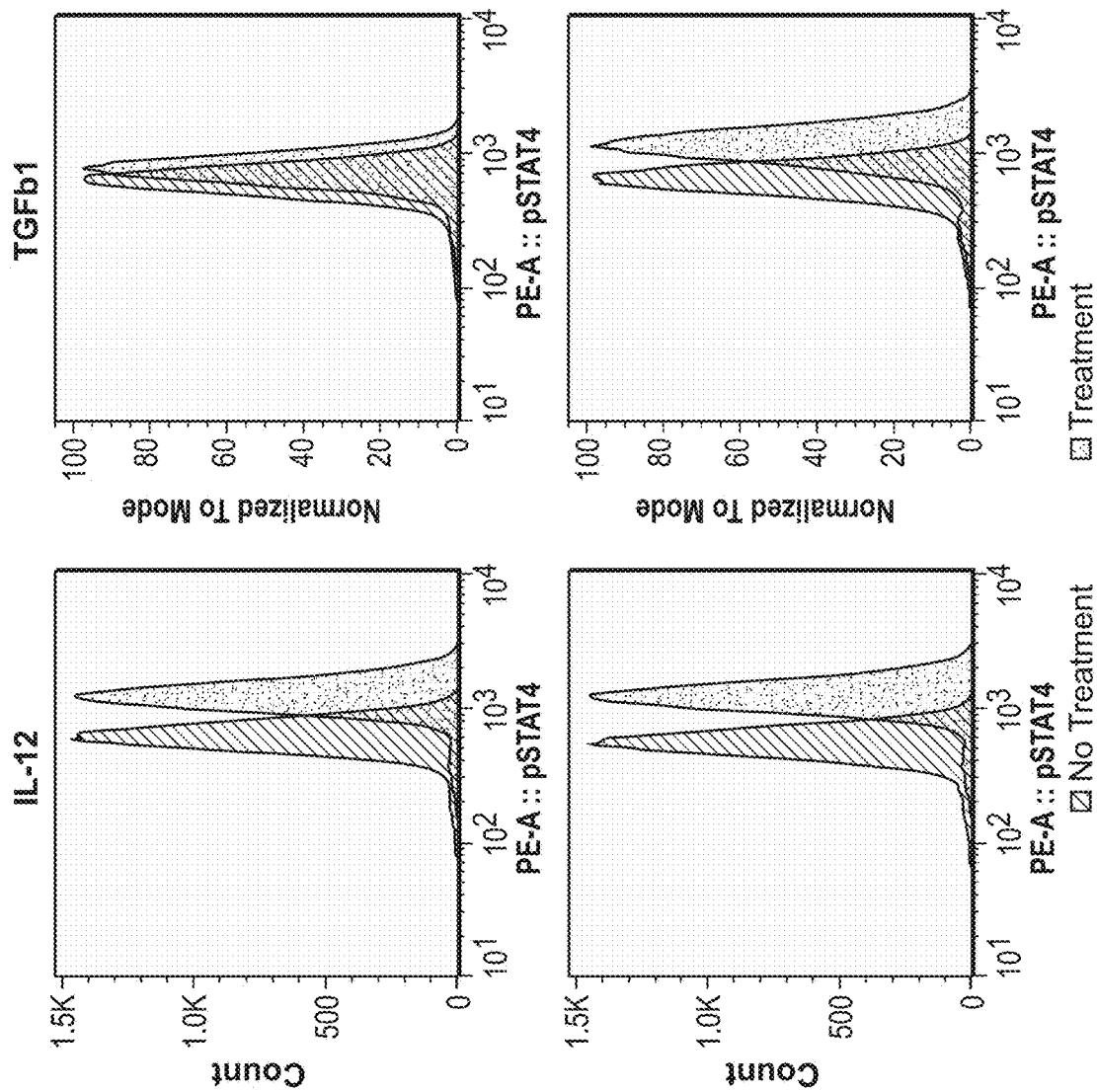
FIG. 16 shows phospho-STAT4 expression in primary human T cells transduced with an anti-EGFR CAR alone and in combination with the TGFβ DNR, and the CTBR12 signal convertor and treated with either IL-12 or TGFβ1.

T cells expressing anti-EGFR CAR or anti-EFGR.CTBR12 shows increased levels of phosphorylated STAT4 in the presence of IL-12 (FIG. 16, left panels), but only T cells expressing anti-EFGR.CTBR12 show increased levels of phosphorylated STAT4 in the presence of TGFβ1 (FIG. 16, lower right panel).

Figure 17:
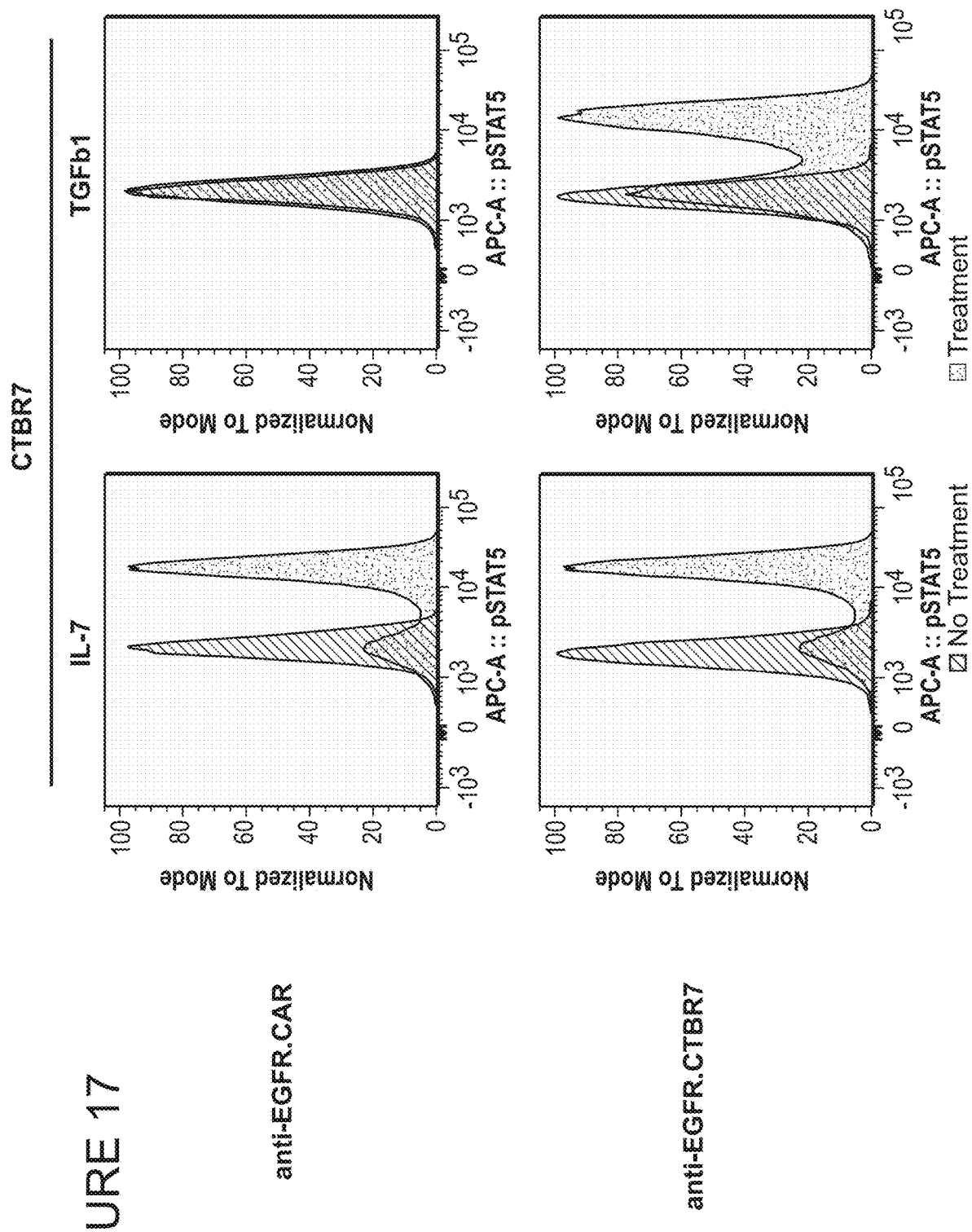
FIG. 17 shows phospho-STAT5 expression in primary human T cells transduced with an anti-EGFR CAR alone and in combination with the TGFβ DNR, and the CTBR7 signal convertor and treated with either IL-7 or TGFβ1.

T cells expressing anti-EGFR CAR or anti-EFGR.CTBR7 shows increased levels of phosphorylated STAT5 in the presence of IL-7 (FIG. 17, left panels), but only T cells expressing anti-EFGR.CTBR7 show increased levels of phosphorylated STAT4 in the presence of TGFβ1 (FIG. 17, lower right panel).

Example 13

CAR T Cells Expressing CTBR12 Secrete Increased IFNγ Upon Exposure to Antigen and TGFβ1

Primary human T cells from healthy donor PBMCs were activated with soluble anti-CD3 (1 µg/mL) and anti-CD28 (5 µg/mL) and transduced with vehicle or lentiviral vectors expressing: (i) an anti-EGFR CAR; (ii) an anti-EGFR CAR and dominant negative TGFβ receptor (anti-EGFR.DNR); or (iii) an anti-EGFR CAR and CTBR12 (anti-EFGR.CTBR12). After 10 days of culture in IL-2 containing growth media, CAR and CTBR expressing T cells were cultured with Jurkat cells (EGFR(−)), A549 cells (EGFR(+)), or HT1080 cells (EGFR(+)) for 48 hours either in the presence or absence of 5 ng/mL recombinant human TGFβ1. Supernatants were collected and analyzed via Luminex for soluble cytokine content.

Figure 18:
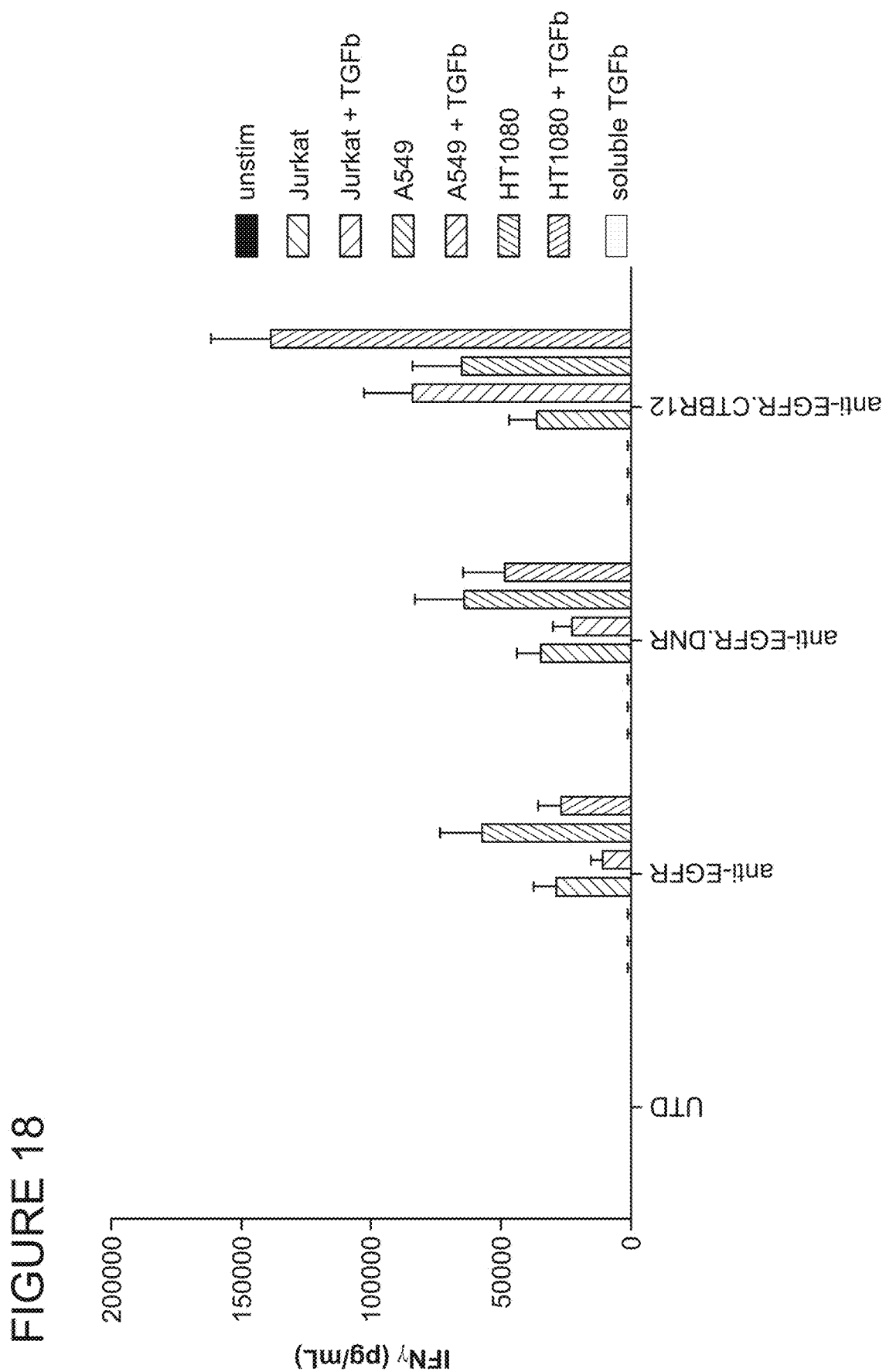
FIG. 18 shows IFNγ secretion from primary human T cells transduced with an anti-EGFR CAR alone and in combination with the TGFβ DNR or the CTBR12 signal convertor and cultured with EGFR (−) or EGFR (+) cell lines in the presence or absence of TGFβ1.

CTBR12 expressing cells produced significantly greater amounts of IFNγ when cultured with EGFR(+) cell lines compared to EGFR(−) cell lines in the presence of recombinant human TGFβ1 (FIG. 18).

Example 14

Anti-Egfr Car T Cells Co-Expressing Ctbr Demonstrate Sustained Effector Activity in the Absence of Exogenous IL-2 and Presence of TGFβ1

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and dominant negative TGFβ receptor (anti-EGFR.DNR); (iii) an anti-EGFR CAR and CTBR12 (anti-EFGR.CTBR12); and (iv) an anti-EGFR CAR and CTBR7 (anti-EFGR.CTBR7). After 10 days of culture in IL-2 containing growth media, the cells were subjected to an in vitro serial re-stimulation assay in the absence of exogenous IL-2 cytokine support.

Figure 19:
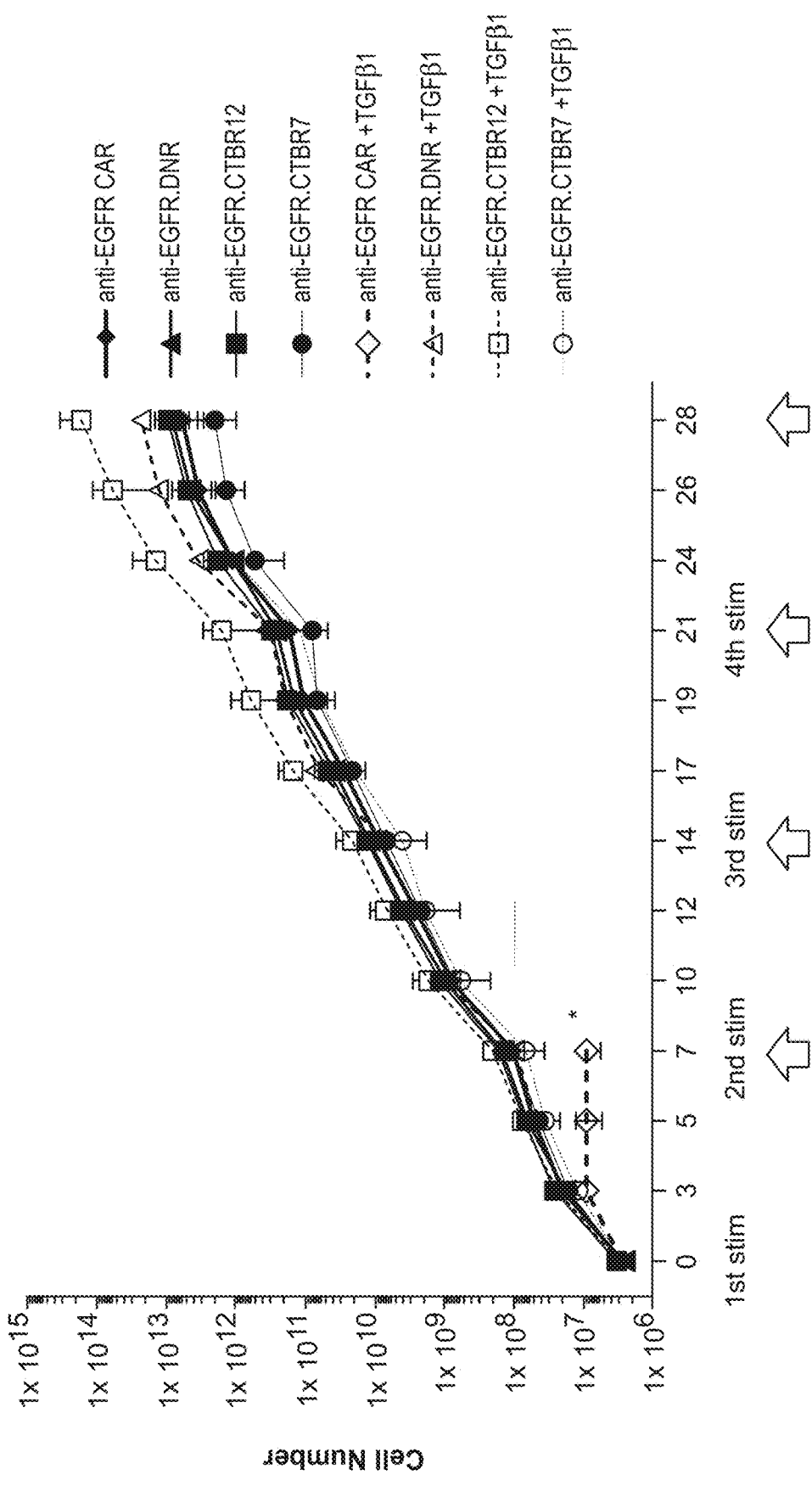
FIG. 19 shows the growth curves for primary human T cells transduced with an anti-EGFR CAR alone and in combination with the TGFβ DNR, the CTBR12 signal convertor, or the CTBR7 signal convertor serially re-stimulated with EGFR expressing target cells in the presence or absence of TGFβ1.

Briefly, GFP-labeled target cells that express human EGFR antigen were used to serially expand the CART cells in the presence or absence of recombinant human TGFβ1. CAR T cells were stimulated with target cells at a 1:1 ratio once every seven days in the presence or absence of 5 ng/mL recombinant human TGFβ1. No exogenous IL-2 was used for support in this assay. Control anti-EGFR CAR T cells displayed minimal expansion in the presence of 5 ng/mL recombinant human TGFβ1 through the first stimulation and were not cultured further. CAR T cells co-expressing the DNR also demonstrated reduced expansion when expanded in the presence of TGFβ1. In contrast, anti-EGFR CAR T cells co-expressing CTBR12 or CTBR7 demonstrated enhanced expansion compared to the same cells expanded in the absence of TGFβ1 (FIG. 19). These data demonstrated that active CTBR12 or CTBR7 signaling increased T cell expansion compared to the CAR alone.

Example 15

NY-ESO1 TCR T Cells Co-Expressing Ctbr Demonstrate Sustained Effector Activity in the Absence of Exogenous IL-2 and Presence of TGFβ1

Illustrative TCR-based TGFβ IL-12R and TGFβ IL-R signal convertor constructs were designed as shown in FIG. 20.

IL-12Rβ1 and IL-12Rβ2 transmembrane and signaling domains were cloned into a lentiviral vector encoding an anti-NY-ESO1 TCR and separated by 2A self-cleaving polypeptide sequences (NY-ESO1.CTBR12).

IL-2Rγ and IL-7Rα transmembrane and signaling domains were cloned into a lentiviral vector encoding NY-ESO1 TCR and separated by 2A self-cleaving polypeptide sequences (NY-ESO1.CTBR7).

Primary human T cells from healthy donor PBMCs were activated with soluble anti-CD3 (1 µg/mL) and anti-CD28 (5 µg/mL) and transduced with vehicle or lentiviral vectors expressing (i) an NY-ESO1 TCR; (ii) an NY-ESO1 TCR and dominant negative TGFβ receptor (NY-ESO1.DNR); (iii) an NY-ESO1 TCR and CTBR12 (NY-ESO1.CTBR12); and (iv) an NY-ESO1 TCR and CTBR7 (NY-ESO1.CTBR7). After 10 days of culture in IL-2 containing growth media, cell surface expression of the NY-ESO1 TCRR and TGFβR2 was determined by flow cytometry. All constructs were expressed.

Example 16

Immunosuppressive TGFβ Signaling Inhibited by T Cells Expressing NY-ESO TCR and CTBR12 or NY-ESO TCR and CTBR7

Figure 21:
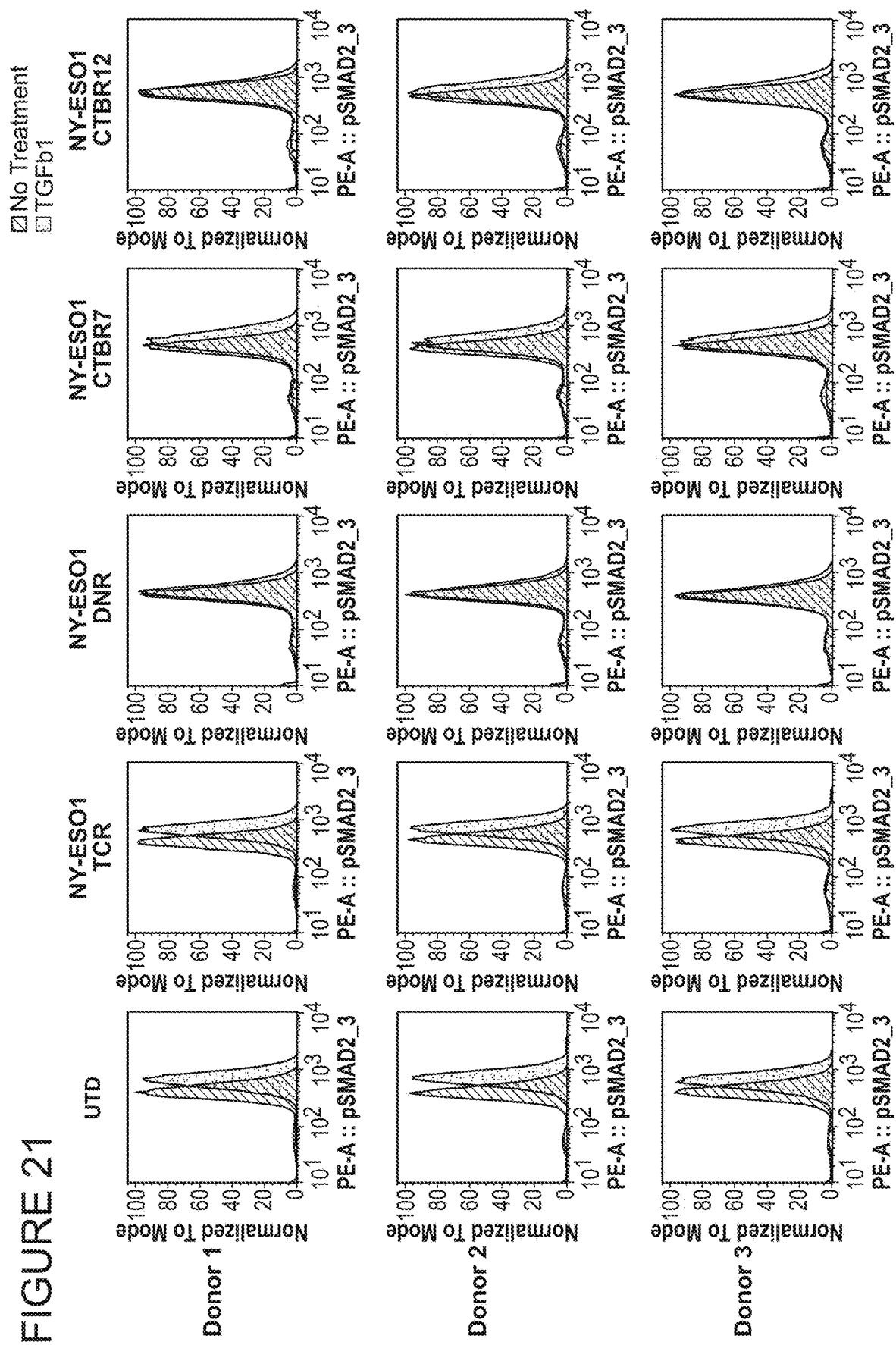
FIG. 21 shows phospho-SMAD2/3 expression in primary human T cells transduced with an NY-ESO1 TCR, NY-ESO1.DNR, NY-ESO1.CTBR7, and NY-ESO1.CTBR12 and treated with TGFβ1 compared to untreated cells.

Primary human T cells from healthy donor PBMCs were activated with soluble anti-CD3 (1 µg/mL) and anti-CD28 (5 µg/mL) and transduced with vehicle or lentiviral vectors expressing (i) an NY-ESO1 TCR; (ii) an NY-ESO1 TCR and dominant negative TGFβ receptor (NY-ESO1.DNR); (iii) an NY-ESO1 TCR and CTBR12 (NY-ESO1.CTBR12); and (iv) an NY-ESO1 TCR and CTBR7 (NY-ESO1.CTBR7). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing the DNR, CTBR12 or CTBR7 were completely protected from phosphorylation of SMAD2/3 (FIG. 21). These data demonstrated that expression of either CTBR12 or CTBR7 rendered NY-ESO1 TCR T cells insensitive to TGFβ immunosuppressive signaling.

Example 17

CTBR Transduce IL-R Signaling Upon Exposure to TGFβ1

The cellular response to IL-12 is initiated by receptor dimerization and phosphorylation of STAT4 and STAT5. Phospho-STAT4 expression was used to assess IL-12 receptor signaling pathway activation for T cells expressing NY-ESO1.CTBR12.

The cellular response to IL-7 is initiated by receptor dimerization and phosphorylation of STAT5. Thus, phospho-STAT5 expression was used to assess IL-7 receptor signaling pathway activation for T cells expressing NY-ESO1.CTBR7.

Figure 22:
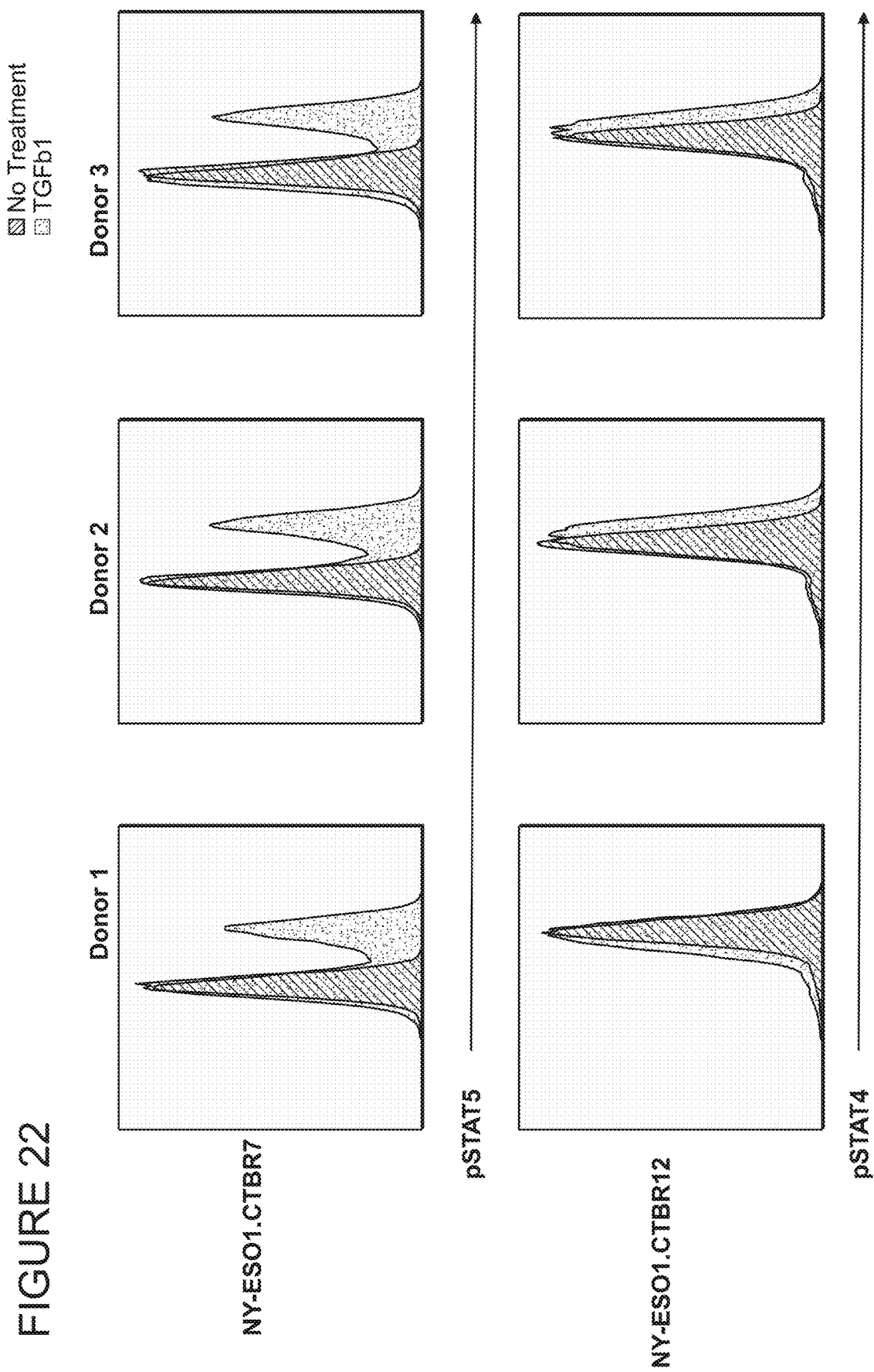
FIG. 22 shows phospho-STAT5 expression in primary human T cells transduced with an NY-ESO1.CTBR7 and treated with either IL-7 or TGFβ1 (top panel).

Primary human T cells from healthy donor PBMCs were activated with soluble anti-CD3 (1 µg/mL) and anti-CD28 (5 µg/mL) and transduced with vehicle or lentiviral vectors expressing (i) an NY-ESO1 TCR and CTBR12 (NY-ESO1.CTBR12); and (ii) an NY-ESO1 TCR and CTBR7 (NY-ESO1.CTBR7). After 10 days of culture in IL-2 containing growth media, T cell cultures were treated with recombinant human IL-7 or recombinant human TGFβ1 for 20 minutes (FIG. 22, top panel) or with recombinant human IL-12 or recombinant human TGFβ1 for 20 minutes (FIG. 22, bottom panel).

Example 18

CAR T Cells Expressing CTBR12 Secrete Increased IFNγ Upon Exposure to Antigen and TGFβ1

Primary human T cells from healthy donor PBMCs were activated with soluble anti-CD3 (1 µg/mL) and anti-CD28 (5 µg/mL) and transduced with vehicle or lentiviral vectors expressing: (i) an NY-ESO1 TCR; (ii) an NY-ESO1 TCR and dominant negative TGFβ receptor (NY-ESO1.DNR); (iii) an NY-ESO1 TCR and CTBR12 (NY-ESO1.CTBR12); and (iv) an NY-ESO1 TCR and CTBR7 (NY-ESO1.CTBR7). After 10 days of culture in IL-2 containing growth media, CAR and CTBR expressing T cells were cultured with SaOs2 cells (A2, NY-ESO1(+)) or A549.A2.NY-ESO1 cells (A2, NY-ESO1(+)) at a 5:1 ratio of T cells to target cells for 48 hours either in the presence or absence of 5 ng/mL recombinant human TGFβ1. Supernatants were collected and analyzed via Luminex for soluble cytokine content.

CTBR12 expressing cells produced significantly greater amounts of IFNγ when cultured with A2 and NY-ESO1 (+) cell lines in the presence of recombinant human TGFβ1 compared to A2 and NY-ESO1 (+) cell lines (FIG. 23). CTBR expressing cells demonstrates resistance to immunosuppressive TGFβ signaling.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A polynucleotide encoding a fusion polypeptide comprising:
   (a) a first polypeptide comprising an amino acid sequence having at least 95% identity to the amino acid sequence set forth in SEQ ID NO: 27;
   (b) a viral self-cleaving 2A peptide; and
   (c) a second polypeptide comprising an amino acid sequence having at least 95% identity to the amino acid sequence set forth in SEQ ID NO: 26;
   wherein the fusion polypeptide increases STAT4 and/or STAT5 phosphorylation when expressed in a cell in the presence of extracellular TGFβ1.

2. The polynucleotide of claim 1, wherein the viral self-cleaving 2A polypeptide is a porcine teschovirus-1 (PTV-1) (P2A) peptide.

3. The polynucleotide of claim 1, wherein the fusion polypeptide further comprises (i) an engineered antigen receptor and (ii) a second polypeptide cleavage signal or viral self-cleaving 2A polypeptide.

4. A lentiviral vector comprising the polynucleotide of claim 1.

5. A cell comprising the polynucleotide of claim 1.

6. The cell of claim 5, wherein the cell is:
   (a) a hematopoietic cell;
   (b) a T cell;
   (c) a CD3$^+$, CD4$^+$, and/or CD8$^+$ cell;
   (d) an immune effector cell;
   (e) a cytotoxic T lymphocyte (CTL), a tumor infiltrating lymphocyte (TIL), or a helper T cell; or
   (f) a natural killer (NK) cell or natural killer T (NKT) cell.

7. The cell of claim 6, wherein the cell is a T cell.

8. The cell of claim 6, wherein the cell is an immune effector cell.

9. The cell of claim 6, wherein the cell is a cytotoxic T lymphocyte (CTL).

10. A composition comprising the cell of claim 6.

11. The polynucleotide of claim 1, wherein the first polypeptide comprises the amino acid sequence set forth in SEQ ID NO: 27.

12. The polynucleotide of claim 1, wherein the second polypeptide comprises the amino acid sequence set forth in SEQ ID NO: 26.

13. The polynucleotide of claim 1, wherein the first polypeptide comprises the amino acid sequence set forth in SEQ ID NO: 27 and the second polypeptide comprises the amino acid sequence set forth in SEQ ID NO: 26.

14. A polynucleotide encoding a fusion polypeptide comprising an amino acid sequence having at least 95% identity to the amino acid sequence set forth in SEQ ID NO: 28, wherein the fusion polypeptide increases STAT4 and/or STAT5 phosphorylation when expressed in a cell in the presence of extracellular TGFβ1.

15. The polynucleotide of claim 14, wherein the viral self-cleaving 2A polypeptide is a porcine teschovirus-1 (PTV-1) (P2A) peptide.

16. The polynucleotide of claim 14, wherein the fusion polypeptide further comprises (i) an engineered antigen receptor and (ii) a second polypeptide cleavage signal or viral self-cleaving 2A polypeptide.

17. A lentiviral vector comprising the polynucleotide of claim 14.

18. A cell comprising the polynucleotide of claim 14.

19. The cell of claim 18, wherein the cell is:
   (a) a hematopoietic cell;
   (b) a T cell;
   (c) a CD3$^+$, CD4$^+$, and/or CD8$^+$ cell;
   (d) an immune effector cell;
   (e) a cytotoxic T lymphocyte (CTL), a tumor infiltrating lymphocyte (TIL), or a helper T cell; or
   (f) a natural killer (NK) cell or natural killer T (NKT) cell.

20. The cell of claim 19, wherein the cell is a T cell.

21. The cell of claim 19, wherein the cell is an immune effector cell.

22. The cell of claim 19, wherein the cell is a cytotoxic T lymphocyte (CTL).

23. A composition comprising the cell of claim 19.

24. The polynucleotide of claim 14, wherein the fusion polypeptide comprises the amino acid sequence set forth in SEQ ID NO: 28.

* * * * *